(12) United States Patent
Kolodner et al.

(10) Patent No.: US 7,396,678 B1
(45) Date of Patent: Jul. 8, 2008

(54) METHOD FOR DETECTION OF ALTERATIONS IN THE DNA MISMATCH REPAIR PATHWAY

(75) Inventors: Richard D. Kolodner, Jamaica Plain, MA (US); Robert A. G. Reenan, Madison, WI (US); Richard Fishel, Penn Valley, PA (US)

(73) Assignees: Dana-Farber Cancer Institute, Boston, MA (US); University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 08/465,251

(22) Filed: Jun. 5, 1995

Related U.S. Application Data

(63) Continuation-in-part of application No. 08/259,310, filed on Jun. 13, 1994, now abandoned, which is a continuation-in-part of application No. 08/163,449, filed on Dec. 7, 1993, now abandoned, which is a continuation-in-part of application No. 08/154,792, filed on Nov. 17, 1993, now abandoned.

(51) Int. Cl.
  *C12P 21/06* (2006.01)
  *C07H 17/00* (2006.01)
(52) U.S. Cl. .................... 435/320.1; 536/23.1
(58) Field of Classification Search ............. 536/23.5; 435/320.1
  See application file for complete search history.

(56) References Cited

FOREIGN PATENT DOCUMENTS

WO  WO 95/15381  6/1995
WO  WO 95/20678  8/1995

OTHER PUBLICATIONS

Schlensog, V. et al., "The *Escherichia coli fdv* Gene Probably Encodes MutS and Is Located at Minute 58.8 Adjacent to the *hyc-hyp* Gene Cluster", J. Bacteriol., vol. 173, No. 23, pp. 7414-7415, Dec. 1991.
New, L. et al., "The Yeast Gene *MSH3* Defines a New Class of Eukaryotic MutS Homologues", Molecular & General Genetics, vol. 239, No. 1-2, pp. 97-108, May 1993.
Fishel, R. et al., "The Human Mutator Gene Homolog *MSH2* and Its Association with Hereditary Nonpolyposis Colon Cancer", Cell, vol. 75, No. 5, pp. 1027-1038, Dec. 3, 1993, and Cell, vol. 77, No. 1, p. 167, Apr. 8, 1994.
Bronner, C.E. et al., "Mutation in the DNA Mismatch Repair Gene Homologue *hMLH1* Is Associated With Hereditary Non-Polyposis Colon Cancer", Nature, vol. 368, pp. 258-261, Mar. 17, 1994.
Jiricny, J., "Colon Cancer and DNA Repair: Have Mismatches Met Their Match?", Trends in Genetics, vol. 10, No. 5, pp. 164-168, May 1994.

Reenan, R.A.G. et al., "Isolation and Characterization of Two: *Saccharomyces cerevisiae* Genes Encoding Homologs of the Bacterial HexA and MutS Mismatch Repair Proteins", Genetics, vol. 132, pp. 963-973, Dec. 1992.
Reenan, R.A.G. et al., "Characterization of Insertion Mutations in the *Saccharomyces cerevisiae MSH1* and *MSH2* Genes: Evidence for Separate Mitochondrial and Nuclear Functions", Genetics, vol. 132, pp. 975-985, Dec. 1992.
Marx, J., "New Colon Cancer Gene Discovered", Science, vol. 260, pp. 751-752, May 7, 1993.
Peltomaki, P. et al., "Genetic Mapping of a Locus Predisposing to Human Colorectal Cancer", Science, vol. 260, pp. 810-812, May 7, 1993.
Aaltonen, L.A. et al., "Clues to the Pathogenesis of Familial Colorectal Cancer", Science, vol. 260, pp. 812-816, May 7, 1993.
Thibodeau, S.N. et al., "Microsatellite Instability in Cancer of the Proximal Colon", Science, vol. 260, pp. 816-819, May 7, 1993.
Leach, F.S. et al., "Mutations of a MutS Homolog in Hereditary Nonpolyposis Colorectal Cancer", Cell, vol. 75, pp. 1215-1225, Dec. 17, 1993.
Henderson, S.T. et al., "Instability of Simple Sequence DNA in *Saccharomyces cerevisiae*", Molecular and Cellular Biology, vol. 12, No. 6, pp. 2749-2757, Jun. 1992.
Nelson, D.L., "Trinucleotide Repeat Instability: When and Where?", Genetics, vol. 4, pp. 107-108, Jun. 1993.
Kunkel, T.A., "Slippery DNA and Diseases", Nature, vol. 365, pp. 207-208, Sep. 16, 1993.
Strand, M. et al., "Destabilization of Tracts of Simple Repetitive DNA in Yeast By Mutations Affecting DNA Mismatch Repair", Nature, vol. 365, pp. 274-276, Sep. 16, 1993.
Kat, A. et al., "An Alkylation-Tolerant, Mutator Human Cell Line is Deficient in Strand-Specific Mismatch Repair", Proc. Natl. Acad. Sci. USA, Genetics, vol. 90, pp. 6424-6428, Jul. 1993.
Saltus, R., "Flawed Gene Called Link to Colon Cancer", The Boston Globe, Dec. 3, 1993.
Walholz, M., "Scientists Find Gene That Causes Cancers", The Wall Street Journal, Dec. 3, 1993.

(Continued)

*Primary Examiner*—Karen Cochrane Carlson
(74) *Attorney, Agent, or Firm*—Ivor R. Elrifi; Cynthia A. Kozakiewicz; Mintz, Levin, Cohn, Ferris, Glovasky and Popeo, P.C.

(57) ABSTRACT

We have now discovered that eukaryotes, including mammals, have a DNA mismatch repair pathway analogous to the pathway that exists in bacteria. Defects or alterations in this mismatch repair pathway in a mammal, such as a human, will result in the accumulation of unstable repeated DNA sequences. Such a phenotype has a high correlation to disease state in a number of cancers, such as hereditary colon cancers. Accordingly, discovering a defect or alteration in the pathway can be diagnostic of a predisposition to cancer, and prognostic for a particular cancer. We have also discovered and sequenced one of the genes in this pathway in a number of mammals, including humans. This gene, referred to herein as MSH2, has many applications. It can be used in assays, to express gene product, for drug screens, and therapeutically. We also disclose herein a method for screening for other genes in this mismatch repair pathway.

7 Claims, 6 Drawing Sheets

OTHER PUBLICATIONS

Angier, N., "Scientists Isolate Novel Gene Linked to Colon Cancer", New York Times, Dec. 3, 1993.
Gorman, C., "Catching a Rogue Gene", Time, p. 58, Dec. 13, 1993.
Hughes, M.J. et al., "The Purification of a Human Mismatch-Binding Protein and Identification of Its Associate ATPase and Helicase Activities", The Journal of Biological Chemistry, vol. 267, No. 33, issue of Nov. 25, 1992, pp. 23876-23882, 1992.
Jiricny, J., et al., "A Human 200-kDa Protein Binds Selectively to DNA Fragments Containing G-T Mismatches", Proc. Natl. Acad. Sci. USA, vol. 85, pp. 8860-8864, Dec. 1988.
Palombo, F. et al., "Mismatch Repair and Cancer", Nature, vol. 367, p. 417, Feb. 3, 1994.

```
           MAVTRKELLQLDVAAEVGFVKKFTGLPEKPLTTVRLVDKGDFYTAIGSDALLAADSVFKTQGVLKNCQLGPAGAKNLQSPTKYVVSLQVLASLVKLLLL
                 10        20        30        40        50        60        70        80        90       100
HUMAN MAVQPKETLQLESAAEVGFVRFFQGMPEKPTTVRLFDRGDFYTAHGEDALLAAREVFKTQGVIKY--MGPAGAKNLQS---VVLSKMNFESFVKDLLL  94
YEAST MSSTRPELKFSDVSEERNFYKKYTGLPKKPLKTIRLVDKGDYYTVIGSDAIFVADSVYHTQSVLKNCQLDPVTAKNFHEPTKVTVSLQVLATLLKLCLL 100

VLGYTKVEVYKNRAGNKASKDNGWKLAKSASPGNLSQVEDLLNGNIDSSAIIGVVGVQWSAVDGNRIVGVGFVDSIARKVGLLDIVDNDVFSNLEALLIQL
             110       120       130       140       150       160       170       180       190       200
HUMAN VRQYRVEVYKNRAGNKASKENDWYLAYKASPGNLSQFEDILFGNNDMSASIGVVGVKMSAVDGQRQVGVGYVDSIQRKLGLCEFPDNDQFSNLEALLIQI 194
YEAST DLGYKVEIY-------DKGWKLIKSASPGNIEQVNELMNMNIDSSIIIASLKVQMNSQDGNCIIGVAFIDTTAYKVGMLDIVDNEVYSNLESFLIQL     190

GVKECVVQGLTSNGESAGDMGKVINVIDRGGIVTLLKNADFSTKDVELDLTKLLKGKKGDDLNAAVLPEKESQVAVGALSAVIGFLELLSDDSNVGQFE
             210       220       230       240       250       260       270       280       290       300
HUMAN GPKECVLPG---GETAGDMGKLRQIIQRGGILITERKKADFSTKDIYQDLNRLLKGKKGEQMNSAVLPEMENQVAVSSLSAVIKFLELLSDDSNFGQFE 290
YEAST GVKECLVQDLTSNSNSNAEMQKVINVIDRCGVVTLLKNSEFSEKDVELDLTKLL----GDDL-ALSLPQKYSKLSMGACNALIGYLQLLSEQDQVGKYE 285

LVTHDLSEFMKLDAAAVKALNLFQGGVEDTTGSNSLAASGFTSAGNSGKVTSLFQLLNKCKTNAGVRLVNEMLKQPLTDIEIEERLDLVDALVDDAELR
             310       320       330       340       350       360       370       380       390       400
HUMAN LTTFDFSQYMKLDIAAVRALNLFQGSVEDTTGSQSLAA-------LLNKCKTPQGQRLVNQWIKQPLMDKNRIEERLNLVEAFVEDAELR           373
YEAST LVEHKLKEFMKLDASAIKALNLFPQGPQNPFGSNNLAVSGFTSAGNSGKVTSLFQLLNHCKTNAGVRLLNEWLKQPLTNIDEINKRHDLVDYLIDQIELR 385

QTLTSDLLRRIPDLNRLAKKLNKQGANLEDVLKLYQGINQLPEVVQALTSFLEDDSHTGKVNELVLAVFVAPLSDLVSDLSKFEEMVETTVDLAVEENN
             410       420       430       440       450       460       470       480       490       500
HUMAN QTLQEDLLRRFPDLNRLAKKFQRQAANLQDCYRLYQGINQLPNVIQAL------EKHEGKHQKLLLAVFVTPLTDLRSDFSKFQEMIETTLDMDQVE-NH 466
YEAST QMLTSEYLPMIPDIRRLTKKLNKRG-NLEDVLKIYQFSKRIPEIVQFTSFLEDDSPTEPVNELVRSWLAPLSHHVEPLSKFEEMVETTVDLAYEENN    484

EFLVKVSFDEELGELRSILDTLEDEIQSILLSAAEEDIGLDPGKQLKLDSSALHGYFRVTRNDAKVLRNNKNFITVSIVKAGVKFSTSQLTSLAEETTIL
             510       520       530       540       550       560       570       580       590       600
HUMAN EFLVKPSFDPNLSELREIMNDLEKKMQSTLISAARDIGLDPGKQIKLDSSAQFGYYFRVTCKEEKVLRNNKNFSTVDIQKNGVKFTNSKLTSLNEEYTKN 566
YEAST EFMIKVEFNEELGKIRSKLDTLRDEIHSIHLDSAEDLGFDPDKKLKLENHHLHGWCMRLTRNDAKELRKHKKYIELSTVKAGIFFSTKQLKSIANETNIL 584

QTEYDEAQSALVKEIVNISLGYVEVFETLSLVLAQLDAVASFAHVSSGAPVPYVRPALLEKGSGRIIHLIASRHAVVEVQDDIAFISNDVTLESGKGDFL
             610       620       630       640       650       660       670       680       690       700
HUMAN KTEYEEAQDAIVKEIVNISSGYVEPMQTLNDVLAQLDAVVSFAHVSNGAPVPYVRPAILEKGQGRII-LKASRHACVEVQDEIAFIPNDVYFEKDKQMFH 665
YEAST QKEYDKQQSALVREIINITLTYTPVFEKLSLVLAHLDVIASFAHTSSYAPIPYIRPKLHPMDSERRTHL±SSRHPVLEMQDDISFISNDVTLESGKGDFL 684
```

FIG. 3A

```
HUMAN  IITGPNMGGKSTYIRQVGVIVLMAQIGCFVPCESAEVAIVDAILARVGAGDSQLKGVSTFMAEILETASILKSASKDSLIIVDELGRGTSTYDGFGLAWA
              710       720       730       740       750       760       770       780       790       800
HUMAN  IITGPNMGGKSTYIRQTGVIVLMAQIGCFVPCESAAEVSIVDCILARVGAGDSQLKGVSTFMAEMLETASILRSATKDSLIIIDELGRGTSTYDGFGLAWA  765
YEAST  IITGPNMGGKSTYIRQVGVISLMAQIGCFVPCEERAEIAIVDAILCRVGAGDSQLKGVSTFMVEILETASILKNASKNSLIIVDELGRGTSTYDGFGLAWA  784

HUMAN  IAEHIASKIGAFALFATHFHELTALAEQLPTVNNLHVVALITKNLKEQKHDDETLTLLYQVEKGVSDQSFGIHVAEVANFPEKVVECAKQKALELDDLQY
              810       820       830       840       850       860       870       880       890       900
HUMAN  ISEYIATKIGAFCMFATHFHELTALANQIPTVNNLHVTALTT------EETLTMLYQVKKGVCDQSFGIHVAELANFPKHVIECAKQKALELEEFQY     856
YEAST  IAEHIASKIGCFALFATHFHELTELSEKLPNVKNMHVVAHIEKNLKEQKHDDEDITLLYKVEPGISDQSFGIHVAEVVQFPEKIVRMAKRKANELDDLK-  884

HUMAN  IGESEGLDIAELAAQEVNLGNIQGEALLQEFLSKVKEEGLHDPSKITTEASEENITILLKALAAEVIAENDSFVEEIISKIKVTTX
              910       920       930       940       950       960       970       980
HUMAN  IGESQGYDIMEPAAKKCYLEREQGEKIIQEFLSKVKQMPF------TEMSEENITIKLKQLKAEVIAKNNSFVNEIISRIKVTT                  935
YEAST  -TNNEDLKKAKLSLQEVNEGNIRLKALLKEWIRKVKEEGLHDPSKITEEASQHKIQELLRAIANEPEKENDNYLE--IYKSPCCYN              966
```

FIG. 3B

```
HUMAN  MSLVAGVIKALDASVVNKIAAGEVIISPANALKEMIENSLDANATSIDVLVKEGGLKVLQITDNGSGINKADLDIVCERFTTSKLQSFEDLASISTYGFR  100
YEAST  MSFVAGVIRRLDETVVNRIAAGEVIQRPANAIKEMIENCLDAKSTSIQVIVKEGGLKLIQIQDNGTGIRKEDLDIVCERFTTSKLQSFEDLASISTYGFR  100
       MSLR---IKALDASVVNKIAAGEIIISPVNALKEMMENSIDANATMIDILVKEGGIKVLQITDNGSGINKADLPILCERFTTSKLQKFEDLSQIQTYGFR   97
                10        20        30        40        50        60        70        80        90       100

HUMAN  GEALASISHVAHVTVTTKVADGKCAYRASYADGKLLASPKPVAGNDGTTILVEDLFFNIASRLKALKSHSDEYGKILDVGRYAVHSAGIGFSVKKQGDS  200
YEAST  GEALASISHVAHVTITTKTADGKCAYRASYSDGKLKAPPKPCAGNQGTQITVEDLFYNIATRRKALKNPSEEYGKILEVVGRYSVHNAGISFSVKKQGET  200
       GEALASISHVARVTVTTKVKEDRCAMRVSYAEGKMLESPKPVAGKDGTTILVEDLFFNIPSRLRALRSHNDEYSKILDVVGRYAIHSKDIGFSCKKFGDS  197
               110       120       130       140       150       160       170       180       190       200

HUMAN  VASVSVLPSASVVDNIRSVFGNAVASELITIGISDVETLALESVDGKVSNANFIVKKSISLLLFINNRLVTSTLLRKALESVYAAYLPKGTHPFLYLGLV  300
YEAST  VADVRTLPNASTVDNIRSIFGNAVSRELIEIGCED-KTLAFK-MNGYISNANYSVKKCI-FLLFINHRLVESTSLRKAIETVYAAYLPKNTHPFLYLSLE  297
       NYSLSVKPSYTVQDRIRTVFNKSVASNLITFHISKVEDLNLESVDGKVCNLNFISKKSISLIFFINNRLVTCDLLRRALNSVYSNYLPKGFRPFIYLGIV  297
               210       220       230       240       250       260       270       280       290       300

HUMAN  ISPAAVDVNVHPTKHEVHFLSEDSILEKVANQLEAELLGIDSSRITFKASSLLTGLAGSLIPSGDTVESTTSLTSLSTAGVVDNVYATANSQLRKAKRQEN  400
YEAST  ---------------------------------PSGEMVKSTTSLTSSSTSGSSDKVYA------------H  381
       IDPAAVDVNVHPTKHEVHFLSQDEIIEKIANQLHAELSAIDTSRTFKASSISTNKPESLIPFNDTIESDRNRKSLRQAQVVENSYTTANSQLRKAKRQEN  397
               310       320       330       340       350       360       370       380       390       400

HUMAN  QLVRIDASEAKLTAFLSSLSQQLSSEGSAIVTELSTDIVSGVAHSQDAEKLTLNAPAEVAAKNQSLEGDTTKGASTISDNRGDLSSNPKKQKLGDSDVE  500
YEAST  QMVRTDSREQKLDAFLQPLSKPLSSQPQAIVTEDKTDISSGRARQODEEMLELPAPAEVAAKNQSLEGDTTKGTSEMSEKRGPTSSNPRKRHR-EDSDVE  480
       KLVRIDASQAKITSFLSS--SQQFNEGSSTKRQLSEPKVTNVSHSQEAEKLTLN-----------------ESEQPRDANTINDN--DLKDQPKKKQKLGDYKVP  482
               410       420       430       440       450       460       470       480       490       500

HUMAN  SVADDSKNALTAAKDGYIRVPKERVNWLTSVLSQEEVDDSGHEVLTDILANLSFVGVVDEERALAAIQHDLKLFLLDTGSVSEELFYQIGLTDFANFG  600
YEAST  QMVRTDSREQKLDAFL---QHQTKLYLLNTTKLSEELFYQILIYDFANFG  572
       KLVRIDASQAKITSFLSS---QHQTKLYLLNTTKLSEELFYQILIYDFANFG  582
               510       520       530       540       550       560       570       580       590       600

HUMAN  MVEDDSRKEMTAA------CTPRRRI-INLTSVLSLQEEINEQGHEVLREMLHNHSFVGCVNPQWALA--QHQTKLYLLNTTKLSEELFYQILIYDFANFG  664
YEAST  SIADDEKNALPISKDGYIRVPKERVNVNLTSIKKLREKVDDSIHRELTDIFANLNYVGVVDEERRLAAIQHDLKLFLIDYGSVCYELFYQIGLTDFANFG  677
       VLNLSSTAVLDDLALLALDLSESGELEDDGSKEGLAEYIVSKLKDKASMLADYFSLELVEDGLDNDLKSVNLIGLPLLDGYVPSLVGLPIFILRLGTEV   700
               610       620       630       640       650       660       670       680       690       700

HUMAN  VLRLSEPAPLFDLAMLALDSPESGWTEEDGPKEGLAEYIVEFLKKKAEMLADYFSLEIDEEG------NLIGLPLLIDNYVPPLEGLPIFILRLATEV  756
YEAST  KINLQSTNVSDDIVLYNL-LSEFDELNDDASKEK----IISKIWDMSSMLNEYYSIELVNDGLDNDLKSVKLKSLPLLLKGYIPSLVKLPFFIYRLGKEV  769
       DWDDEQECLDGLLKEIALLYIPSIVKQVISLDASLSGDESAVFGSIKESISSLVEHVVFKALKSHILAPKHILEDGNVVELANLPDLYKVFERC         790
               710       720       730       740       750       760       770       780       790

HUMAN  NWDEEKECFESLSKECAMFY--SIRKQYISEESTLSGQQSEVPGSIPNSWKMTVEHIVYKALRSHILPPKHFTEDGNILQLANLPDLYKVFERC
YEAST  DWEDEQECLDGILREIALLYIPDMVPKVDTLDASLSEDEKAQFINRKEHISSLLEHVLFPCIKRRFLAPRHILKD--VVEIANLPDLYKVFERC
```

FIG. 4

METHOD FOR DETECTION OF ALTERATIONS IN THE DNA MISMATCH REPAIR PATHWAY

This application is a continuation-in-part application of U.S. patent application Ser. No. 08/259,310, filed on Jun. 13, 1994, now abandoned, which is a continuation-in-part application of U.S. patent application Ser. No. 08/163,449, filed on Dec. 7, 1993, now abandoned, which is a continuation-in-part of patent application Ser. No. 08/154,792, filed Nov. 17, 1993, now abandoned.

The work described herein was supported, in part, by National Institutes of Health grants HG00305 (now numbered GM60005), CA56542, and a National Institute of Health Cancer Center Core Grant CA06516 to the Dana-Farber Cancer Institute. The U.S. Government has certain rights to this invention.

FIELD OF THE INVENTION

The present invention pertains to a eukaryotic DNA mismatch repair pathway, the genes involved, and uses thereof, for example, in drug screening, cancer prognosis and diagnosis. More specifically, the invention relates to detection of alterations in the DNA mismatch repair pathway associated with some human cancers, such as colon cancer.

BACKGROUND OF THE INVENTION

Accurate transmission of genetic information is important in the survival of a cell, an organism, and a species. A number of mechanisms have evolved that help to ensure high fidelity transmission of genetic material from one generation to the next since mutations can lead to new genotypes that may be deleterious to the cell. DNA lesions that frequently lead to mutations are modified, missing or mismatched nucleotides. Multiple enzymatic pathways have been described in prokaryotic systems that can specifically repair these lesions.

There are at least three ways in which mismatched nucleotides arise in DNA. First, physical damage to the DNA or DNA precursors can give rise to mismatched bases in DNA. For example, the deamination of 5-methyl-cytosine creates a thymine and, therefore, a G-T mispair. Second, misincorporation, insertion, or deletion of nucleotides during DNA replication can yield mismatched base pairs. Finally, genetic recombination produces regions of heteroduplex DNA which may contain mismatched nucleotides when such heteroduplexes result from the pairing of two different parental DNA sequences. Mismatched nucleotides produced by each of these mechanisms are known to be repaired by specific enzyme systems.

The well defined mismatch repair pathway is the *E. coli* MutHLS pathway that promotes a long-patch (approximately 3 Kb) excision repair reaction which is dependent on the mutH, mutL, mutS and MutU(uvrD) gene products. The MutHLS pathway appears to be the most active mismatch repair pathway in *E. coli* and is known to both increase the fidelity of DNA replication and act on recombination intermediates containing mispaired bases. This system has been reconstituted in vitro and requires the MutH, MutL, MutS and UvrD (helicase II) proteins along with DNA polymerase III holoenzyme, DNA ligase, single-stranded DNA binding protein (SSB) and one of the single-stranded DNA exonucleases, Exo I, Exo VII or RecJ. MutS protein binds to the mismatched nucleotides in DNA. MutH protein interacts with GATC sites in DNA that are hemi-methylated on the A and is responsible for incision on the unmethylated strand. Specific excision of the unmethylated strand results in increased fidelity of replication because excision is targeted to the newly replicated unmethylated DNA strand. MutL facilitates the interaction between MutS bound to the mismatch and MutH bound to the hemi-methylated Dam site resulting in the activation of MutH. UvrD is the helicase that appears to act in conjunction with one of the single-stranded DNA specific exonucleases to excise the unmethylated strand leaving a gap which is repaired by the action of DNA polymerase III holoenzyme, SSB and DNA ligase. In addition, *E. coli* contains several short patch repair pathways including the VSP system and the MutY (MicA) system that act on specific single base mispairs.

In bacteria, therefore, mismatch repair plays a role in maintaining the genetic stability of DNA. The bacterial MutHLS system has been found to prevent genetic recombination between the divergent DNA sequences of related species such as *E. coli* and *S. typhimurium* (termed: homeologous recombination).

The existence of prokaryotic mismatch repair systems that function to maintain genetic DNA stability is of particular interest since different types of human tumors show an instability of repeated DNA sequences. For example, Hereditary Non-Polyposis Colon Cancer (HNPCC), a familiar form of human colorectal cancer (CRC) that is also known as Lynch's Syndrome appears to be linked to a locus causing such genetic instability.

CRC is one of the most common forms of neoplasia in industrial countries and the possibility of a heritable component to CRC has been much debated. A high incidence of CRC within families has been well documented (approximately 13% of CRC cases are categorized as familial), but there is uncertainty over whether this effect results from common exposure to environmental influences such as diet, which have been shown to play a role in CRC risk, or from the influence of a genetic factor(s).

Recently, genetic linkage has been demonstrated between anonymous microsatellite markers on human chromosome 2 and the incidence of HNPCC. HNPCC is defined by the existence of at least three family members with CRC in at least two successive generations, with at least one affected member having been diagnosed at less than 50 years of age. A study of two independent HNPCC kindreds demonstrated the linkage with chromosome 2 markers, firmly supporting the view that there is a genetic component to HNPCC and suggesting that an unknown gene on chromosome 2 can play a role in conferring HNPCC susceptibility (Peltomaki et al., Science 260: 810, 1993, the contents of which are incorporated herein by reference). A further study of 14 smaller HNPCC kindreds also suggested a link between HNPCC and a gene on chromosome 2, although in this second study, the incidence of disease was not linked to markers on chromosome 2 in all families (Aaltonen et al. Science 260: 812, 1993).

Molecular analyses of HNPCC tumors have provided some information about likely characteristics of a gene responsible for conferring susceptibility to HNPCC. In particular, studies have revealed genomic instability of short repeated DNA sequences in HNPCC tumor tissues (Aaltonen et al., id; Thibodeau et al., Science 260: 816, 1993). The data also suggest that this tendency toward genomic instability can be inherited and may be related to mutation in a gene located on human chromosome 2. The idea that the mutation responsible for a genetic predisposition to HNPCC also leads to genomic instability of short repeated sequences is consistent with the observation that members of HNPCC kindreds show susceptibility to other cancers as well and often develop tumors outside the colorectal epithelium (e.g. in breast, ovary, bladder, endometrial (uterine), renal, skin or rectal). A full understanding of the relationship between mutation, genomic instability, and tumor development requires that the relevant genes be cloned and sequenced.

The problem is that cloning of genes involved in cancer development has proven difficult. In HNPCC, for example, even with the knowledge that there is a genetic linkage between the disease and markers on chromosome 2, the identification of the gene is unpredictable since the identified markers could be on the order of 9 million base pairs away from the gene of interest. (Peltomaki et al., supra; Marx, Science 260: 751, 1993). The additional observation of genomic instability in HNPCC tumor tissues further complicates identification of that gene.

Even with the present information on prokaryotic mismatch genes and the observation that the products of DNA mismatch repair genes might be involved in genomic instability, it is not clear how to identify eukaryotic homologues of a prokaryotic mismatch repair gene.

SUMMARY OF THE INVENTION

We have now discovered that eukaryotes, including mammals, have a DNA mismatch repair pathway analogous to the pathway that exists in bacteria. Defects or alterations in this mismatch repair pathway in a mammal will result in the accumulation of unstable repeated DNA sequences. Such a phenotype has a high correlation to disease state in a number of cancers, such as hereditary colon cancers. Accordingly, discovering defect or alteration in the pathway can be diagnostic of a predisposition to cancer, and prognostic for a particular cancer.

We have also discovered and sequenced one of the genes in this pathway in a number of mammals, including humans. This gene, referred to herein as MSH2, as will be discussed below, has many applications. It can be used in assays, to express gene product, for drug screens, and therapeutically.

We also disclose a method for screening for other genes in this mismatch repair pathway.

| Internal Malignancies | Skin Tumours |
|---|---|
| Bl = Bladder | BCC = Basal Cell Carcinoma |
| CLL = Chronic Lympatic Leukemia | KA = Keratoacanthoma |
| Cx = Cervix | SA = Sabaceous Adenoma |
| CRC = Colorectal | SE = Sabaceous Epithelioma |
| FAP = Famalial Adenomatous Polyposis | SH = Sabaceous Hyperplasia |
| L = Lung | Bo = Bowen's Disease |
| Sa = Sarcoma Bone | |
| SB = Small Bowel | |
| St = Stomach | |
| Ur = Ureter | |
| Ut = Uterus | |

Figure 1:
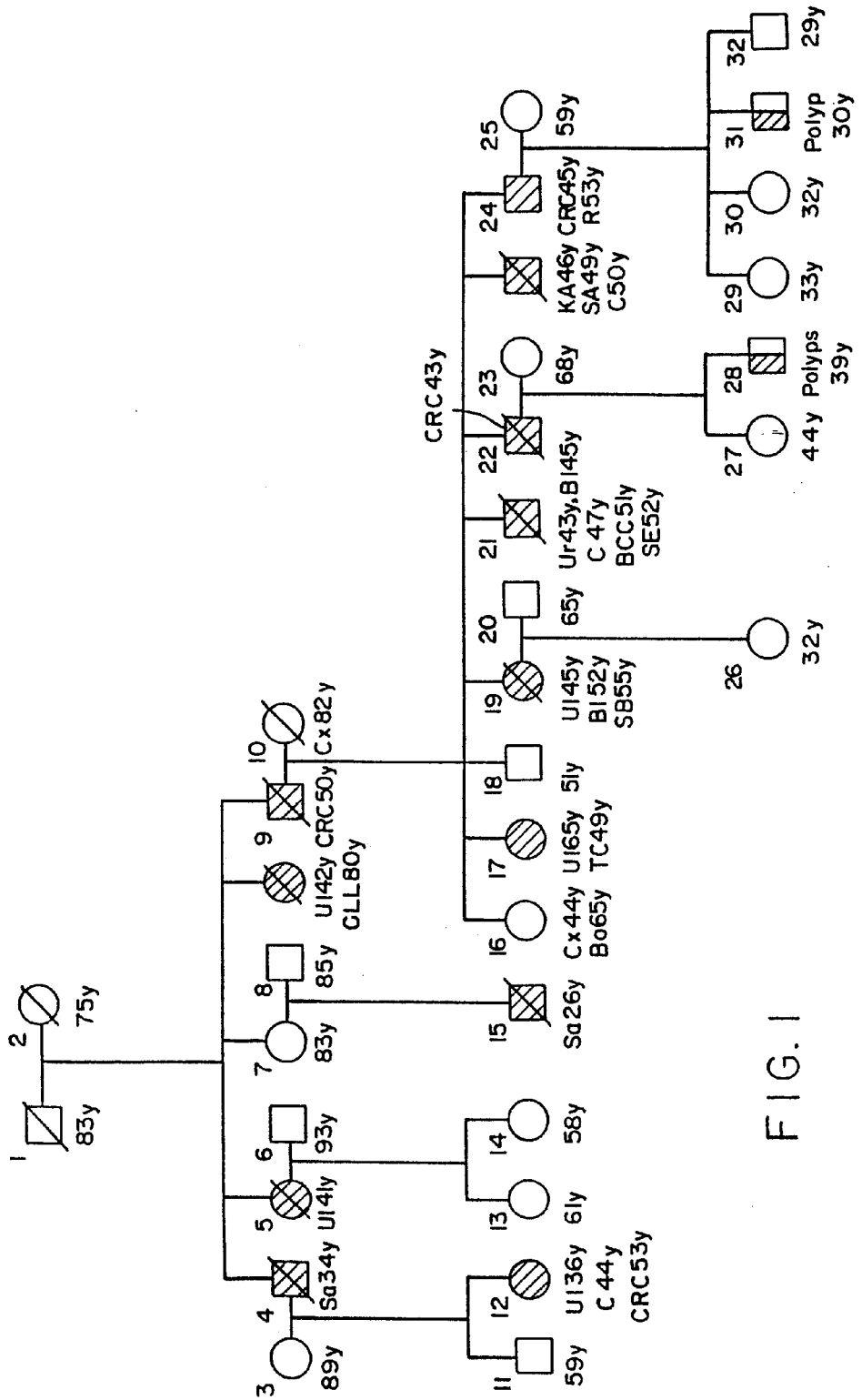
FIG. 1 presents the lineage of an extended Muir-Torre HNPCC kindred.
Figure 2:
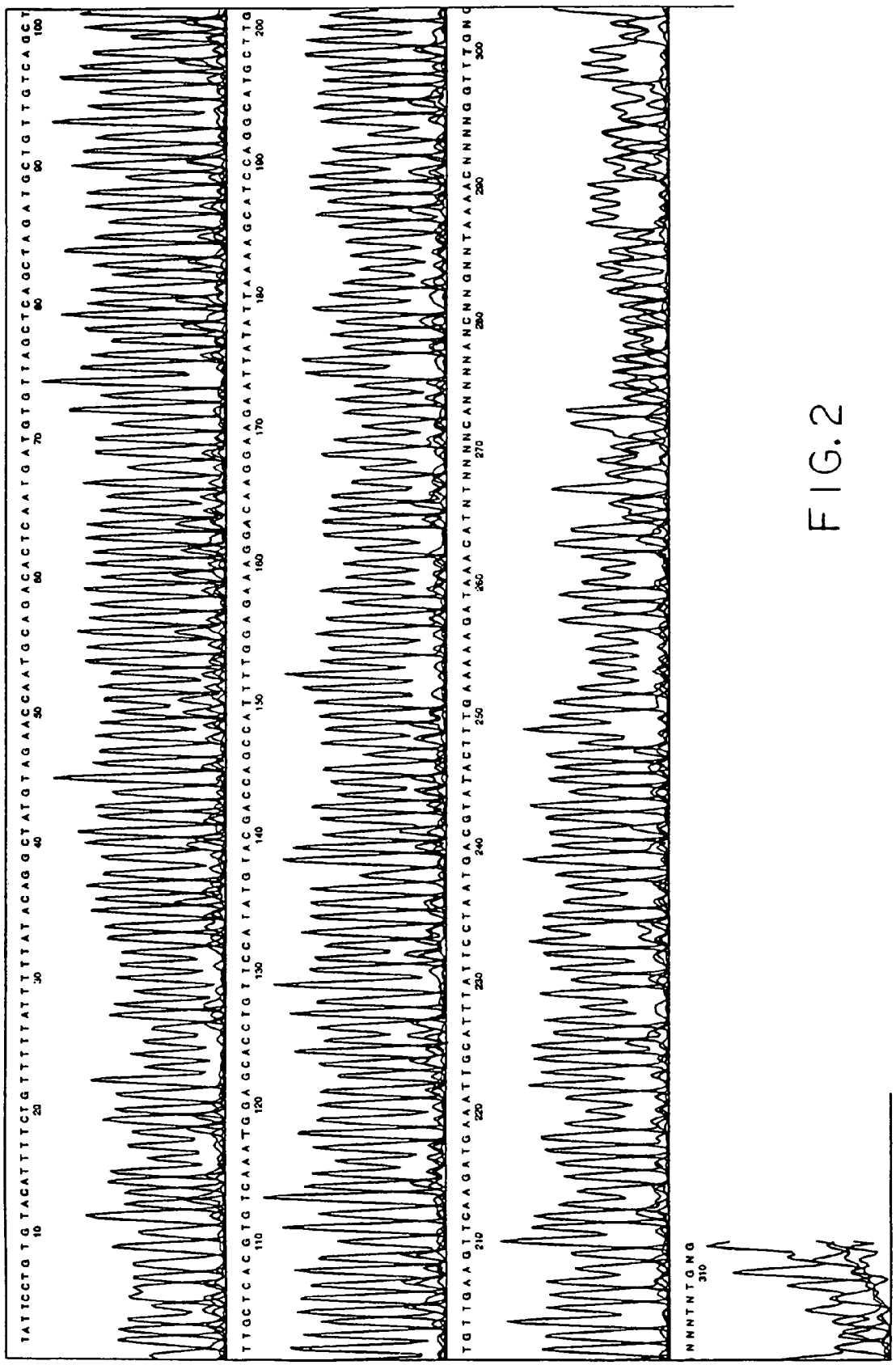

FIG. 2 presents sequence chromatograms that reveal an hMSH2 mutation that is inherited in the HNPCC kindred of FIG. 1.

FIGS. 3A and 3B present an alignment of human and yeast Msh2 protein sequences.

FIG. 4 presents an alignment of human and yeast Mlh1 protein sequences.

Figure 5:
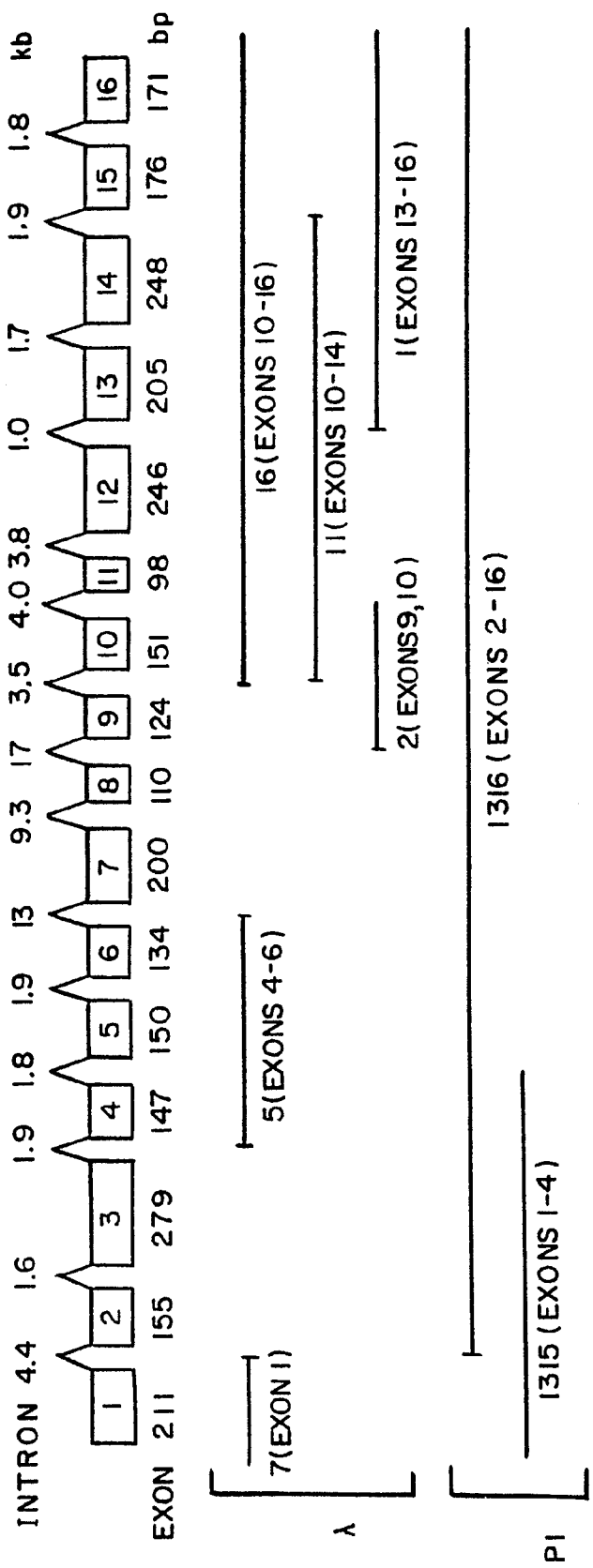

FIG. 5 presents a diagram of the organization of the MSH2 locus and MSH2 containing genomic clones. The boxes containing the numbers 1 to 16 represent the individual MSH2 exons. The size of each exon is given below each exon, and the size of each intron is given above the region between individual pairs of exons. The lines below the gene represent each of the individual λ and P1 clones obtained. Each clone is labeled with an identification number and the identification number of each exon contained in the clone. The presence of the indicated exons was determined either by direct sequence analysis or by PCR with the exon-specific primers, using each clone as template.

DESCRIPTION OF THE SEQUENCE LISTING

SEQ ID NO.:1 is the nucleotide sequence of the yeast MSH2 gene.

SEQ ID NO.:2 is the nucleotide sequence of the yeast MSH1 gene.

SEQ ID NO.:3 is the amino acid sequence of the yeast MSH2 protein.

SEQ ID NO.:4 is the amino acid sequence of the yeast MSH1 protein.

SEQ ID NO.:5 is the amino acid sequence of the peptide TGPNM.

SEQ ID NO.:6 is the amino acid sequence of peptide FATHF.

SEQ ID NO.:7 is an amino acid sequence of peptide FATHY.

SEQ ID NO.:8 is a nucleotide sequence for a human cDNA clone that is a homologue of the E. coli mutS mismatch repair gene.

SEQ ID NO.: 10 is the nucleotide sequence of a mouse nucleotide sequence that is homologous to the E. coli mutS mismatch repair gene.

SEQ ID NO.:11 is a degenerate oligonucleotide pool including sequences capable of encoding TGPNM, including a BamHI restriction site.

SEQ ID NO.:12 is a degenerate oligonucleotide pool directed to sequences encoding F(A/V) THY, including a BamHI restriction site.

SEQ ID NO.: 13 is a degenerate oligonucleotide pool directed to sequences capable of encoding FATH(F/Y).

SEQ ID NO.:14 is a degenerate oligonucleotide pool directed to sequences capable of encoding FTTH(F/Y).

SEQ ID NO.:15 is the nucleotide sequence of PCR clone 22.1.

SEQ ID NO.:16 is the amino acid sequence of the human protein encoded by SEQ ID NO.:8.

SEQ ID NOS.:17/18 are a set of oligonucleotides that, when used as primers in a PCR reaction, can amplify an ~85 bp fragment of a eukaryotic nucleotide sequence that is a homologue of an E. coli mutS mismatch repair gene. These primers include a BamHI restriction site.

SEQ ID NO.:19 is the nucleotide sequence of the PCR clone MS351-I.

SEQ ID NO.:20 is the nucleotide sequence of the PCR clone MS351-II.

SEQ ID NOS.:21/22 are a set of oligonucleotides that, when used as primers in a PCR reaction, can amplify an ~158 bp intronic fragment from a genomic human homologue of a mutS mismatch repair gene (MSH2$_{hu}$).

SEQ ID NO.:23 is an oligonucleotide primer that, when used in a PCR reaction with the primer of SEQ ID NO.:17, amplifies a 278 bp fragment found in SEQ ID NO.:8.

SEQ ID NOS.:25/26, 29/30, 31/32, 33/34, 35/36, 37/38 and 39/40: are sets of oligonucleotides that, when used as primers in PCR reactions, can amplify exon sequences from MSH2$_{hu}$.

SEQ ID NO.:27 is the yeast protein of SEQ ID No.:4, including a I2CA5 epitope tag between amino acids 21 and 22.

SEQ ID NO.:28 is a degenerate oligonucleotide pool directed to sequences capable of encoding FVTH (F/Y).

SEQ ID NO.:41 is the degenerate nucleotide sequence that encodes peptide SEQ ID NO.:6.

SEQ ID NO.:42 is the degenerate nucleotide sequence that encodes peptide SEQ ID NO:7.

SEQ ID NO.:43 is the nucleotide sequence of the E. coli mutS gene as found in GenBank (accession number M64730).

SEQ ID NO.:44 is amino acid sequence of the E. coli MutS protein, which sequence is deduced from the nucleotide sequence of SEQ ID NO.:43.

SEQ ID NO.: 45 is a cDNA sequence of the human MSH2 gene, hMSH2.

SEQ ID NOs.: 46-65 are primers that can be used to amplify individual exons of the hMSH2 gene.

SEQ ID NOs.: 66-81 are the individual exons of the hMSH2 gene.

SEQ ID NOs.: 82-113 are confirmed non-exonic hMSH2 genomic sequences.

SEQ ID NOs.: 157 and 114-144 are SEQ ID NOs.: 82-113, respectively, along with additional, non-confirmed non-exonic hMSH2 genomic sequence.

SEQ ID NOs.: 145 and 146 are a set of primers used for PCR screening of a P1 phage library to identify hMSH2 genomic clones.

SEQ ID NOs.: 147/148-153/154 are a set of primers that are "nested" relative to the primers of SEQ ID NOs.: 62/63-64/32, respectively, and can be used with the primers of SEQ ID NOs.: 62/63-64/32, respectively in a multiplex PCR protocol such as the one set forth in Example 9.

SEQ ID NO.: 155 is the cDNA sequence of the human MLH1 gene, hMLH1.

SEQ ID NO.: 156 is the amino acid sequence of the hMlh1 protein encoded by SEQ ID NO.: 155.

DETAILED DESCRIPTION OF THE INVENTION

We have now discovered that eukaryotes, including mammals, have a DNA mismatch repair pathway analogous to the pathway that exists in bacteria. Defects or alterations in this mismatch repair pathway in a mammal will, such as a human, result in the accumulation of unstable repeated DNA sequences. Such a phenotype has a high correlation to disease state in a number of cancers, such as hereditary colon cancers. Accordingly, discovering a defect or alteration or defect in the pathway can be diagnostic of a predisposition to cancer, and prognostic for a particular cancer.

The diagnostic and prognostic methods of the present invention include looking for an alteration in an element of a eukaryotic mismatch repair pathway. Preferably, the eukaryotic mismatch repair pathway is mammalian, most preferably human. The alteration may be due to a deletion, addition and/or mutation, such as a point mutation, in a gene that is a member of the pathway. Any of these types of mutations can lead to non-functional mismatch repair pathway gene products. The mutational events may occur not only in an exon, but also in an intron or non-exonic region. As a result of alterations of this kind, including alterations in non-exonic regions, effects can be seen in transcription and translation of members of the pathway, thereby affecting the ability to repair mismatch errors. The changes resulting from these alterations are also reflected in the resultant protein and mRNA as well as the gene. Other alterations that might exist in the pathway include changes that result in an increase or decrease in expression of a gene in the mismatch repair pathway.

Consequently, one aspect of this invention involves determining whether there is an alteration of at least one element in the mismatch repair pathway. This determination can involve screening for alterations in the genes involved in the pathway, their mRNA, their gene products, or by detecting other manifestations of defects in the pathway. Alterations can be detected by screening for a particular mismatch repair element in a suitable sample obtained, for example, from tissue, human biological fluid, such as blood, serum, plasma, urine, cerebrospinal fluid, supernatant from normal cell lysate, supernatant from preneoplastic cell lysate, supernatant from neoplastic cell lysate, supernatants from carcinoma cell lines maintained in tissue culture, eukaryotic cells, etc.

In order to detect alterations in the mismatch repair pathway from tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. It is then helpful to screen normal tissue free from malignant tissue. Then comparisons can be made to determine whether a malignancy results from a spontaneous change in the mismatch repair pathway or is genetic.

Detection of mutations may be accomplished by molecular cloning of those mismatch repair genes present in the tumor tissue and sequencing the genes using techniques well known in the art. For example, mRNA can be isolated, reverse transcribed and the cDNA sequenced. Alternatively, the polymerase chain reaction can be used to amplify mismatch repair pathway genes or fragments thereof directly from a genomic DNA preparation from the tumor tissue. The DNA sequence of the amplified sequences can then be determined. Alternatively, one can screen for marker portions of the DNA that are indicative of changes in the DNA. The polymerase chain reaction itself is well known in the art. See e.g., Saiki et al., Science, 239:487 (1988); U.S. Pat. No. 4,683,203; and U.S. Pat. No. 4,683,195. Specific primers which can be used in order to amplify the mismatched repair genes will be discussed in more detail below.

Specific deletions of mismatch repair pathway genes can also be detected. For example, restriction fragment length polymorphism (RFLP) probes for the mismatch repair genes, such as MSH2, can be used to score loss of a wild-type allele. Other techniques for detecting deletions, as are known in the art, can be used.

Loss of wild-type mismatch repair pathway genes may also be detected on the basis of the loss of a wild-type expression product of the mismatch repair pathway genes. Such expression products include both the mRNA as well as the protein product itself. Point mutations may be detected by sequencing the mRNA directly or via molecular cloning of cDNA made from the mRNA. The sequence of the cloned cDNA can be determined using DNA sequencing techniques which are well known in the art. Alternatively, one can screen for changes in the protein. For example, a panel of antibodies, for example single chain or monoclonal antibodies, could be used in which specific epitopes involved in, for example, MSH2 functions are represented by a particular antibody.

Loss or perturbation of binding of a monoclonal antibody in the panel would indicate mutational alteration of the protein and thus of the gene itself. Alternatively, deletional mutations leading to expression of truncated proteins can be quickly detected using a sandwich type ELISA screening procedure, in which, for example, the capture antibody is specific for the N-terminal portion of the pathway protein. Failure of a labeled antibody to bind to the C-terminal portion of the protein provides an indication that the protein is truncated. Even where there is binding to the C-terminal, further tests on the protein can indicate changes. For example, molecular weight comparison. Any means for detecting altered mismatch repair pathway proteins can be used to detect loss of wild-type mismatch repair pathway genes.

Alternatively, mismatch detection can be used to detect point mutations in the mismatch repair pathway genes or their mRNA product. While these techniques are less sensitive than sequencing, they can be simpler to perform on a large number of tumors. An example of a mismatch cleavage technique is the RNAase protection method, which is described in detail in Winter et al., Proc. Natl. Acad. Sci. USA, 82:7575 (1985) and Meyers et al., Science, 230:1242 (1985). In the practice of the present invention, the method involves the use of a labeled riboprobe which is complementary to the human wild-type mismatch repair pathway genes. The riboprobe and either mRNA or DNA-isolated form the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mismatch repair pathway mRNA or DNA. The riboprobe comprises only a segment of the mismatch repair pathway mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Nat. Acad. Sci. USA, 85:4397 (1988); and Shenk et al., Proc. Natl. Acad. Sci. USA, 72:989 (1975). Alternatively, mismatches can be detected by shifts in the electrophoretic mobility of mismatched duplexes relative to matched duplexes. See, e.g., Cariello, Human Genetics, 42:726 (1988). With either riboprobes or DNA probes, the cellular mRNA or DNA which might contain a mutation can be amplified using PCR before hybridization.

DNA sequences of the mismatch repair pathway genes from tumor tissue which have been amplified by use of polymerase chain reaction may also be screened using allele-specific probes. These probes are nucleic acid oligomers, each of which contains a region of a mismatch repair pathway gene sequence harboring a known mutation. By use of a battery of allele-specific probes, the PCR amplification products can be screened to identify the presence of a previously identified mutation in the mismatch repair pathway genes. Hybridization of allele-specific probes with amplified mismatch repair pathway sequences can be performed, for example, on a nylon filter. Hybridization to a particular probe indicates the presence of the same mutation in the tumor tissue as in the allele-specific probe.

Altered mismatch repair pathway genes or gene products can be detected in a wide range of biological samples, such as serum, stool, or other body fluids, such as urine and sputum. The same techniques discussed above can be applied to all biological samples. By screening such biological samples, a simple early diagnosis can be achieved for many types of cancers. Even when someone has been diagnosed with cancer, these screens can be prognostic of the condition, e.g., spontaneous mutation versus hereditary. The prognostic method of the present invention is useful for clinicians so that they can decide upon an appropriate course of treatment. For example, a hereditary mutation in the DNA mismatch repair system suggests a different therapeutic regimen than a sporadic mutation.

The methods of screening of the present invention are applicable to any sample in which defects in the mismatch repair pathway has a role, such as in tumorigenesis.

The method of the present invention for diagnosis of a DNA mismatch repair defective tumor is applicable across a broad range of tumors. These include colorectal, ovary, endometrial (uterine), renal, bladder, skin, rectal and small bowel.

The present invention also provides a kit useful for determination of the nucleotide sequence of a mismatch repair gene using a method of DNA amplification, e.g., the polymerase chain reaction. The kit comprises a set of pairs of single stranded oligonucleotide DNA primers which can be annealed to sequences within or surrounding the mismatch repair gene in order to prime amplifying DNA synthesis of the gene itself.

In order to facilitate subsequence cloning of amplified sequences, primers may have restriction enzyme sites appended to their 5' ends. Thus, all nucleotides of the primers are derived from the mismatch repair gene sequences or sequences adjacent thereto except the few nucleotides necessary to form a restriction enzyme site. Such enzymes and sites are well known in the art. The primers themselves can be synthesized using techniques which are well known in the art. Generally, the primers can be made using synthesizing machines which are commercially available.

In a preferred embodiment, the set of primer pairs for detecting alterations in the hMSH2 gene comprises primer pairs selected from the group consisting of SEQ ID Nos:46-65 and 145-154.

According to the present invention, a method is also provided of supplying wild-type mismatch repair pathway function to a cell which carries mutant mismatch repair pathway alleles. The wild-type mismatch repair pathway gene or a part of the gene may be introduced into the cell in a vector such that the gene remains extrachromosomal. In such a situation, the gene will be expressed by the cell from the extrachromosomal location. If a gene portion is introduced and expressed in a cell carrying a mutant mismatch repair pathway allele, the gene portion should encode a part of the mismatch repair pathway protein which is required for mismatch repair in that cell. More preferred is the situation where the wild-type mismatch repair pathway gene or a part of it is introduced into the mutant cell in such a way that it recombines with the endogenous mutant mismatch repair pathway gene present in the cell. Such recombination would require stable integration into the cell such as via a double recombination event which would result in the correction of the mismatch repair pathway gene mutation. Vectors for introduction of genes both for recombination and for extrachromosomal maintenance are known in the art and any suitable vector may be used. Such a cell can be used in a wide range of activities. For example, one can prepare a drug screen using a tumor cell line having a defect in the mismatch repair pathway and by this technique create a control cell from that tumor cell. Thus, one can determine if the compounds tested affect the pathway. Such a method can be used to select drugs that specifically affect the pathway or as a screen for agents, including known anticancer agents, that are effective against mismatch repair defective tumors. These drugs may be combined with other drugs for their combined or synergistic effects. In contrast, when comparing normal cells with neoplastic cells there can be a variety of factors affecting such cells, thus, such a comparison does not provide the same data. These cells may also be able to be used therapeutically, for example, in somatic cell therapy, etc.

The present invention further provides a method for determining whether an alteration in a pathway gene is a mutation or an allelic variation. The method comprises introducing the altered gene into a cell having a mutation in the pathway gene being tested. The cell may be in vitro or in vivo. If the altered gene tested is an allelic variation, i.e., function is maintained, the mutation will be complemented and the cell will exhibit a wild-type phenotype. In contrast, if the altered gene in a mutation, the mutation will not be complemented and the cell will continue to exhibit non-wild type phenotype.

One can also prepare cell lines stably expressing a member of the pathway. Such cells can be used for a variety of purposes including an excellent source of antigen for preparing a range of antibodies using techniques well known in the art.

Polypeptides or other molecules which have mismatch repair pathway activity may be supplied to cells which carry mutant mismatch repair pathway alleles. The active molecules can be introduced into the cells by microinjection or by liposomes, for example. Alternatively, some such active molecules may be taken up by the cells, actively or by diffusion. Supply of such active molecules will effect an earlier neoplastic state.

Predisposition to cancers can be ascertained by testing normal tissues of humans. For example, a person who has inherited a germline mismatch repair pathway alteration would be prone to develop cancers. This can be determined by testing DNA or mRNA from any tissue of the person's body. Most simply, blood can be drawn and the DNA or mRNA extracted from cells of the blood. Loss of a wild-type mismatch repair pathway allele, either by point mutation, addition or by deletion, can be detected by any of the means discussed above. Nucleic acid can also be extracted and tested from fetal tissues for this purpose.

Accordingly, the present invention provides for a wide range of assays (both in vivo and in vitro). These assays can be used to detect cellular activities of the members in the mismatch repair, which include eukaryotic nucleotide sequences that are homologous to bacterial mismatch repair genes and the cellular activities of the polypeptides they encode. In these assay systems, mismatch repair genes, polypeptides, unique fragments, or functional equivalents thereof, may be supplied to the system or produced within the system. For example, such assays could be used to determine whether there is a mismatch repair gene excess or depletion. For example, an in vivo assay systems may be used to study the effects of increased or decreased levels of transcript or polypeptides of the invention in cell or tissue cultures, in whole animals, or in particular cells or tissues within whole animals or tissue culture systems, or over specified time intervals (including during embryogenesis).

Another aspect of the invention relates to isolated DNA segments which hybridize under stringent conditions to a DNA fragment having the nucleotide sequence set forth in SEQ ID NO:8 or a unique fragment thereof and codes for a member of a eukaryotic DNA mismatch repair pathway. Stringent hybridization conditions are well known to the skilled artisan. For example, the hybridization conditions set forth in Example 1 can be used.

Identification and Classification of Tumors.

One preferred assay described herein permits the diagnosis and/or prognosis of mismatch repair defective tumors. The eukaryotic nucleotide sequences, polypeptides, and antibodies of this invention are particularly useful for determining pathological conditions suspected of being tumors that: (i) contain a non-wild type allele of a nucleotide sequence that is homologous to a member of the analogous bacterial mismatch repair pathway, e.g. a bacterial mismatch repair gene and/or (ii) lack at least one antigenic determinant on a polypeptide that is encoded by a nucleotide sequence that is homologous to a bacterial mismatch repair gene, and/or contain new antigenic determinants.

Using any technique known in the art including, for example, Southern blotting, Northern blotting, PCR, etc. (see, for example, Grompe, Nature Genetics 5:111-117, 1993, incorporated herein by reference) the nucleotide sequences of the present invention can be used to identify the presence of non-wild type alleles of sequences that are homologous to a bacterial mismatch repair gene in nucleic acid that has been isolated from tumors.

For example, in one embodiment, using SEQ ID NO.: 8, PCR primers can be designed to amplify individual exons or introns of human HMS2, which is a homologue of the E. coli mutS gene. These primers can then be used to identify and classify human tumors that contain at least one non-wild type allele of at least one sequence of the human gene corresponding to SEQ ID No.:8. Exemplary primer sets listed in SEQ ID NOS.: 25/26, 29/30, 31/32, 35/36, 37/38 and 39/40 can be used to amplify the individual exon of the human HMS2 gene. These primers all hybridize to intron sequences, and thus can be used to amplify exons and their flanking intron/exon junctions, including sequences important for splicing, from nucleic acid that has been isolated from known tumor cells or cells suspected of being tumorous. The nucleotide sequences thus amplified can then be compared to the known, corresponding sequence to determine the presence or absence of any differences in the tumor sequences relative to wild type sequences. Tumors that contain at least one non-wild type allele of at least one sequence of the human gene can be classified as "mismatch repair defective". Comparisons of the sequences may be performed by direct sequence comparison or by other diagnostic methods known in the art including, but not limited to, single-strand conformational polymorphism analysis, denaturing polyacrylamide gel electrophoresis, and so on. (See, Grompe, supra.)

For instance, the primer set SEQ ID NOs.: 33/34 was used to amplify sequences from colorectal tumor DNA and from control non-tumor DNA by standard PCR technique. For example, using PCR reactions that contained 10 mM Tris buffer pH 8.5, 50 mM KCL, 3 mM $MgCl_2$, 0.01 gelatin, 50 µM each dNTP, 1.5 unit Taq DNA polymerase, 5 pmole each primer, and 25 ng template DNA (provided by Glen Steele, New England Deaconess Hospital, Boston, Mass. or J. Garber and F. Lee, Dana-Farber Cancer Institute, Boston, Mass.). 35 cycles of 30 sec at 94° C., 30 sec at 55° C., and 1 min at 72° C. were performed. Product bands were analyzed by the methods of Grompe supra. By such a method, differences were observed in the sequences amplified between tumor and non-tumor DNA. Alternatively, product bands can be sequenced using such oligonucleotides, e.g. SEQ ID NO.:33 and SEQ ID NO.:34. Thus, even a single-base-pair difference can be observed between tumor and non-tumor DNA samples. For example, the product band from normal tissue has the sequence 5'-C/CTACAAAAC-3', where "/" denotes an exon/intron boundary, whereas the product band from a tumor tissue in the same individual has the sequence 5'-C/

CTACAG̲AAC-3' (emphasis indicates altered base pair). This change is located within intron sequences that could to affect pre-mRNA splicing signals.

Other primer pairs can be used that amplify only intron sequences or only exon sequences. Product bands can be analyzed as described above.

Alternatively, the antibodies of the invention can be used as probes in standard techniques such as Western blotting to detect the absence in tumor tissues of at least one antigenic determinant on at least one eukaryotic polypeptide encoded by nucleotide sequences that are homologous to a bacterial mismatch repair gene and/or the presence of new antigenic determinants. Such cancers would be expected to contain mismatch repair defective tumors, as described above.

The present invention can also indicate other factors in cells having an alteration of a member of the pathway. For example, the information provided by the isolated eukaryotic nucleotide sequences and isolated polypeptides of the invention can be used to inactivate, in a host cell, an endogenous nucleotide sequence that is homologous to a bacterial mismatch repair gene and/or a polypeptide product encoded by an endogenous nucleotide sequence that is homologous to a bacterial mismatch repair gene. Physiological characteristics of the resultant altered host cell can be analyzed and compared to physiological characteristics of an unaltered host cell. Any physiological characteristics of the altered host cell that are different from those of the unaltered host cell can be noted. The same physiological characteristics can then be analyzed in tumor cells to help identify those tumors that contain a non-wild type allele of a nucleotide sequence that is homologous to a mismatch repair gene and/or that lack at least one antigenic determinant on a polypeptide that is encoded by a nucleotide sequence that is homologous to a bacterial mismatch repair gene.

Physiological characteristics that can be analyzed in such a study include, but are not limited to alterations in the rate of accumulation of spontaneous mutations (e.g. by the rate of spontaneous mutation to drug resistance), alterations in the rate of reversion of mutations, alterations in the frequency of recombination between divergent sequences, alterations in the genomic stability of short repeated sequences, sensitivity or resistance to agents that induce DNA damage such as UV-light, nucleotide analogs, alkylating agents, etc. For examples of protocols that may be used in this kind of analysis, see Reenan and Kolodner, Genetics 132: 975-985 (1992); Kat et al., Proc. Nat. Acad. Sci., USA, 90: 6424-6428 (1993); Strand et al., Nature, 365: 274-276 (1993), each of which is incorporated herein by reference.

Classification of Nucleotide Sequences that are Homologous to a Bacterial Mismatch Repair Gene.

Different versions, or "alleles" of the eukaryotic nucleotide sequences of the invention can be classified by their ability to functionally replace an endogenous nucleotide sequence, such as one that is homologous to a bacterial mismatch repair gene in a normal host cell. As used herein, a "wild type" allele is defined as a sequence that can replace an endogenous nucleotide sequence in a normal host cell without having detectable adverse effects on the host cell. A "non-wild type" allele or "alteration" is defined as a eukaryotic nucleotide sequence that cannot replace an endogenous nucleotide sequence in a normal host cell without having detectable adverse effects on the host cell.

Non-wild type alleles of a eukaryotic nucleotide sequence of the invention can differ from wild type alleles in any of several ways including, but not limited to, the amino acid sequence of an encoded polypeptide and the level of expression of an encoded nucleotide transcript or polypeptide product.

Physiological properties that can be monitored in classifying of eukaryotic nucleotide sequences that are homologous to bacterial mismatch repair genes as "wild type" or "non-wild type" include, but are not limited to, growth rate, rate of spontaneous mutation to drug resistance, rate of gene conversion, genomic stability of short repeated DNA sequences, sensitivity or resistance to DNA damage-inducing agents such as UV light, nucleotide analogs, alkylating agents and so on.

Particular "non-wild type" alleles that encode a protein that, when introduced into a host cell, interferes with the endogenous mismatch repair pathway, are termed "dominant negative" alleles.

Inactivation in a Host Cell of Endogenous Nucleotide Sequences that are Homologous to a Bacterial Mismatch Repair Gene and/or the Polypeptides they Encode.

The information provided by the isolated eukaryotic nucleotide sequences and isolated polypeptides of the invention can be used to inactivate, for example, an endogenous nucleotide sequence that is homologous to a bacterial mismatch repair gene and/or a polypeptide product encoded by an endogenous nucleotide sequence that is homologous to a bacterial mismatch repair gene in a host cell (see Example 2, Example 6).

For example, non-wild type alleles of the eukaryotic nucleotide sequences of the invention, can be used to inactivate endogenous nucleotide sequences in a host cell by, for example, hybridizing to endogenous nucleotide sequences and thereby preventing their transcription or translation, or by integrating into the genome of the host cell and thereby replacing or disrupting an endogenous nucleotide sequence. More specifically, a non-wild type allele that can bind to endogenous DNA sequences, for example to form a triple helix, could prevent transcription of endogenous sequences. A non-wild type allele that, upon transcription, produces an "antisense" nucleic acid sequence that can hybridize to a transcript of an endogenous nucleotide sequence could prevent translation of the endogenous transcript. A non-wild type allele, particularly one containing an insertion or deletion of nucleotide sequences, could integrate into the host cell genome and thereby replace or disrupt an endogenous nucleotide sequence that is homologous to a bacterial mismatch repair gene.

In one embodiment, the amount of polypeptide expressed by an endogenous mismatch repair gene may be reduced by providing mismatch repair gene polypeptide—expressing cells, preferably in a transgenic animal, with an amount of mismatch repair gene anti-sense RNA or DNA effective to reduce expression of mismatch repair gene polypeptide.

A transgenic animal (preferably a non-human mammal) could alternatively be provided with a repressor protein that can bind to a specific DNA sequence of a mismatch repair gene, thereby reducing ("repressing") the level of transcription of that mismatch repair gene.

Transgenic animals of the invention which have attenuated levels of polypeptide expressed by their mismatch repair gene(s) have general applicability to the field of transgenic animal generation, as they permit control of the level of expression of genes.

Mutagenesis of Eukaryotic Nucleotide Sequences that are Homologous to a Bacterial Mismatch Repair Gene.

The isolated eukaryotic nucleotide sequences and isolated polypeptides of the invention can be mutagenized by any of several standard methods including treatment with hydroxylamine, passage through mutagenic bacterial strains, etc. The mutagenized sequences can then be classified "wild type" or "non-wild type" as described above.

Mutagenized sequences can contain point mutations, deletions, substitutions, rearrangements etc. Mutagenized sequences can be used to define the cellular function of different regions of the polypeptides they encode. For example, the region of SEQ ID NO.:2 that encodes the putative mitochondrial targeting sequence of SEQ ID NO.: 4 (amino acids 1 to 21) could be mutagenized to delete those amino acids and thereby confirm that those amino acids do in fact function to target the polypeptide of SEQ ID NO.: 4 to the mitochondria. Mitochondrial cellular localization can be detected, for example, by immunofluorescence.

Diagnosis of Cancer Susceptibility

Another preferred embodiment of this invention is in the diagnosis of cancer susceptibility. The eukaryotic nucleotide sequences, polypeptides, and antibodies of this invention are particularly useful for diagnosis of susceptibility to cancers whose incidence correlates with an alteration of a member of the pathway, as described. Such cancers would be expected to contain mismatch repair defective tumors, as described above.

Using any technique known in the art, such as Southern blotting, Northern blotting, PCR, etc. (see, for example, Grompe, supra) the nucleotide sequences of the present invention can be used to identify the presence of relevant non-wild type alleles of sequences that are homologous to a bacterial mismatch repair gene in nucleic acid that has been isolated from individuals being tested for susceptibility to cancers (see discussion of tumor classification above).

Alternatively, the antibodies of the invention can be used as probes in standard techniques such as Western blotting to detect the absence of at least one relevant antigenic determinant on at least one eukaryotic polypeptide encoded by nucleotide sequences that are homologous to a bacterial mismatch repair gene in sample tissues from individuals being tested for susceptibility to cancers.

Identification of Effective Therapeutic Agents

Molecules and host cells provided by the invention can be used to identify therapeutic agents effective against cancer. In particular, the molecules and host cells of the invention could be used to identify therapeutic agents effective against cancers whose incidence correlates with any alteration in the mismatch repair pathway, for example, the presence of a non-wild type allele of a nucleotide sequence that is homologous to a bacterial mismatch repair gene and/or with the lack of at least one antigenic determinant on a polypeptide that is encoded by a nucleotide sequence that is homologous to a bacterial mismatch repair gene.

For instance, as described above, altered host cells can be generated in which an endogenous nucleotide sequence that is homologous to a bacterial mismatch repair gene has been inactivated and/or in which a polypeptide product encoded by an endogenous nucleotide sequence that is homologous to a bacterial mismatch gene has been inactivated. Such an altered host cell can be contacted with various potential therapeutic agents or combinations thereof. Physiological effects of such therapeutic agents or combinations thereof can be assayed by comparing physiological characteristics of an altered host cell that has been contacted with the therapeutic agents or combinations thereof to the physiological characteristics of an unaltered host cell that has been contacted with the therapeutic agents or combinations thereof.

In preferred embodiments, the altered host cell is a mammalian cell, either in tissue culture or in situ (if it is non-human). Other eukaryotic cells such as yeast, may also be used. Potential therapeutic reagents that may be tested include, but are not limited to, intercalating agents, nucleotide analogs, alkylating agents, and X-rays. Possible physiological effects that may be assayed include, but are not limited to, alterations in the rate of accumulation of spontaneous mutations (e.g. by the rate of spontaneous mutation to drug resistance), alterations in the rate of reversion of mutations, alterations in the frequency of recombination between divergent sequences, alterations in the genomic stability of short repeated sequences, sensitivity or resistance to agents that induce DNA damage such as UV-light, nucleotide analogs, alkylating agents, and so on. Preferred therapeutic agents or combinations thereof can be selected.

Preferred therapeutic agents include therapeutic agents or combinations thereof that are relatively toxic to the altered cell as compared to the unaltered cell. Toxicity can be defined in terms of parameters such as increased cell death (assayed by cell count), decreased DNA replication (assayed by, for example, incorporation of tritiated thymidine ($^3$H), and slowed cell growth rate (assayed by cell count).

In one particular embodiment of the invention, altered and unaltered host cells can be contacted with therapeutic agents or combinations thereof in the presence of DNA damaging agents, for example nucleotide analogs (e.g. 5-FU, 2AP), UV Light, or alkylating agents. Because several genes of the invention are involved in repair of damage to DNA, it might be expected that DNA damaging agents alone would be lethal to altered host cells containing an endogenous, but inactivated nucleotide sequence or polypeptide product of the invention. This is because the nucleotide analogs would be incorporated into the DNA, creating mutations that cannot be repaired in the absence of a functional mismatch repair system. Such an effect, however, has not yet been observed in an analogous system, *E. coli* cells, in which the endogenous mutS gene has been mutated. Nonetheless, it is likely that DNA-damaging agents, when combined with other therapeutic agents, would be relatively toxic to altered cells.

The assays described herein allow for the identification of therapeutic agents or combinations thereof that, when administered in the presence of DNA damaging or other agents, would be relatively toxic to an altered host cell containing an inactivated endogenous nucleotide sequence of the invention and/or an inactivated polypeptide product of the invention as compared to an unaltered cell.

Alternative preferred therapeutic agents include those that, when administered, restore the physiological characteristics of the altered cell that has been contacted with the therapeutic reagents, or combination thereof, to more closely resemble the physiological characteristics of an unaltered, untreated host cell. It is further preferred that these therapeutic agents, or combinations thereof, do not significantly affect the physiological characteristics of an unaltered host cell.

Therapeutic and Pharmaceutic Compositions

The nucleotide sequences and polypeptides expressed by these sequences described herein can also be used in pharmaceutical compositions in, for example, gene therapy. An exemplary pharmaceutical composition is a therapeutically effective amount of a mismatch repair nucleotide sequence of the invention optionally included in a pharmaceutically-acceptable and compatible carrier. The term "pharmaceutically-acceptable and compatible carrier" as used herein, and described more fully below, refers to (i) one or more compatible solid or liquid filler diluents or encapsulating substances that are suitable for administration to a human or other animal, and/or (ii) a system, such as a retroviral vector, capable of delivering the mismatch repair nucleotide sequence to a target cell. In the present invention, the term "carrier" thus denotes an organic or inorganic ingredient, natural or synthetic, with which the mismatch repair nucleotide sequences and polypeptides of the invention are combined to facilitate application. The term "therapeutically-effective amount" is that amount of the present pharmaceutical compositions which produces a desired result or exerts a desired influence on the particular condition being treated. Various concentrations may be used in preparing compositions incorporating the same ingredient to provide for variations in the age of the patient to be treated, the severity of the condition, the duration of the treatment and the mode of administration.

The term "compatible", as used herein, means that the components of the pharmaceutical compositions are capable of being commingled with the nucleic acid and/or polypeptides of the present invention, and with each other, in a manner such that there is no interaction that would substantially impair the desired pharmaceutical efficacy.

Dose of the pharmaceutical compositions of the invention will vary depending on the subject and upon particular route of administration used. By way of an example only, an overall dose range of from about, for example, 1 microgram to about 300 micrograms is contemplated for human use. This dose can be delivered on at least two separate occasions, preferably spaced apart by about 4 weeks. Pharmaceutical compositions of the present invention can also be administered to a subject according to a variety of other, well-characterized protocols. For example, certain currently accepted immunization regimens can include the following: (i) Recommended administration times are a first dose at elected date; a second dose at 1 month after first dose; and a third dose at 5 months after second dose. See *Product Information, Physician's Desk Reference*, Merck Sharp & Dohme (1990), at 1442-43. (e.g., Hepatitis B Vaccine-type protocol); (ii) Recommended administration for children is first dose at elected date (at age 6 weeks old or older); a second dose at 4-8 weeks after first dose; a third dose at 4-8 weeks after second dose; a fourth dose at 6-12 months after third dose; a fifth dose at age 4-6 years old; and additional boosters every 10 years after last dose. See *Product Information, Physician's Desk Reference*, Merck Sharp & Dohme (1990), at 879 (e.g., Diptheria, Tetanus and Pertussis-type vaccine protocols). Desired time intervals for delivery of multiple doses of a particular composition can be determined by one of ordinary skill in the art employing no more than routine experimentation.

The polypeptides of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

The compositions include those suitable for oral, rectal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. All methods include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acid and/or polypeptide of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the nucleic acid and/or polypeptides of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The nucleic acids and/or polypeptides of the present invention can also be conjugated to a moiety for use in vaccines. The moiety to which the nucleic acids and/or polypeptides is conjugated can be a protein, carbohydrate, lipid, and the like. The chemical structure of this moiety is not intended to limit the scope of the invention in any way. The moiety to which nucleic acids and/or polypeptides may be bound can also be an adjuvant. The term "adjuvant" is intended to include any substance which is incorporated into or administered simultaneously with the nucleic acids and/or polypeptides of the invention which potentiates the immune response in the subject. Adjuvants include aluminum compounds, e.g., gels, aluminum hydroxide and aluminum phosphate gels, and Freund's complete or incomplete adjuvant. The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), leutinan, pertussis toxin, lipid A, saponins and peptides, e.g., muramyl dipeptide. Rare earth salts, e.g., of lanthanum and cerium, may also be used as adjuvants. The amount of adjuvant required depends upon the subject and the particular therapeutic used and can be readily determined by one skilled in the art without undue experimentation.

Identification of Factors that Interact with Polypeptide Products of Eukaryotic Nucleotide Sequences of the Invention The nucleotide sequences and polypeptides of the invention can be used to identify interacting factors, some of which will themselves be encompassed by the invention. That is, the polypeptide products of different eukaryotic nucleotide sequences of the invention may well interact with each other. In particular, identifying those proteins that interact with the polypeptide of SEQ ID NO.:3 should further identify other proteins that act in mismatch repair. Yeast provides a particularly powerful system for genetic identification of interacting factors. In addition to genetic methods, several biochemical methods, such as co-immunoprecipation and protein affinity chromatography can be used to identify interacting proteins.

Biochemical Methods

In one embodiment of the invention, co-immunoprecipitation is used to identify proteins that interact with the isolated polypeptides of the invention, such as the polypeptides of SEQ ID NOS.:3, SEQ ID NO.:4 or SEQ ID NO.: 16. Co-immunoprecipitation has proven useful for identifying interacting proteins (see, for example, Kolodziej and Young, Methods Enzymol. 194:508, 1991, incorporated herein by reference; Pallas et al., J. Virol 62:3934, 1988, incorporated herein by reference).

In one preferred embodiment of the invention, the polypeptide of SEQ ID NO.:3 may be engineered using standard methods to contain a flu 12CA5 epitope tag (Kolodziej and Young, supra) at either or both the N-terminus and the C-terminus. It may be necessary to insert the epitope at internal locations. The tagged protein may then tested for the ability to provide mismatch repair function in yeast cells whose endogenous copy of the MSH2 gene (SEQ ID NO.:1) has been inactivated. If functional tagged proteins cannot be produced, polyclonal or monoclonal antisera raised against antigenic determinants on the polypeptide of SEQ ID NO.:3 may be used.

Tagged protein is expressed in log or stationary phase, in mitotic cells or in meiotic cells. Different levels of expression (e.g. native promoter, cen vector; GAL10 promoter, cen vector; GAL10 promoter, 2µ based vector) can be tested. The cells are lysed and the tagged protein is precipitated using the flu 12CA5 antibody (or the polyclonal antisera raised against SEQ ID NO.:3 determinants) and analyzed by one and two dimensional gel electrophoresis to detect proteins that co-precipitate (Koloddziej and Young 1991, supra; Pallas et al., supra).

The specificity of co-precipitation is evaluated in experiments in which untagged, rather than tagged protein is expressed and in which tagged protein is expressed and control mouse antisera are substituted for the flu 12CA5 antibody. Sensitivity to salt and different detergents like SDS, NP40 and digitonin are used to evaluate the stability and specificity of observed interactions. The possibility that such interactions require mispaired bases can be tested by adding oligonucleotide duplexes containing mispaired bases and control oligonucleotide duplexes lacking mispaired bases to the cell extracts prior to addition of antibody.

If interacting proteins are found, gel electrophoresis or immunaffinity chromatography can be used to purify sufficient amounts to obtain N-terminal and internal protein sequences by standard techniques (see, for example, Matsudaira J. Biol. Chem. 262:10035-10038, 1987, incorporated herein by reference). This sequence information can then be used for comparison with DNA and protein databases and for cloning the genes encoding the proteins for use in reverse genetics analysis and protein overproduction. An identical protocol may be performed with the polypeptide of SEQ ID NO.: 4 or SEQ ID NO.: 16, or any other polypeptide that is encoded by a eukaryotic nucleotide sequence of the invention.

In another embodiment of the invention, proteins that interact with the polypeptides of the invention, in particular with polypeptides of SEQ ID NOS.:3, 4 and/or 16, may be identified using a protein affinity column on which these proteins are immobilized. (See, Formosa et al., Proc. Nat. Acad. Sci., USA, 80:2442, 1983. For example, 1 to 10 mg of protein can be covalently linked to AffiGel-10 (made by BioRad Laboratories, Richmond, Calif.) or equivalent matrix. Parallel chromatography experiments on a column containing a polypeptide of the invention (e.g., SEQ ID NO.: 3) and a control BSA column can be performed to identify proteins that specifically bind to the polypeptide of the invention (e.g., SEQ ID NO.:3). Identified interacting proteins can be N-terminal sequenced as described above. Also, antibodies can be produced to react with identified interacting proteins. Such antibodies can then be used, for example, to screen expression libraries to facilitate cloning of genes that encode the identified interacting proteins. Once interacting proteins have been identified and isolated, biochemical experiments may be performed to assess the functional significance of their interaction with the polypeptides of the invention (e.g., SEQ ID NO.:3). Such experiments include determining: 1) if the interacting protein(s) enhance the mispair binding activity of the polypeptide of the invention; 2) if the interacting protein(s) restore function to inactive in vitro systems; and 3) if the interacting protein(s) substitute for any required protein fractions in in vitro reconstitution experiments. For a description of a representative in vitro system, see Muster-Nassal and Kolodner, Proc. Nat. Acad. Sci., USA, 83:7618 (1986), incorporated herein by reference.

Biochemical methods can also be used to test for specific interactions between isolated polypeptides of the invention and already known proteins, for example proteins involved in DNA replication or recombination. In one approach, these known proteins can be immobilized on nitrocellulose filters or other supports, the support blocked to prevent non-specific binding, incubated with an epitope-tagged polypeptide of the invention, for example a epitope-tagged version of SEQ ID NOS.:3, 4 and/or 16, and then probed with antibody reactive with the epitope tag (for example, the 12CA5 flu antibody) to detect epitope-tagged polypeptides of the invention that have bound to the filter by interaction with the immobilized known protein. Non-epitope-tagged polypeptides of the invention can be used instead in combination with antisera reactive against antigenic determinants of those polypeptides.

When interacting proteins have been cloned, standard methods including mutagenesis and others described in this application can be used to determine the cellular function(s) of those proteins, e.g., mismatch repair, other types of DNA repair, DNA replication, recombination, and so on.

Once proteins have been identified that interact with an isolated polypeptide of the invention, similar types of experiments can be performed to identify proteins that interact with those newly identified proteins. By systematically applying this approach, it may be possible to identify a number of proteins that function in mismatch repair and simultaneously gain insight into the mechanism by which they act.

Genetic Methods

Alternately, or additionally, genetic methods can also be used to identify proteins that interact with polypeptides of the invention. It is expected that at least some of the identified proteins will be encoded by genes that are involved in mismatch repair, are homologous to a bacterial mismatch repair gene, and are therefore themselves within the scope of the invention.

For example, one method is the two hybrid system described by Chien et al., Proc. Nat. Acad. Sci. USA., 88:9578 (1991), incorporated herein by reference. This method may be used to identify proteins that interact with polypeptides of the invention. In particular, the N-terminal half of SEQ ID NO.:3 may contain at least one region that interacts with other proteins (Reenan and Kolodner, Genetics 132:963, supra). This region may be fused at the end of amino acids 1-147 of the Gal4 protein to make a fusion protein that will bind to the Gal4 site in DNA. Amino acids 1-616 of SEQ ID NO.:3 can be used initially, but other segments of this polypeptide, including the whole polypeptide, or analogous regions of SEQ ID NOs.:4 and 16 could alternately be used.

The fusion protein can then be used to screen an available library of yeast DNA fragments fused to the Gal4 activation domain for activation of a GAL1-LacZ reporter. Positives can be rescreened to eliminate plasmids from the library that activate in the absence of the SEQ ID NO.:3 polypeptide segment. The remaining positive clones may be used to isolate disruptions of the yeast genes from which the sequences on the library plasmids originated. Cells containing such disruptions may be analyzed to determine if the disruptions affect spontaneous mutation rate, gene conversion, repair of plasmids containing mispaired bases, and/or genomic stability of short repeated DNA sequences, as would be expected for disruption of a gene involved in mismatch repair. This method is rapid since the required libraries are readily available from any of several sources, for example, Dr. Roger Brent at the Massachusetts General Hospital. It is straightforward to determine if any cloned genes have properties consistent with a role in mismatch repair. Libraries of DNA fragments from eukaryotic organisms other than yeast that are fused to Gal4 for an activation domain can also be screened. Such libraries can be made by using standard methods.

An alternate genetic method that can be used to identify proteins that interact with polypeptides of the invention and the genes that encode them is to use secondary mutation analysis. For example, yeast cells or mammalian carrying a mutation in the MSH2 gene, corresponding to SEQ ID NO.:1 or mammalian MSH2 homologue can be mutagenized and screened to identify secondary mutations that either correct or augment the mismatch repair defects of the original, MSH2-disrupted cells. Mutagenized cells can be assayed for effects on, for example, spontaneous mutation rate, gene conversion, repair of plasmids containing mispaired bases, and genomic stability of short repeated DNA sequences, as already described in this application.

Secondary mutations that correct defects of the MSH2-disrupted cells are termed "suppressors". Suppressor mutations can be isolated in genes that interact with MSH2. For explanation of the logic in isolating suppressor mutations and protocols involved see, for example, Adams and Botstein, Genetics 121: 675-683 (1989); Novick et al., Genetics 121: 659-674 (1989); Jarvik and Botstein, Proc. Nat. Acad. Sci. USA 72: 2738-2742 (1975), all of which are incorporated herein by reference. Those genes can then be cloned and sequenced by standard protocols.

Secondary mutations that augment the mismatch repair defects of the original, MSH2-disrupted cells can sometimes have extreme effects, to the extent the mutagenized cells are no longer viable. Such secondary mutations are referred to as "synthetic lethals". For an explanation of the logic and protocols involved in identifying these mutations, see Kranz and Holm, Proc. nat. Acad. Sci., USA 87: 6629-6633, (1990), incorporated herein by reference. The effects of synthetic lethal mutations can be assayed in the presence or absence of DNA damaging agents such as UV light, nucleotide analogs, alkylating agents, etc. As mentioned above, it is desirable for the possible development of therapeutic agents effective against cancer to identify circumstances under which DNA damaging agents are lethal to host cells bearing an inactivated eukaryotic nucleotide sequence of the invention. In this case, studies of synthetic lethality in yeast are used to identify genes that, when mutated, render MSH2-disrupted cells sensitive to DNA damaging agents.

Such genes would be logical targets for chemotherapy development. Agents, such as antisense reagents or other soluble enzyme inhibitors, for example, that inactivate such genes might render HNPCC tumors having an altered endogenous copy of SEQ ID NO.:9; the identified human genomic nucleotide sequence of the invention that is homologous to the *E. coli* mutS gene, sensitive to DNA damaging agents such as nucleotide analogs, light, alkylating agents, or other therapeutic agents.

Expression of Pathway Members

Recombinant vectors containing nucleotide sequences of the invention can be introduced into host cells by, for example, transformation, transfection, infection, electroporation, etc. Recombinant vectors can be engineered such that the eukaryotic nucleotide sequences of the invention are placed under the control of regulatory elements (e.g. promoter sequences, polyadenylation signals, etc.) in the vector sequences. Such regulatory elements can function in a host cell to direct the expression and/or processing of nucleotide transcripts and/or polypeptide sequences encoded by the eukaryotic nucleotide sequences of the invention.

Expression systems can utilize prokaryotic and/or eukaryotic (i.e., yeast, human) cells. See, for example, "Gene Expression Technology", Volume 185, *Methods in Enzymology*, (ed. D. V. Goeddel), Academic Press Inc., (1990) incorporated herein by reference. A large number of vectors have been constructed that contain powerful promoters that generate large amounts of mRNA complementary to cloned sequences of DNA introduced into the vector. For example, and not by way of limitation, expression of eukaryotic nucleotide sequences in *E. coli* may be accomplished using lac, trp, lambda, and recA promoters. See, for example, "Expression in *Escherichia coli*", Section II, pp. 11-195, V. 185, *Methods in Enzymology*, supra; see also Hawley, D. K., and McClure, W. R., "Compilation and Analysis of *Escherichia coli* promoter DNA sequences", Nucl. Acids Res., 11: 4891-4906 (1983), incorporated herein by reference. Expression of eukaryotic nucleotide sequences of the invention, and the polypeptides they encode, in a recombinant bacterial expression system can be readily accomplished.

Yeast cells suitable for expression of the eukaryotic nucleotide sequences of the invention, and the polypeptides they encode, include the many strains of *Saccharomyces cerevisiae* (see above) as well as *Pichia pastoris*. See, "Heterologous Gene Expression in Yeast", Section IV, pp. 231-482, V. 185, *Methods in Enzymology*, supra, incorporated herein by reference. Moreover, a large number of vector-mammalian host systems known in the art may be used. See, Sambrook et al., Volume III, supra and "Expression of Heterologous Genes in Mammalian Cells", Section V, pp. 485-596, V. 185, *Methods in Enzymology*, supra, incorporated herein by reference.

Suitable expression systems include those that transiently or stably expressed DNA and those that involve viral expression vectors derived from simian virus 40 (SV 40), retroviruses, and baculoviruses. These vectors usually supply a promoter and other elements such as enhancers, splice acceptor and/or donor sequences, and polyadenylation signals. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript® (Stratagene) plasmid derivatives. Recombinant molecules can be introduced into host cells via transformation, transfection, infection, electroporation, etc. Generally, expression of a protein in a host is accomplished using a vector containing DNA encoding that protein under the control of regulatory regions that function in the host cell.

In particular, expression systems that provide for overproduction of a eukaryotic homologue of a bacterial mismatch repair protein can be prepared using, for example, the methods described in U.S. Pat. No. 4,820,642 (Edman et al., Apr. 11, 1989), incorporated herein by reference. The general requirements for preparing one form of expression vector capable of overexpression are: (1) the presence of a gene (e.g., a prokaryotic gene) into which a nucleotide sequence capable of encoding a eukaryotic homologue of a bacterial mismatch repair protein can be inserted; (2) the promoter of this prokaryotic gene; and (3) a second promoter located upstream from the prokaryotic gene promoter which overrides the prokaryotic gene promoter, resulting in overproduction of the extracellular matrix protein. The second promoter is obtained in any suitable manner. Possible host cells into which recombinant vectors containing eukaryotic nucleotide sequences of the invention can be introduced include, for example, bacterial cells, yeast cells, non-human mammalian cells in tissue culture or in situ, and human cells in tissue culture but not in situ.

Eukaryotic nucleotide sequences of the invention that have been introduced into host cells can exist as extra-chromosomal sequences or can be integrated into the genome of the host cell by homologous recombination, viral integration, or other means. Standard techniques such as Northern blots and Western blots can be used to determine that introduced sequences are in fact being expressed in the host cells.

In one method of expressing a human nucleotide sequence that is homologous to a bacterial mismatch repair gene and the polypeptide it encodes, a cDNA clone that contains the entire coding region of the polypeptide (e.g. SEQ ID NO.:8) is cloned into a eukaryotic expression vector and transfected into cells derived from the simian kidney (e.g., COS-7 cells). Expression is monitored after transfection by, for example, Northern, Southern, or Western blotting.

Host cells carrying such introduced sequences can be analyzed to determine the effects that sequence introduction has on the host cells. In particular, cells could be assayed for alterations in the rate of accumulation of spontaneous mutations (e.g. by the rate of spontaneous mutation to drug resistance), in the rate of reversion of mutations, in the frequency of homologous recombination, in the frequency of recombination between divergent sequences, or in the genomic stability of short repeated sequences. In particular, mammalian cells carrying introduced sequences of the invention could be tested for the stability of di- and trinucleotide repeats by the method of Schalling et al. (Schalling et al. Nature. Genetics, 4:135, 1993, incorporated herein by reference.), or for sensitivity to agents that induce DNA damage such as UV-light, nucleotide analogs, alkylating agents, etc.

In particular embodiments, a nucleotide sequence of the invention may be used to inactivate an endogenous gene by homologous recombination, and thereby create a mismatch repair gene-deficient cell, tissue, or animal. For example, and not by way of limitation, a recombinant human nucleotide sequence of the present invention may be engineered to contain an insertional mutation (e.g., the neo gene) which, when inserted, inactivates transcription of an endogenous gene that is a homologue of a bacterial mismatch repair gene. Such a construct, under the control of a suitable promoter operatively linked to a nucleotide sequence of the invention, may be introduced into a cell by a technique such as transformation, transfection, transduction, injection, etc. In particular, stem cells lacking an intact endogenous mismatch repair gene may generate transgenic animals deficient in that mismatch repair gene, and the polypeptide it encodes, via germ line transmission.

In a specific embodiment of the invention (See Example 2 or Example 6), an endogenous mismatch repair gene in a cell may be inactivated by homologous recombination with a mutant mismatch repair gene, thereby allowing the development of a transgenic animal from that cell, which animal lacks the ability to express the encoded mismatch repair gene polypeptide. In another embodiment, a construct can be provided that, upon transcription, produces an "anti-sense" nucleic acid sequence which, upon translation, will not produce the required mismatch repair gene polypeptide.

A "transgenic animal" is an animal having cells that contain DNA which has been artificially inserted into a cell, which DNA becomes part of the genome of the animal that develops from that cell. The preferred DNA contains yeast and/or human nucleotide sequences that are homologous to a bacterial mismatch repair gene and may be entirely foreign to the transgenic animal or may be identical to the natural mismatch repair gene of the animal, but which is inserted into the animal's genome at a location which differs from that of the natural copy. Transgenic animals could provide good model systems for studying the development of cancer, the effects of potential therapeutic reagents, and the carcinogenicity of chemical agents administered to the animals.

Functional Equivalents and Unique Fragments of Isolated Nucleotide Sequences and Polypeptides This invention pertains to isolated eukaryotic nucleotide sequences that are homologous to a bacterial mismatch repair gene so that the isolated eukaryotic nucleotide sequences, their functional equivalents, or unique fragments of these sequences, may be used in accordance with this the invention. Nucleotide sequences or "probes" that are capable of hybridizing are also included. Additionally, the isolated polypeptides encoded by these sequences, and unique fragments of the polypeptides, may also be used in accordance with the invention.

The term "unique fragment" refers to any portion of a nucleotide sequence or polypeptide of the invention that is found only among eukaryotic nucleotide sequences that are homologous to a bacterial mismatch repair gene or the polypeptides they encode.

For example, a unique fragment of a eukaryotic nucleotide sequence that is homologous to the *E. coli* mutS gene is only found in eukaryotic nucleotide sequences that are homologous to the *E. coli* mutS gene. In particular, because the exact nucleotide sequence is known for two yeast homologues (SEQ ID NOs.:1 and 2) and a human homologue (SEQ ID NO.:8) of the *E. coli* mutS gene, one of ordinary skill in the art can readily determine the portions of the yeast and human homologues that are not found in other nucleotide sequences.

The term "unique fragment" can refer to nucleotide or amino acid sequences that are found in all eukaryotic homologues of a particular bacterial mismatch repair gene or protein, or to nucleotide or amino acid sequences that are found in only one eukaryotic homologue and are absent from other eukaryotic homologues of the same bacterial mismatch repair gene or protein. In one particular example, the amino acid sequence FATHF (SEQ ID NO.:6) is a unique fragment of the yeast and human homologues (SEQ ID NOs.:3, 4, 16) of the bacterial mutS/hexA mismatch repair protein. The amino acid sequence CMFATHF is a unique fragment of only the human homologue (amino acids 797 to 803 of SEQ ID NO.: 16).

"Unique fragments" can be practically defined by the use of computer programs capable of comparing nucleic acid and/or polypeptide sequences. In particular a computer program such as the HYPERBLAST program (Altschul et al. J. Mol. Biol. 215:403-410, 1990, incorporated herein by reference) can be used to translate a DNA sequence in all possible reading frames and then to search known databases (e.g. GenBank, PIR, SWIS-PROT) for similar or identical sequences.

PCR can be used to generate unique fragments of the eukaryotic homologues of the invention. For example, the PCR-generated probes of SEQ ID NOs.: 20, 19, and 15 are unique fragments of, respectively, the yeast homologues (SEQ ID NOs.:1 and 2) and the human homologue (SEQ ID NO.:8) of the E. coli mutS gene. Similarly, the PCR-generated fragment of SEQ ID NO.:10 is a unique fragment of the mouse homologue of the E. coli mutS gene. Also, primer pairs that can be used to amplify unique fragments of the human homologue of the E. coli mutS gene are represented by SEQ ID NOs.: 17/18, 17/23, 25/26, 29/30, 31/32, 33/34, 35/36, 37/38, 39/40. In some cases (e.g. SEQ ID NOs.:17/18), these primer sets may also be useful in amplifying unique fragments of a non-human eukaryotic homologgue of the E. coli mutS gene.

Preferred unique fragments of a nucleotide sequence are between length 15 and 6000 nucleotides (nt.), with particularly preferred fragments being less than approximately 3000 nt long.

Unique fragments of a nucleotide sequence may be single-stranded. Preferred unique fragments of a polypeptide are between approximate 5 and 100 amino acids in length.

The term "functional equivalent", when applied to the nucleotide sequences of the invention, describes a sequence that satisfies one of the following conditions: (i) the nucleotide sequence in question can hybridize to a eukaryotic nucleotide sequence that is homologous to a bacterial mismatch repair gene, but it does not necessarily hybridize to that sequence with an affinity that is the same as that of the naturally occurring eukaryotic nucleotide sequence that is homologous to a bacterial mismatch repair gene (ii) the nucleotide sequence in question can serve as a probe to distinguish between eukaryotic nucleotide sequences that are homologous to yeast mismatch repair genes and other nucleotide sequences.

In particular, we note that the human cDNA clone of SEQ ID NO.:8 was isolated from a single cDNA library. Due to normal sequence variation within the human population, clones derived from different libraries would likely show sequence variability relative to the clone of SEQ ID NO.:8. In particular, in some instances, the phenomenon of codon degeneracy (see below), will contribute to differences in the amino acid sequence of the encoded protein. In other cases, even the protein sequence may vary somewhat. In most instances, the changes are insignificant and the nucleotide and amino acid sequences are functionally equivalent. As discussed below, such equivalence can be empirically determined by comparisons of structural and/or functional characteristics.

Due to the degeneracy of nucleotide coding sequences (see Alberts et al., Molecular Biology of the Cell, Garland Publishing, New York and London, 1989-page 103, incorporated herein by reference), other nucleic acid sequences may be used in the practice of the present invention. These include, but are not limited to, sequences comprising all or portions of the sequences depicted in SEQ ID NOS.:1, 2, 8, and 10 that have been altered by the substitution of different codons encoding the same amino acid residue within the sequence, thus producing a silent change. Almost every amino acid except tryptophan and methionine is represented by several codons. Often the base in the third position of a codon is not significant, because those amino acids having 4 different codons differ only in the third base. This feature, together with a tendency for similar amino acids to be represented by related codons, increases the probability that a single, random base change will result in no amino acid substitution or in one involving an amino acid of similar character. For example, several different nucleotide sequences are capable of encoding the amino acid sequences of SEQ ID NOS.: 6 and 7 [FATH(F/Y)], which are unique and universal to homologues of the E. coli MutS protein. Nucleotide sequences capable of encoding FATHF can be summarized as the sequence 5'-TTYGCNACNCAYTTY-3' (SEQ ID NO.:41), and nucleotide sequences capable of encoding FATHY can be summarized as the sequence 5'-TTYGCNACNCAYTAY-3' (SEQ ID NO.:42), where Y represents C or T/U, and N represents A, C, G, or T/U. Such degenerate nucleotide sequences are regarded as functional equivalents of the specifically claimed sequences.

The nucleotide sequences of the invention (e.g. SEQ ID NOs.:1, 2, 8, 10, etc) can be altered by mutations such as substitutions, additions or deletions that provide for functionally equivalent nucleic acid sequence. In particular, a given nucleotide sequence can be mutated in vitro or in vivo, to create variations in coding regions and/or to form new restriction endonuclease sites or destroy preexisting ones and thereby to facilitate further in vitro modification. Any technique for mutagenesis known in the art can be used including, but not limited to, in vitro site-directed mutagenesis (Hutchinson, et al., J. Biol. Chem. 253:6551, 1978), use of TAB® linkers (Pharmacia), PCR-directed mutagenesis, and the like. The functional equivalence of such mutagenized sequences, as compared with un-mutagenized sequences, can be empirically determined by comparisons of structural and/or functional characteristics.

Polypeptide products of the invention or unique fragments or functional equivalents thereof include, but are not limited to, those containing as a primary amino acid sequence all, or unique parts of the amino acid residues substantially as depicted in SEQ ID NOS.:3, 4, and 16, including altered sequences in which functionally equivalent amino acid residues are substituted for residues within the sequence, resulting in a functionally silent change. The polypeptides of the invention may be prepared by recombinant nucleotide expression techniques or by chemical synthesis using standard peptide synthesis techniques.

According to the invention, an amino acid sequence is "functionally equivalent" compared with the sequences depicted in SEQ ID NOS.:3, 4 and 16 if the amino acid sequence contains one or more amino acid residues within the sequence which can be substituted by another amino acid of a similar polarity which acts as a functional equivalent. The term "functionally equivalent", when applied to the amino acid sequences of the invention, also describes the relationship between different amino acid sequences whose physical or functional characteristics are substantially the same. Substitutions, deletions or insertions of amino acids often do not produce radical changes in the physical and chemical characteristics of a polypeptide, in which case polypeptides containing the substitution, deletion, or insertion would be considered to be functionally equivalent to polypeptides lacking the substitution, deletion, or insertion.

Functionally equivalent substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Substantial changes in functional or, for example, immunological properties may be avoided by selecting substitutes that do not differ from the original amino acid residue. More significantly, the substitutions can be chosen for their effect on: (i) maintaining the structure of the peptide backbone in the area of the substitution, for example, as a sheet or helical conformation; (ii) maintaining the charge or hydrophobicity of the molecule at the target side; or (iii) maintaining the bulk of the side chain. The substitutions that in general could expected to induce greater changes, and therefore should be avoided, are those in which: (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

Most deletions and insertions in a polypeptide encoded by eukaryotic nucleotide sequences that are homologous to a bacterial mismatch repair gene, and substitutions in particular, are not expected to produce radical changes in the characteristics of the polypeptide. Nevertheless, when it is difficult to predict the exact effect of the substitution, deletion, or insertion in advance of doing so, one skilled in the art will appreciate that the effect will be evaluated using routine screening assays as described herein and known in the art. For example, a change in the immunological character of a human mismatch repair gene product, such as binding to a given antibody, can be measured by an immunoassay such as a competitive type immunoassay.

The functional equivalence of two polypeptide sequences can be assessed by examining physical characteristics (e.g. homology to a reference sequence, the presence of unique amino and sequences, etc.) and/or functional characteristics analyzed in vitro or in vivo. For example, functional equivalents of the proteins of SEQ ID NOs.:3, 4, or 16 would be expected to contain the amino acids sequence FATH(F/Y). These functional equivalents may also contain a helix-turn-helix DNA binding motif, a $Mg^{2+}$ ATP binding domain, and/or the amino acid sequence TGPNM. These functional equivalents may also be capable of binding to mismatched base pairs in, for example, a filter-binding assay.

Functional equivalents may also produce a dominant mismatch-repair-defective phenotype when expressed in *E. Coli*, as detected in an assay described herein, or may otherwise behave like mismatch repair proteins in other assays herein described or known in the art.

Also included within the scope of the invention are polypeptides or unique fragments or derivatives thereof that are differentially modified during or after translation, e.g., by phosphorylation, glycosylation, crosslinking, acylation, proteolytic cleavage, linkage to an antibody molecule, membrane molecule or other ligand, (Ferguson, et al., Ann. Rev. Biochem. 57:285-320, 1988).

Polypeptide fragments of the invention can be produced, for example, by expressing cloned nucleotide sequences of the invention encoding partial polypeptide sequences. Alternatively, polypeptide fragments of the invention can be generated directly from intact polypeptides. Polypeptides can be specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the e-amino groups of lysine with ethyltrifluorothioacetate in mildly basic solution yields a blocked amino acid residue whose adjacent peptide bond is no longer susceptible to hydrolysis by trypsin. Goldberger et al. Biochem., 1:401 (1962). Treatment of such a polypeptide with trypsin thus cleaves only at the arginyl residues.

Polypeptides also can be modified to create peptide linkages that are susceptible to proteolytic enzyme catalyzed hydrolysis. For example, alkylation of cysteine residues with 6-halo ethylamines yields peptide linkages that are hydrolyzed by trypsin. Lindley, Nature, 178: 647 (1956). In addition, chemical reagents that cleave polypeptide chains at specific residues can be used. Withcop, Adv. Protein Chem. 16: 221 (1961). For example, cyanogen bromide cleaves polypeptides at methionine residues. Gross & Witkip, J. Am Chem Soc., 83: 1510 (1961). Thus, by treating mismatch repair gene polypeptides or fragments thereof with various combinations of modifiers, proteolytic enzymes and/or chemical reagents, numerous discrete overlapping peptides of varying sizes are generated. These peptide fragments can be isolated and purified from such digests by chromatographic methods.

Alternatively, polypeptides of the present invention can be synthesized using an appropriate solid state synthetic procedure. Steward and Young, *Solid Phase Peptide Synthesis*, Freemantle, San Francisco, Calif. (1968). A preferred method is the Merrifield process. Merrifield, *Recent Progress in Hormone Res.*, 23: 451 (1967). The activity of these peptide fragments may conveniently be tested using, for example, a filter binding or immunologic assay as described herein.

Also within the scope of the invention are nucleic acid sequences or proteins encoded by nucleic acid sequences derived from the same gene but lacking one or more structural features as a result of alternative splicing of transcripts from a gene that also encodes the complete mismatch repair gene, as defined previously.

Nucleic acid sequences complementary to DNA or RNA sequences encoding polypeptides of the invention or a functionally active portion(s) thereof are also provided. In animals, particularly transgenic animals, RNA transcripts of a desired gene or genes may be translated into polypeptide products having a host of phenotypic actions. In a particular aspect of the invention, antisense oligonucleotides can be synthesized. These oligonucleotides may have activity in their own right, such as antisense reagents which block translation or inhibit RNA function. Thus, where human polypeptide is to be produced utilizing the nucleotide sequences of this invention, the DNA sequence can be in an inverted orientation which gives rise to a negative sense ("antisense") RNA on transcription. This antisense RNA is not capable of being translated to the desired product, as it is in the wrong orientation and would give a nonsensical product if translated.

Nucleotide Hybridization Probes

The present invention also provides an isolated nucleotide "probe" that is capable of hybridizing to a eukaryotic target sequence that is homologous to a bacterial mismatch repair gene.

A probe is a ligand of known qualities that can bind selectively to a target. A nucleotide probe according to the invention is a strand of nucleic acid having a nucleotide sequence that is complementary to a nucleotide sequence of a target strand. In particular, the nucleotide sequence of a probe of the present invention is complementary to a sequence found in a eukaryotic nucleotide sequence that is homologous to a bacterial mismatch repair gene. It is specifically contemplated that probes of the invention may hybridize to a segment of a eukaryotic nucleotide sequence that is homologous to the E. Coli mutS gene. In particular, probes that hybridize to any unique segment of any of SEQ ID NOs.:1, 2, 8, 9, 10 and 45 are included in the invention. Such probes are useful, for example, in nucleic acid hybridization assays, Southern and Northern blot analyses, etc. Hybridization conditions can vary depending on probe length and compositions. Conditions appropriate to a particular probe length and composition can be readily determined by consultation with standard reference materials (see Sambrook et al. supra).

A preferred oligonucleotide probe typically has a sequence somewhat longer than that used for the PCR primers. A longer sequence is preferable for the probe, and it is valuable to minimize codon degeneracy. A representative protocol for the preparation of an oligonucleotide probe for screening a cDNA library is described in Sambrook, J. et al., Molecular Cloning, Cold Spring Harbor Press, New York, 1989. In general, the probe is labelled, e.g., $^{32}$P, and used to screen clones of a cDNA or genomic library.

Preferred nucleotide probes are at least 20-30 nucleotides long, and contain at least 15-20 nucleotides that are complimentary to their target sequence in a eukaryotic nucleotide sequence that is homologous to a bacterial mismatch repair gene. Preferred nucleotide probes can be radioactively labelled or conjugated to fluorescent tags such as those available from New England Biolabs (Beverly, Mass.) or Amersham (Arlington Heights, Ill.) and can be used to probe, for example, Southern blots, Northern blots, plaque lifts, colony lifts, etc. Nucleotide probes of the invention include, for example, probes made by chemical synthesis and probes generated by PCR.

Preferred nucleotide probes of the invention, be they oligonucleotides, PCR—generated fragments, or other nucleic acid sequences (e.g. isolated clones), can be used in the general protocol outlined herein to isolate eukaryotic nucleotide sequences that are homologous to a bacterial mismatch repair gene.

Nucleotide probes of the invention can also be used in standard procedures such as nick translation, 5' end labelling and random priming (Sambrook et al. supra).

Antibodies

The term "antibodies" is meant to include monoclonal antibodies, polyclonal antibodies and antibodies prepared by recombinant nucleic acid techniques that are selectively reactive with polypeptides encoded by eukaryotic nucleotide sequences of the present invention. The term "selectively reactive" refers to those antibodies that react with one or more antigenic determinants of a polypeptide encoded by a eukaryotic nucleotide sequence that is homologous to a bacterial mismatch repair gene, and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes.

In particular, antibodies may be raised against amino-terminal (N-terminal) or carboxy-terminal (C-terminal) peptides of a polypeptide encoded by eukaryotic nucleotide sequences that are homologous to a bacterial mismatch repair gene.

Generally, to isolate antibodies to a polypeptide encoded by a eukaryotic nucleotide sequence of the invention, a peptide sequence that contains an antigenic determinant is selected as an immunogen.

This peptide immunogen can be attached to a carrier to enhance the immunogenic response. Although the peptide immunogen can correspond to any portion of a polypeptide encoded by a eukaryotic nucleotide sequence of the invention, certain amino acid sequences are more likely than others to provoke an immediate response, for example, an amino acid sequence including the C-terminal amino acid of a polypeptide encoded by a gene that contains nucleotide sequences of the invention.

Other alternatives to preparing antibodies that are reactive with a polypeptide encoded by a human nucleotide sequence of the invention include: (i) immunizing an animal with a protein expressed by a prokaryotic (e.g., bacterial) or eukaryotic cell; the cell including the coding sequence for all or part of a polypeptide encoded by a eukaryotic nucleotide sequence that is homologous to a bacterial mismatch repair gene; or (ii) immunizing an animal with whole cells that are expressing all or a part of a polypeptide encoded by a eukaryotic nucleotide sequence that is homologous to a bacterial mismatch repair gene. For example, cDNA clone encoding a polypeptide of the present invention may be expressed in a host using standard techniques (see above; see Sambrook et al., Molecular Cloning; A Laboratory Manual, Cold Spring Harbor Press, Cold Spring Harbor, N.Y.: 1989) such that 5-20% of the total protein that can be recovered from the host is polypeptides encoded by a eukaryotic nucleotide sequence that is homologous to a bacterial mismatch repair gene. Recovered proteins can be electrophoresed using PAGE and the appropriate protein band can be cut out of the gel. The desired protein sample can then be eluted from the gel slice and prepared for immunization. Alternatively, a protein of interest can be purified by using conventional methods such as, for example, ion exchange hydrophobic, size exclusion, or affinity chromatography.

Once the protein immunogen is prepared, mice can be immunized twice intraperitoneally with approximatively 50 micrograms of protein immunogen per mouse. Sera from such immunized mice can be tested for antibody activity by immunohistology or immunocytology on any host system expressing a polypeptide encoded by eukaryotic nucleotide sequence that is homologous to a bacterial mismatch repair gene and by ELISA with the expressed polypeptide encoded by a eukaryotic nucleotide sequence that is homologous to a bacterial mismatch repair gene. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody as provided by the invention, the amino acid sequence of polypeptides encoded by a eukaryotic nucleotide sequence of the present invention may be analyzed in order to identify portions of amino acid sequence which may be associated with increased immunogenicity. For example, polypeptide sequences may be subjected to computer analysis to identify potentially immunogenic surface epitopes. Such computer analysis can include generating plots of antigenic index, hydrophilicity, structural features such as amphophilic helices or amphophilic sheets and the like.

For preparation of monoclonal antibodies directed toward polypeptides encoded by a eukaryotic nucleotide sequence of the invention, any technique that provides for the production of antibody molecules by continuous cell lines may be used. For example, the hybridoma technique originally developed by Kohler and Milstein (Nature, 256: 495-497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al. U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to antibodies against polypeptides encoded by a eukaryotic nucleotide sequence that is homologous to a bacterial mismatch repair gene, or to other molecules of the invention. See, for example, "Conjugate Vaccines", Contributions to Microbiology and Immunology, J. M. Cruse and R. E. Lewis, Jr (eds), Carger Press, New York, (1989), the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myesthenia Gravis by toxin-acetylcholine receptor conjugates." Jour. Immun. 133:1335-2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". Immunological Reviews 62:185-216; and Vitetta et al., supra).

Preferred linkers are described in the literature. See, for example, Ramakrishnan, S. et al., Cancer Res. 44:201-208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i)-EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. #21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6[3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physiochemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Antibodies of the present invention can be detected by any of the conventional types of immunoassays. For example, a sandwich assay can be performed in which a polypeptide encoded by a eukaryotic nucleotide sequence that is homologous to a bacterial mismatch repair gene, as provided by the invention, is affixed to a solid phase. A liquid sample such as kidney or intestinal fluid containing, or suspected of containing, antibodies directed against a such a polypeptide of the invention is incubated with the solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art.

DEFINITIONS gene—The term "gene", as used herein, refers to a nucleotide sequence that contains a complete coding sequence. Generally, "genes" also include nucleotide sequences found upstream (e.g. promoter sequences, enhancers, etc.) or downstream (e.g. transcription termination signals, polyadenylation sites, etc.) of the coding sequence that affect the expression of the encoded polypeptide.

wild-type—The term "wild-type", when applied to nucleic acids and proteins of the present invention, means a version of a nucleic acid or protein that functions in a manner indistinguishable from a naturally-occurring, normal version of that nucleic acid or protein (i.e. a nucleic acid or protein with wild-type activity). For example, a "wild-type" allele of a mismatch repair gene is capable of functionally replacing a normal, endogenous copy of the same gene within a host cell without detectably altering mismatch repair in that cell. Different wild-type versions of the same nucleic acid or protein may or may not differ structurally from each other.

non-wild type—The term "non-wild-type" when applied to nucleic acids and proteins of the present invention, means a version of a nucleic acid or protein that functions in a manner distinguishable from a naturally-occurring, normal version of that nucleic acid or protein. Non-wild-type alleles of a nucleic acid of the invention may differ structurally from wild-type alleles of the same nucleic acid in any of a variety of ways including, but not limited to, differences in the amino acid sequence of an encoded polypeptide and/or differences in expression levels of an encoded nucleotide transcript or polypeptide product.

For example, the nucleotide sequence of a non-wild-type allele of a nucleic acid of the invention may differ from that of a wild-type allele by, for example, addition, deletion, substitution, and/or rearrangement of nucleotides. Similarly, the amino acid sequence of a non-wild-type mismatch repair protein may differ from that of a wild-type mismatch repair protein by, for example, addition, deletion, substitution, and/ or rearrangement of amino acids.

Particular non-wild-type nucleic acids or proteins that, when introduced into a normal host cell, interfere with the endogenous mismatch repair pathway, are termed "dominant negative" nucleic acids or proteins.

homologous/homologue—The term "homologous", as used herein is an art-understood term that refers to nucleic acids or polypeptides that are highly related at the level of nucleotide or amino acid sequence. Nucleic acids or polypeptides that are homologous to each other are termed "homologues".

The term "homologous" necessarily refers to a comparison between two sequences. In accordance with the invention, two nucleotide sequences are considered to be homologous if the polypeptides they encode are at least about 50-60% identical, preferably about 70% identical, for at least one stretch of at least 20 amino acids. Preferably, homologous nucleotide sequences are also characterized by the ability to encode a stretch of at least 4-5 uniquely specified amino acids. Both the identity and the approximate spacing of these amino acids relative to one another must be considered for nucleotide sequences to be considered to be homologous. For nucleotide sequences less than 60 nucleotides in length, homology is determined by the ability to encode a stretch of at least 4-5 uniquely specified amino acids.

upstream/downstream—The terms "upstream" and "downstream" are art-understood terms referring to the position of an element of nucleotide sequence. "Upstream" signifies an element that is more 5' than the reference element. "Downstream" refers to an element that is more 3' than a reference element.

intron, exon/intron—The terms "exon" and "intron" are art-understood terms referring to various portions of genomic gene sequences. "Exons" are those portions of a genomic gene sequence that encode protein. "Introns" are sequences of nucleotides found between exons in genomic gene sequences.

sporadic—The term "sporadic" as used herein and applied to tumors or cancers, refers to tumors or cancers that arise in an individual not known to have a genetic or familial pre-disposition to cancer. The categorization of a tumor or cancer as "sporadic" is, of necessity, based on available information and should be interpreted in that context. It is possible, for example, that an individual that inherits a low-penetrance mutation (i.e. a mutation that, statistically, is unlikely to have a dramatic phenotype) will develop cancer as a result of that mutation (i.e. will have had a genetic pre-disposition to cancer) but will have had no family history of cancer. Tumors in that individual might originally be identified as sporadic because the individual was not known to have a genetic pre-disposition to cancer. The term "sporadic", therefore, is used to conveniently describe those tumors or cancers that appear to have arisen independent of inherited genetic motivation, but is not intended to point to defining molecular distinctions between inherited and sporadic tumors or cancers.

affected—The term "affected", as used herein, refers to those members of a kindred that either have developed a characteristic cancer (e.g. colon cancer in an HNPCC lineage) and/or are predicted, on the basis of, for example, genetic studies, to carry an inherited mutation that confers susceptibility to cancer.

The invention will now be further described in the following, non-limiting examples.

EXAMPLE 1

Isolation and Characterization of Yeast Homologues of the *E. coli* mutS Mismatch Repair Gene Materials and Methods Enzymes and chemicals: Restriction enzymes were from New England Biolabs (Beverly, Mass.). T4 DNA ligase was prepared using a method similar to that of Tait et al. 1980. The Klenow fragment of DNA polymerase I and a random primed DNA labeling kit were obtained from Boehringer Mannheim (Indianapolis, Ind.). Taq DNA polymerase was purchased from Perkin Elmer-Cetus (Norwalk, Conn.). Sequenase DNA sequencing kits were from U.S. Biochemical Corp. (Cleveland, Ohio). [a-$^{32}$P]dATP used in random primed labeling and [a-$^{35}$S]dATP used in DNA sequencing were from Amersham (Arlington Heights, Ill.).

Oligonucleotides: Oligonucleotides were synthesized on an Applied Biosystems 380A DNA synthesizer using phosphoramidite chemistry and deprotected using standard methods. Degenerate oligonucleotides for polymerase chain reactions (PCR) were further purified by electrophoresis through a 15% denaturing acrylamide gel followed by purification on a Waters (Milford, Mass.) Sep/Pak column as per the manufacturers' instructions.

Strains and media: The *S. cerevisiae* strain NKY858 (MATa ura3 lys2 leu2::hisG ho::LYS2 his4x) used in this study for the isolation of genomic DNA is derived from SK1 and was the gift of Nancy Kleckner (Harvard University, Cambridge, Mass.). Methods for the construction and manipulation of this strain have been described elsewhere (Tishkoff, Johnson and Kolodner, 1991; Cao, Alani and Kleckner 1990). *E. coli* strain HB101 (Boyer and Roulland-Dussoix, 1969) was the host for the YCP50 library (Rose et al. 1987). *E. coli* strain RK1400 (Symington, Fogarty and Kolodner, 1983) was used as the host for all other plasmids. *E. coli* JM101 was the host for recombinant M13 phage (Messing, 1983). All *E. coli* strains were grown in L broth (LB) with appropriate antibiotics. Strains used for M13 infections were grown in 2xYT (Messing, id. 1983). M13 phage, the YCP50 library and all plasmids were from our laboratory collection.

Plasmids: Plasmids were constructed using standard procedures (Sambrook, Fritsch and Maniatis, 1989). Small scale plasmid preparations were performed by the boiling method of (Holmes and Quigley, 1981). Large scale plasmid preparations were prepared by a modification of the Triton-lysis method with subsequent purification of form-1 plasmid DNA by centrifugation in CsCl-ethidium bromide density gradients (Sambrook, Fritsch and Maniatis, 1989) DNA for double-stranded DNA sequencing was purified using two cycles of CsCl-EtBr density gradient centrifugation. Preparation of single-stranded M13 DNA for sequencing was essentially by the polyethylene glycol precipitation method (Messing, 1983). *E. coli* transformation procedures used were based on a standard Mg—Ca transformation procedure (Wensink et al., 1974).

PCR amplification products of the MSH1 (SEQ ID NO.:2) and MSH2 (SEQ ID NO.:1) genes were inserted into the BamH1 site of M13mp19 to generate M13mp19-39 and M13mp19-45, respectively. These inserts will be referred to as ms351-I and ms351-II for convenience. pIA5 (containing MSH1) contains a Sau3A partial digest fragment from chromosome VIII of *S. cerevisiae* inserted into the BamHI site of YCP50. pII-2 (containing MSH2) contains a Su3A fragment from chromosome XV of *S. cerevisiae* inserted into the BamHI site of YCP50. These two plasmids and their less well characterized overlapping clones were recovered from the library constructed by ROSE et al. (1987).

PCR techniques: Based upon protein sequence comparisons, the following three regions of protein sequence were selected and used to design the indicated degenerate oligonucleotides: (1) F(A/V)THY, 5'-CTGGATCC(G/A)TG(G/A/T/C)GT(G/A/T/C) (G/A)C(G/A)AA-3' [SEQ ID NO.:11]; and (2) TGPNM, 5'-CTGGATCCAC(G/A/T/C)GG (G/A/T/C)CC(G/A/T/C)AA(T/C)ATG-3' [SEQ ID NO.:12].

The sequence CTGGATCC at the 5' end of each oligonucleotide is a BamHI restriction enzyme cleavage site added to facilitate cloning of the amplification product. PCR was performed in 50 µl volumes containing 10 mM Tris, pH 8.3, 3 mM MgCl$_2$, 50 mM KCl, 0.01% gelatin, 1.0 unit of Taq DNA polymerase, 25 pmol of each degenerate primer and 1 µg of yeast chromosomal DNA. The cycle for amplification using these degenerate oligonucleotides was as follows: (1) denaturation 1 min, 94°; (2) annealing 2 min. 550; (3) polymerization 20 sec. 72°. The reaction was continued for 30 cycles. PCR amplification products for cloning were digested with BamHI and passed over a Sephadex G-50 column run in 10 mM EDTA pH 8.0 to remove linkers and primers.

Colony hybridizations: Colonies were grown overnight on LB plates, lifted off onto Genescreen (Du Pont) and autoclaved at 1200 for 2 min. The filters were washed in 40 mM NaHPO$_4$ buffer, pH 7.2, at 65° until all cellular debris was removed. Hybridization was conducted under stringent conditions well known in the art, for example, the hybridization reaction contained: 0.5 M NaHPO$_4$ buffer, pH 7.2, 0.5% w/v bovine serum albumn, 1 mM EDTA, 5% sodium dodecyl sulfate (SDS) and 0.5 µg (10$^8$ cpm/µg) of $^{32}$P-labeled probe made from the M13mp19 containing the appropriate 351-bp PCR product insert by the random priming method of Feinberg and Vogelstein (1983). Hybridization was allowed to proceed overnight at 60° followed by four 30-min washes with 40 mM NaHPO$_4$ buffer, pH 7.2 1 mM EDTA and 1% SDS at 65°. Filters were exposed to x-ray film to detect the hybridizing colonies.

Southern hybridization analysis: DNA was transferred from agarose gels to Genescreen membrane (Du Pont) in 25 mM NaHPO$_4$ buffer, pH 6.5, and UV cross-linked to the membrane (Church and Gilbert, 1984). Hybridization was performed as described above except washes were done for 30 minutes with a solution containing 2×SSC and 1% SDS at 65° with constant agitation. The hybridizing DNA bands were then detected by autoradiography.

DNA sequencing: Single-stranded M13 and double-stranded plasmid DNAs were sequenced by the dideoxychain termination method using Sequenase and the protocols supplied by the manufacturer. Double-stranded sequencing templates were prepared as follows: covalently closed circular template DNA was denatured in 0.2 M NaOH, 0.2 mM EDTA for 30 min at 370. The mixture was neutralized with 0.1 volume of 3 M sodium acetate, pH 4.5, the DNA precipitated with 4 volumes of ethanol and resuspended in 5 mM Tris, pH 7.5, 0.5 mM EDTA. The Mn$^{2+}$ sequencing buffer supplied by the manufacturer was used to determine DNA sequences close to the primer. The DNA sequences reported here have been submitted to GenBank under accession numbers M84169 for SEQ ID NO.:1 [MSH2] and M84170 for SEQ ID NO.: 2 [MSH1].

Sequence analysis: Homology searches and alignments were performed using the Eugene program (Lark Sequencing Technologies, Ltd., Houston, Tex.) run on a Sun Microsystems Sparkstation 1. Sequence alignment of the various mutS homologues was performed by subdividing the sequence into smaller blocks of homology. The anchor points of these smaller domains were chosen based on the Lawrence homology search (Lawrence and Goldman, 1988), which defines homology domains between peptide sequences. The Dayhoff cost matrix of the Lawrence homology search was used which reports a minimum homology domain of 10 residues with a minimum acceptable standard deviation from chance of 3.0. Once regions of sequence were anchored by homology domains, the Altschul program (Altschul and Erickson, 1986) was used to compute a globally optimal alignment using the SS2 algorithm. Both the Dayhoff and the genetic distance cost matrices were used with the Altschul program (Altschul and Erickson, id.). The penalty for gap opening was either 1.5 or 2.0 and the incremental penalty for each null in the gap was 1.0.

The amino-terminal 21 amino acids of SEQ ID NO.: 1 were analyzed in detail to identify features associated with mitochondrial targeting sequences. The presence of sequences with the potential to form amphophilic helices was determined using the analysis of Von Heijne (1986). Estimations of hydrophobic moment, maximal hydrophobicity and surface seeking potential % surf and surf(E) were performed using the methods of Eisenberg, Weiss and Terwilliger (1984) and Eisenberg et al. (1984). The normalized consensus scale (Eisenberg, Weiss and Terwilliger supra) was used in all calculations of hydrophobicity as follows: R=–2.53, K=–1.50, D=–0.90, Q=–0.85, n=–0.78, E=–0.74, H=–0.40, S=–0.78, T=–0.05, P=0.12, Y=0.26, C=0.29, G=0.48, A=0.62, M=0.64, W=0.81, L=1.06, V=1.08, F=1.19, I=1.38. References: Altshul, S. F., and B. W. Erickson, Bull. Math. Biol. 48:603-616. 1986; Boyer, H. W., and D. Roulland-Dussoix, coli. J. Mol. Biol. 41:459-472. 1969; Cao, L., Alani, E. and N. Kleckner, Cell 61:1089-1101. 1990; Church, G. M., and W. Gilbert, Proc. Natl. Acad. Sci. USA 81:1991-1995. 1984; Eisenberg, D., R. M. Weiss and T. C. Terwilliger, Proc. Natl. Acad. Sci. USA 81:140-144. 1984; Eisenberg, D., E. Schwarz, M. Komaromy and R. Wall, J. Mol. Biol. 179:125-142. 1984; Feinberg, A. P., and B. Vogelstein, Anal. Biochem. 132:6-13. 1983; Holmes, D. S., and M. Quigley, Anal. Biochem. 114:193-197. 1981; Lawrence, C. B., and D. A. Goldman, Comput. Appl. Biosci. 4:25-31. 1988; Messing, J., Methods Enzymol. 101:10-77. 1983; Rose, M. D., P. Novick, J. H. Thomas, D. Botstein and G. R. Fink, Gene 60:237-243. 1987; Sambrook, J., E. F. Fritsch and T. Maniatis, Cold Spring Harbor, N.Y. 1989; Symington, L. S., L. M. Fogarty and R. Kolodner, Cell 35:805-813. 1983; Tait, R. C., R. L. Rodrigues and R. W. West, J. Biol. Chem. 255:813-816. 1980; Tishkoff, D., A. W. Johnson and R. Kolodner, Mol. Cell. Biol. 11:2593-2608. 1991; Von Heijne, G., 5:1335-1342. 1986; Wensink, P. C., D. J. Finnegan, J. E. Donelson and D. S. Hogness, Cell 3:315-325. 1974.

EXAMPLE 2

Function of Yeast Homologues of the *E. Coli* mutS Mismatch Repair Gene

Enzymes and chemicals: Chemicals, enzymes and oligonucleotides are as described above in Example 1.

Strains and media: The *S. cerevisiae* strains used in this study are derived from SK1 and were the gift of Nancy Kleckner (Harvard University, Cambridge, Mass.). Methods for the construction and manipulation of these strains have been described elsewhere (Tishkoff, Johnson and Kolodner 1991; Cao, Alani and Kleckner 1990). The two strain combinations NK859: MA Ta ho::LYS2 lys2 ura3 leu2::hisG his4x and NK860: MA Ta ho::LYS2 lys2 ura3 leu2::hisG his4b or NK858: MATa ho::LYS2 lys2 ura3 leu2::hisG his4x and NK861: MATa ho::LYS2 lys2 ura3 leu2::G his4b were crossed to construct the diploids used for all MSH gene disruptions. Haploid strains bearing the MSH gene insertion mutations in combination with a particular HIS4 allele were generated as needed from the disruption heterozygotes and used for phenotypic characterization or constructing diploids homozygous for the insertion mutations. This was done as a precaution, assuming the disruption mutants might be mutators. The his 4b and his4x alleles used in these studies are four base insertion mutations (Cao, Alani and Kleckner 1990). Wild-type HIS4 alleles were generated from the above mentioned strains by selection on media lacking histidine. All strains described in this work are derived from these starting strains by transformation and are therefore isogeneic. Canavanine plates lacked arginine and contained 30 µg/ml canavanine. The nonfermentable carbon source plates used here were both YPAcetate (YPAc) and YPGlycerol (YPgly) formulated as described by Sherman, Fink and Hicks (1986). Other yeast and *E. coli* media were as described above in Example 1. The *E. coli* strain RK1400 (Symington, Fogerty and Kolodner (1983) was used for all plasmid constructions. Strains used for transposon mutagenesis are described below.

Plasmids: Plasmids were constructed using the materials and standard procedures outlined above in Example 1. The plasmid pNk1206 was obtained from Nancy Kleckner (Huisman and Kleckner 1987). The Tn10LLK construct was made as follows. Yep 13 DNA (Broach, Strathern and Hicks 1979) was digested with Bg/II and the 2.6-kb fragment harboring the LEU2 gene was isolated. This fragment was then inserted into the BamHI site located between the lacZ and $kan^R$ sequences of Tn10LK of pNK1206 to yield pTN10LLK (Lac Leu Kan). The orientation of the Bg/II fragment in the BamHI site has not been determined. In order to transform yeast and replace the URA3 marker of the Tn10LUK insertion by recombination with TN10LLK containing a LEU2 marker, pTn 10 LLK was digested with Bc/l and NruI and the DNA used directly in LiCl transformation (ITO et al. 1983). Bcl and NruI cleave pTN10LKK at sites in the lacZ and $kan^R$ sequences, respectively.

Transposon mutagenesis: Plasmids pI-A5 and pII-2 (Reenan and Kolodner 1992) were transformed into NK5830/pNK629 (Huisman and Kleckner 1987) selecting for ampicillin (pI-A5 and pII-2) and tetracycline (pNK629) resistance and then mutagenized with Tn10LUK by infection with phage lambda 1224 following a method similar to Huisman and Kleckner (1987). The resulting pools of mutagenized plasmid DNA were used to transform NK8017 (Huissman and Kleckner 1987) and plasmid DNA was isolated from individual transformants (Holmes and Quigley 1981). An individual mutant plasmid DNA was isolated from each pool to assure independence of insertions. Insertions into the desired fragments were then identified by restriction mapping. These insertion mutations were then introduced into their homologous location in the yeast genome using the one step transplacement method (Rothstein 1991).

Growth Protocols for MSH2/MSH2 Viability Experiments:
Minimal Vegetative Growth Regimen:

Two wild-type or msh2::TN10LUK haploids were mated and single colonies (>3 mm) were isolated on rich medium (YPD). These diploid colonies were used to inoculate 5 ml of presporulation medium (YPAc) at low cell density and growth was allowed to proceed to saturation. The culture was then washed with sporulation medium and then incubated for 24 hr in sporulation medium.

Zero growth regimen: Haploid strains were patched onto rich medium (YPD) directly from frozen stocks and allowed to grow overnight. Haploids of opposite mating-type were suspended in liquid YPD, mixed and plated back onto a YPD plate. The mating was allowed to proceed for 4 hr on rich medium and then the mating mixture was transferred directly to sporulation medium, allowing no vegetative growth. Sporulation was allowed to proceed for 24 hr.

Determination of mutation and recombination rates: Mutation rates were determined by a fluctuation test and two or three independent experiments were performed for each strain tested (Lea and Coulsen 1949). Strains to be tested were plated for single colonies at 30° on YPD plates. Eleven single colonies (>3 mm) were excised from the plate and resuspended in sterile water. Appropriate dilutions were then plated to determine the number of viable cells and canavanine resistant cells per culture and these data were analyzed by the method of Lea and Coulsen (1949). Using this method, $r_o$=M (1.24+1 n M) where $r_o$ is the median number of canavanine-resistant colony-forming units per culture among the 11 plantings and M is the average number of canavanine-resistant mutations per culture. M was solved by interpolation and then used to calculate the mutation or recombination rate, r=M/N where N is the final average number of viable cells per plating.

Meiotic recombination was measured by determining the frequency of His+ cells present before and after sporulation of individual cultures of cells. Strains were grown to an $OD_{600}$ of 0.5 in YPD and then washed with presporulation medium (YPAc) twice. These cells were resuspended at low density in YPAc ($OD_{600}$ of 0.0025) and growth was continued until an $OD_{600}$ of 1.0 was reached. The cells were then washed twice in sporulation medium and resuspended in sporulation medium. These cells were at the 0 time point and were sonically disrupted and plated on plates lacking histidine and minimal complete plates to determine the frequency of recombinants. The remaining cells were allowed to sporulate for 20 hr and analyzed as described above. The frequency of His+ cells before and after induction of meiosis is given.

Disruptions of SEQ ID NO.: 2 [MSH1]: Sporulation of diploids heterozygous for the msh1::Tn10 LUK4-2 insertion showed 2:2 segregation for a small scalloped colony phenotype when tetrads were dissected onto rich medium (YPD). This phenotype was found to be associated with a petite phenotype, as all such colonies failed to grow when they were replica plated to plates containing the nonfermentable carbon sources glycerol (YPgly) or acetate (YPAc). The petite phenotype associated with the msh1::Tn10LUK4-2 mutation was recessive. The initial disruption heterozygotes were not petite, and subsequent matings of petite haploid msh1::Tn10LUK4-2 mutants to wild-type yielded diploids that could grow on YPgly plates and could be streaked to yield single colonies on YPgly plates. The behavior of msh1 petites in crosses with wild-type strains under nonselective conditions will be discussed below.

Mitochondrial DNA was prepared from five haploid msh1 petite spore colonies obtained directly from sporulation of a heterozygote. The petite mtDNAs and a wild-type mtDNA control were digested with HindIII and analyzed by agarose gel electrophoresis. Two of the msh1 petite mtDNAs gave the same restriction pattern as wild type. In these two cases, the petite phenotype may be due to point mutations or possibly small deletions or rearrangements in the mtDNA that could not be detected in this analysis. The other three petites gave a restriction pattern in which some wild-type fragments were missing and additional novel fragments were present. All three rearranged mtDNA restriction patterns observed were similar. In one case, a petite mutant containing rearranged mtDNA and another petite mutant containing un-rearranged mtDNA were obtained from the same tetrad. The proportion of spore clones obtained containing these large scale mtDNA rearrangements is similar to the proportion of spore clones that were hypersuppressive petites. This is consistent with the observation that the hypersuppressive petites often contain large scale rearrangements of mtDNA (Dujon 1981).

4',6-Diamidino-2-phenylindole (DAPI) staining of mtDNA in msh1 mutants: Wild-type and msh1::Tn10LUK3-3 haploid strains were grown on rich medium (YPD) and subjected to DAPI staining and photographed. In wild type, the mtDNA appeared as small dispersed patches of staining throughout the cytoplasm. In msh1 mutants the only fluorescence other than that in the nucleus appeared as larger patches, sometimes only one or two per cell and occasionally reaching ~20% the size of the nucleus. This altered mtDNA distribution may be a result of abnormal morphology and distribution of mitochondria in petite mutants rather than an actual reflection of a DNA metabolic defect.

Disruptions of SEQ ID NO.: 1 [MSH2]: Disruptions of SEQ ID NO. 1 in the plasmid pII-2 were isolated as described above. When necessary, the msh2::Tn10LUK disruptions were converted to Tn10LLK disruptions as described above. Sporulation and subsequent dissection of diploids heterozygous for the msh2 insertion mutations always yielded four equal sized spore clones indicating that msh2 mutations did not have an obvious effect on cell growth.

Rate of spontaneous mutation to canavanine resistance in msh2 mutants: The spontaneous mutation rate to canavanine resistance, was determined by fluctuation analysis of the disruption mutant msh2::Tn10LUK7-7, was elevated 70-100-fold over that of wild type. This increased level of spontaneous mutation was easily visualized by patching out spore clones and replica plating to canavanine plates. Using this test to analyze the segregation of both the mutator phenotype and msh2 mutations indicated that the mutator phenotype always segregated with the msh2 disruption mutation.

References: Broach, J. R., J. N. Strathern and J. B. Hicks, Gene 8:121-133. 1979; Cao, L., E. Alani and N. Kleckner, Cell 61:1089-1101. 1990; Dujon, B., Cold Spring Harbor Laboratory, Cold Spring Harbor, N.Y. 1981; Holmes, D. S., and M. Quigley, Anal. Biochem. 114:193-197. 1981; Huisman, O. and N. Kleckner, Genetics 112:409-420. 1987; Ito, H., Y. Fukuda, K. Murata and A. Kimura, J. Bacteriol. 153:163-168. 1983; Lea, D. E., and C. A. Coulson, J. Genet. 49:264-285. 1949; Reenan, R. A. G., and R. D. Kolodner, Genetics 132:963-973. 1992; Rothstein, R., Methods Enzymol. 194:281-302. 1991; Sherman, F., G. R. Fink and J. B. Hicks, Cold Spring Harbor Laboratory, Cold Spring Harbor, N.Y. 1986; Symington, L. S., L. M. Fogarty and R. Kolodner, Cell 35:805-813. 1983; Tishkoff, D., A. W. Johnson and R. Kolodner, Mol. Cell. Biol. 11:2593-2608. 1991

EXAMPLE 3

Isolation and Characterization of a Human Homologue of the *E. coli* mutS Mismatch Repair Gene Materials and Methods Chemicals, Enzymes, Oligonucleotides, DNAs, Libraries and Vectors Ultrapure Tris (acid and base), Ethylenediaminetetraacetic acid (EDTA), $MgCl_2$, $MgSO_4$, NaCl, and analytical grade sodium citrate, KCl, potassium phosphate monobasic ($KH_2PO4$) and sodium phosphate dibasic ($Na_2HPO4$) were obtained from Amresco (Solon, Ohio). Ultra pure glycerol was obtained from Mallinckrodt, Inc. (Paris, Ky.). Deoxyribonucleoside triphosphates and ATP were purchased from Pharmacia LKB Biotechnology, Inc. (SWEDEN). NIGMS mapping pannel 2 DNAs were from Coriell Cell Respositories (Camden, N.J.) and a Southern transfer of a BamHI digest of these DNAs used in preliminary experiments was from Oncor (Gaithersburg, Md.). Gelatin was purchased from Sigma (St. Louis, Mo.). Restriction endonucleases and T4 DNA Ligase were purchased from New England Biolabs, Inc. (Beverly, Mass.). Calf Intestinal Phosphatase was purchased from New England Biolabs, Inc. (Beverly, Mass.). Taq polymerase was purchased from Perkin Elmer-Cetus (Norwalk, Conn.). [$\alpha^{-32}P$]-dCTP was purchased from Amersham (Arlington Heights, Ill.). Oligonucleotides were synthesized on an Applied Biosystems 394 DNA synthesizer and were deprotected and purified by standard methods. PCR products were inserted into BamH1 digested Bluescript SK+ vector DNA (Stratagene, La-Jolla, Calif.) using standard methods.

Isolation of the MSH2$_{hu}$ cDNA clone (SEQ ID No. 8) was done by screening a Hela S3 cDNA library constructed in the UniZap vector system (Stratagene, La Jolla, Calif.). Plating and screening the library was performed according to the manufacturers recommendations.

Cloning Human Nucleotide Sequences that are Homologous to the E. coli mutS Gene Using Degenerate PCR Degenerate oligonucleotides that would hybridize to DNA encoding two highly conserved regions of the known bacterial mutS and hexA and S. cerevisiae MSH proteins were designed. The following amino acid regions were selected: primer 1a.) FATH(F/Y) (noncoding strand) 5'-CGCGGATCC (G/A)(A/T)A(G/A)TG(G/A/T/C)GT(G/A/T/C)(GC(G/A) AA-3' (SEQ ID NO.: 13); primer 1b.) FTTH(F/Y) (noncoding strand) CGCCGATCC(G/A)(A/T)TG(G/A/T/C)GT(G/A/T/ C)GT(G/A/T/C)GT(G/A) AA-3' (SEQ ID NO.:14); primer 1c.)FVTH(FY) (noncoding strand) CGCGGATCC (G/A)(A/ T)A(G/A)TG (G/A/T/C)GT(G/A/T/C)AC(A/G/)AA-3' (SEQ ID NO.: 28 and primer 2.) TPGNM (coding strand) 5'-CTGGATCC AC(G/A/T/C)GG(G/A/T/C)CC(G/A/T/C) AA(T/C)ATG-3' (SEQ ID NO.: 12). The CGCGATCC sequence at the 5' end of each oligonucleotide is the BamHI restriction enzyme cleavage site added to faciliate cloning of the amplification product into the Bluescript SK+vector. PCR amplification of known mismatch repair sequences from yeast genomic DNA was used to optimize the PCR conditions using primer 2 paired with either primer 1a, 1b or 1c. PCR was performed in a 50 μl volume containing 10 mM Tris (pH 8.3), 50 mM KCl, 0.1% gelatin, 200 uM each dGTP/dATP/ dTTP/dCTP, 1 unit Taq DNA polymerase and 25 pmol of each degenerate primer. Multiple concentrations of MgSO$_4$ were tested (1 mM, 3 mM, 5 mM and 10 mM) for each primer pair as well as multiple concentrations of yeast genomic DNA or human cDNA (10 ng, 10 ng and 1 ug). cDNA was prepared using the mRNA Purification Kit (Parmacia, SWEDEN) from HPB-ALL cells (Moore and Fishel, J. Biol. Chem. 265: 11108-11117, 1990). The optimal method for amplification using these degenerate oligonucleotides on cDNA was found to be 35 cycles of a.) denaturation 1 min, 94° C.; b.) annealing 2 min, 45° C.; c.) polymerization 5 min, 72° C.

After electrophoretic analysis of the products on a 2% agarose gel run in 45 mM Tris (pH 8.0), 5 mM sodium acetate, 2 mM EDTA (TAE), reactions that were deemed to contain products of the expected size (∝360 bp) were extracted with buffered phenol, precipitated in ethanol and fractionated on a preparative 2% agarose TAE gel containing 0.5 μg/ml Ethidium Bromide (Sigma, St. Louis, Mo.). The DNA band of interest was then isolated from the gel using NA45 paper essentially as described by the manufacturer (Schleicher and Schuell, Keene, N.H.) with the modification that the DNA was eluted from the NA45 paper by incubation at 70° C. for 1 hr in 300 μl of 1 mM NaCl, 50 mM Arginine (free base). The elution solution was removed and extracted with buffered phenol and the DNA precipitated with ethanol. This isolated DNA fragment was digested with BamHI and reisolated from a 2% agarose TAE gel using NA45 paper as described above to remove the linker. The Bluescript SK+ vector was digested with BamH1, treated with 20 units Calf Intestinal Phosphatase in a 50 ul reaction and isolated from a 1% agarose gel using NA45 paper as described above.

The isolated DNA fragment (20 ng) and Bluescript vector (200 ng) were added to a ligation reaction (100 μl) containing 50 mM Tris (pH 7.8), 8 mM MgCl$_2$, 5 mM βMercaptoethanol, 67 μM ATP and 40 units T4 DNA ligase, incubated at 12.5° C. for 16 hr and then the DNA was transformed into E. coli XL1-blue (Stratagene, La Jolla, Calif.) by the standard Mg—Ca transformation procedure (Wensink, et al., 1974).

Small scale preparations of plasmid DNA (Sambrook, et al., supra 1989) from individual transformants were analyzed for the presence of the appropriate sized insert (∝360 bp), and ten such clones generated with each primer pair were analyzed by double-stranded DNA sequencing. We found one MSH2 homologue among the 10 clones generated with the 1a plus 2 primer pair and this plasmid was designated pDHA 22. We found no MHS2 homologue among 22 clones generated with the 1b plus 2 and 1c plus primer pairs. The PCR fragment was designated 22.1 (SEQ. ID No.: 15)

The MSH2 homologue sequence contained in pDHA22 was used as a probe to screen a human cDNA library (UniZap Hela S3 cDNA, Stratagene, LaJolla, Calif.) according to the manufacturers recommendations. Oligonucleotide primers (#15998-5'GTGATAGTACTCATGGCC; SEQ ID NO.: 23 and #15607-5'AGCACCAATCTTTGTTGC; SEQ ID NO.: 17, minus BamHI site) were designed to hybridize to nucleotides inside the degenerate primer sequences on both ends of the MSH2 sequences present in pDHA 22. A 278 bp fragment was amplified by PCR using these primers and purified using NA45 as described above.

A radiolabelled probe was made by performing 25 cycles of PCR using cycles of a) denaturation 1 min, 94° C.; b) annealing 2 min, 50° C., c) polymerization 2 min, 72° C. with a 50 μl reaction containing 1.5 mM MgSO$_4$, 10 ng of the isolated 278 bp fragment, 200 μM each dATP/dGTP/dTTP, 25 pmol each of the two primers #15998 and #15607, and 100 μCi α-($^{32}$P)-dCTP (5000 ci/mmol). Unincorporated nucleotides were removed by chromatography on a Nick Column (Parmacia, SWEDEN), the probe denatured by boiling for 5 min and $10^7$-$10^8$ total dpm used to probe Hybond N+ filters (Amersham, Arlington Heights, Ill.) containing A UniZap Hela S3 cDNA plate lifts (one million members). Two additional screens were carried out to isolate a homogenerous λ UniZap Hela S3 cDNA phage population and the insert rescued using the R408 helper filamentous phage as described by the manufacturer (Stratagene, La Jolla, Calif.). One positive clone containing a large 3111 bp cDNA insert with a 2727 bp open reading frame homologous to as characterized by DNA sequencing and designated pDHA 11. The sequence of the cDNA clone is presented as SEQ ID NO.:8. A plasmid containing this human cDNA clone has been deposited with the American Type Culture Collection (ATCC) on Jan. 26, 1994 in accordance with the Budapest Treaty as ATCC number 75647. The sequence of this clone has also been deposited with GenBank and has GenBank Accession No. U03911.

This human cDNA clone (SEQ ID NO.:8) contains a complete open reading frame capable of encoding 934 amino acids. The 0.25 encoded amino acid sequence is presented as SEQ ID NO.:16. The polypeptide of SEQ ID NO.:16 shows 41% overall identity with the protein of SEQ ID NO.:3 (the yeast Msh2 protein). The most conserved region, amino acids 657 to 788 of SEQ ID NO.:16, is about 81% identical to the corresponding region (amino acids 676 to 807) of the yeast protein of SEQ ID NO.:3. In particular, the human protein of SEQ ID NO.:16 contains the sequence TGPNM (SEQ ID NO.:5) from amino acid 668 to 672 and the sequence FATHF (SEQ ID NO.:6) from amino acids 780 to 784. Thus, by the criteria outlined above, the identified human cDNA sequence is homologous to the E. coli mutS gene and the yeast genes of SEQ ID NOs.:1 and 2. Moreover, the human nucleotide sequence of SEQ ID NO.:8 a homologue of the E. coli mutS gene. The protein of SEQ ID NO.:16, which is encoded by the nucleotide sequence of SEQ ID NO.:8, is a protein homologue of the E. coli MutS mismatch repair protein.

The human protein of SEQ ID NO.:16 is also a homologue of the yeast protein of SEQ ID NO.: 3 (Msh2), with which it shows a particularly high degree of homology. The human protein of SEQ ID NO.: 16 is therefore termed "human Msh2". Likewise, the human gene that encodes this protein (corresponding to SEQ ID NO.:8) is referred to as $MSH2_{hu}$.

DNA Sequence Analysis: DNA sequencing of double-stranded plasmid DNAs was done with an Applied Biosystems 373A DNA sequence using standard protocols and dye labeled dideoxy nucleoside triphosphates as terminators (Sanger et al Proc. Nat. Acad. Sci., USA 74:5463-5467, 1977, Smith et al. Nature 321:674-679, 1986. NCBI-GenBank release 78, PIR release 37 and SWIS-PROT release 26 database searches were performed at the National Center for Biotechnology Information using the BLAST network service. Sequence alignments were performed using DNAStar MegAlign using the Clustal method. Multiple alignment parameters were Gap Penalty=10 and Gaplength Penalty=10. Pairwise alignment parameters were Ktuple=1, Gap Penalty=3, Window=5 and Diagnols saved=5. The Phylogenetic Tree was also constructed using DNA Star MegAlign.

Southern Hybridization: NIGMS mapping panel-2 DNAs were digested with EcoRI and 10 μg of the resulting genomic FNA fragments were separated by electrophoresis through a 1% agarose gel run in TAE buffer. Southern transfer was performed according to Sambrook, et al., (supra) onto Hybond N+ paper. Probe was prepared using the PCR method described above except primers were used that amplify the full length $MSH2_{hu}$ fragment. We have found that this probe identifies EcoRI fragments containing the largest exons but does not identify all of the genomic EcoRI fragments containing MSH2 exons, presumably because of under representation in the probe of some MSH2 sequences from the central portion of the insert.

PCR Mapping: PCR was used to detect MSH2 sequences in the NIGMS mapping panel of DNAs using primers #16388-5'GTTTTTCCTTTCATCCGTTG (SEQ ID NO.: 21) and #16389-5'AAACTAGCCAGGTATGG (SEQ ID NO.: 22) that amplify a predicted 158 bp fragment of MSH2 contained in an intron located at nucleotide position 2020 of the cDNA sequence. 25 μl PCR reactions contained 10 mM Tris buffer pH 8.5, 50 mM KCl, 3 mM $MgCl_2$, 0.01% gelatin, 50 μM each dGTP/daTP/dTTP/dCTP, 1.5 unit Taq DNA polymerase, 5 pmole each primer and 0.5 μg each DNA sample. PCRM was performed for 30 cycles of a) denaturation 30 sec, 94° C.; b) annealing 30 sec, 55° C., c) polymerization 1 min, 72° C. and 3 μl of each reaction was analyzed by electrophoresis through a 1.4% agarose gel run in TAE buffer.

Mutator Assay: The rate of spontaneous mutation to $rif^r$ in wild type *E. coli* AB1157 (F, thr1, leu6, thi1, lacY1, galK4, aral14, xy15, mtl1, proA2, his4, argE3 str31, tsx33, supE44, λ⁻) was determined using a plate assay. The $Msh2_{hu}$ containing Bluescript (stratagene, La Jolla, Calif.) plasmid derivative pDHA 11 was transformed into AB1157 according to Fishel, et al., (J. Mol. Biol. 188:147-157, 1986). Ampicillin resistant transformants were selected and grow to saturation in LB containing 100 μg/ml Ampicillin (AMP) and 0.5 mM IPTG. Dilutions of this culture were plated on LB plates containing 100 μg/ml AMP to determine the total number of viable cells containing the pDHA 11 plasmid, and LB plates containing 100 μg/ml AMP plus 100 μg/ml rifampicin (Sigma, St. Louis, Mo.) to determine the total number of spontaneous $rif^r$ mutants in the culture. The rate of mutation was calculated according to Lea and Coulson (J. Genet. 49:264-285, 1949) J. Genet. 49:264-285) using $r_o=M(1.24+\ln M)$, where $r_o$ is the median number of $rif^r$ mutations in an odd number of independent cultures (usually 15) and M is the average number of $rif^r$ mutations per culture. M was solved by interpolation from the known $r_o$ value and then used to calculate the mutation rate r, where r=M/N, where N is the final average number of viable cells.

Isolation of a Human Genomic DNA Clone

Several different probes, including PCR generated clone 22.1 and the human cDNA clone described above, were used to screen a λgt11 human genomic library provided by L. Kunkel. Any human genomic library could be screened.

Nine clones containing nucleotide sequences that are homologous to SEQ ID NOs.:1 and 2, and the bacterial mutS and hexA genes were identified. Standard restriction mapping and sequencing protocols revealed 7 exons and associated intron junctions.

Now that the exact sequence of the human cDNA clone, and of portions of the corresponding genomic sequence, are known, one skilled in the art can readily design PCR primers to amplify particular sections of those sequences. For example, SEQ ID NOS.:25/26, 29/30, 31/32, 33/34, 35/36, 37/38 and 39/40 are oligonucleotide primer pairs that can be used to amplify individual exons of the human gene.

Because the genomic clones identified contain nucleotide sequences capable of encoding only forty-eight percent (48%) of the C-terminal end of the protein encoded by the human cDNA clone described above (SEQ ID NO.: 8), two new probes were generated using PCR with primers designed based on N terminal sequences of SEQ ID NO.:8 and were used to rescreen the genomic library. One probe identified 6 clones, together containing nucleotide sequences capable of encoding the N-terminal fifty-six percent (56%) of the protein encoded by the human cDNA clone (SEQ ID NO.: 8) described above. The other probe identified 2 clones, together containing nucleotide sequences capable of encoding the N-terminal thirty-one percent (31%) of the protein encoded by the human cDNA clone (SEQ ID NO.:8) described above.

Genetic Mapping of Human Clones

The isolated human nucleotide sequences described above were mapped in the human genome.

The PCR-generated clone number 22.1 (SEQ ID NO.:15) was used to probe Southern blots of genomic DNA isolated from human-chromosome-specific hamster and mouse cell hybrids. In particular, we used PCR-generated SEQ ID NO.: 15 to screen Mapping Panel 2, a set of cell hybrids assembled by the National Institutes of Health, Institute of General Medical Science (Bethesda, Md.). Mapping Panel 2 consists of 27 different genomic DNA samples: a sample of human genomic DNA, a sample of chinese hamster genomic DNA, a sample of mouse genomic DNA, and samples of genomic DNA from each of 24 different mouse or hamster cell hybrids that contain a single human chromosome (1-22, X, or Y). Blots of both EcoRI-digested and BamHI-digested DNA samples from the Mapping Panel were probed. The results indicated that PCR-generated probe number 22.1 (SEQ ID NO.:15) hybridizes to nucleotide sequences present in the DNA isolated from cell hybrids containing human chromosome 2.

The human cDNA clone shown in SEQ ID NO.:8 was also used to probe Southern blots of human genomic DNA and of DNA isolated from chinese hamster cell hybrids containing human chromosome 2. DNA samples were provided by Coriell Cell Repositories, Camden, N.J., Again, hybridization to human chromosome 2 was observed.

This mapping was further confirmed in PCR reactions performed on DNA populations isolated from Mapping Panel 2 and from the DNA samples provided by Coriell Cell Repositories, Camden, N.J. The primers used, whose sequences are presented as SEQ ID NOS.:21 and 22, specifically amplify a predicted 158 bp fragment of the human genomic homologue Msh2$_{hu}$, located in an intron site at nucleotide position 2020 of the cDNA clone (SEQ ID NO.:8). PCR products were only observed in those reactions that contained human chromosome 2.

This localization to human chromosome 2 suggests that the human gene corresponding to SEQ ID NO.:8 is the gene associated with HNPCC.

Characterization

Expression in *E. coli* of a MutS homologue from a different bacterial species (e.g. the hexA protein of *S. pneumoniae*) interferes with the MutHLS mismatch repair pathway, resulting in a dominant mismatch-repair-defective phenotype (Prudhomme et al. J. Bacteriol. 173:7196-7203, 1991). Conceivably, the *S. pneumoniae* MutS homologue binds to mismatched base pairs in *E. coli* but cannot interact with the rest of the *E. coli* mismatch repair machinery and thus disrupts normal mismatch repair.

In order to test the possibility that the human protein of SEQ ID NO.:16 can play a functional role in mismatch repair, we tested whether expression of that human protein in *E. coli* results in a dominant mismatch-repair-defective phenotype. In particular, we asked if *E. coli* cells expressing the human protein of SEQ ID NO.:16 showed an increased rate of spontaneous mutation to rifampicin resistance (see Example 3). Plate assays and fluctuation analysis (Lea and Coulson J. Genet. 49:264-285, 1949, incorporated herein by reference) revealed that *E. coli* strains expressing the human protein of SEQ ID NO.:16 show an approximate 10-fold increase in spontaneous mutation to rifampicin resistance over the rate observed in isogenic *E. coli* strains that do not express the human protein. This result is consistent with the idea that the human protein of SEQ ID NO.: 16 functions in DNA mismatch repair. In particular, it seems likely that the human protein, like the other known MutS homologues (including the yeast proteins of SEQ ID NOs.:3 and 4), can bind to mismatched nucleotides, but that it cannot interact with the other components of the *E. coli* mismatch repair pathway.

This phenotypic analysis, when combined with the mapping studies discussed above, strongly suggests that the human gene corresponding to SEQ ID NO.:8 is the gene responsible for conferring susceptibility to HNPCC. Furthermore, this type of analysis can be used to identify fragments and variants of the human protein of SEQ ID NO.:16, or other eukaryotic homologs of the *E. coli* mutS gene, that are functionally equivalent to the full-length wild type protein (see below).

EXAMPLE 4

Isolation and Characterization of Other Mammalian Nucleotide Sequences that are Homologous to a Member of an Analogous Bacterial Mismatch Repair Pathway A. Identification The information provided by isolation of yeast and human sequences described above allows the development of a general protocol for isolating any other eukaryotic nucleotide sequences that are homologous to any bacterial mismatch repair gene. In particular, *E. coli* mutS homologues from mammals such as mice, cows, pigs, and monkeys can easily be identified. In each case, it could be valuable to optimize PCR reaction conditions in reactions using as a DNA template a nucleotide library known to contain at least one eukaryotic nucleotide sequence that is homologous to the bacterial mutS and hexA genes. For example, yeast library, containing SEQ ID NO.:1 or SEQ ID NO.:2, may be used. Similarly, a library containing human SEQ ID NO.:8 or SEQ ID NO.:9 could be used. The described procedure could also be modified to allow isolation and identification of eukaryotic nucleotide sequences that are homologous to other members of the bacterial mismatch repair gene family, (e.g. mutH, mutL, hexB, and mutU(uvrD)).

By way of example, we provide the sequences of degenerate oligonucleotide pools (SEQ ID NOs.:17 and 18) that may be used to isolate nucleotide sequences that are homologous to the *E. coli* mutS gene from other eukaryotes. The presented sequences include a BamHI restriction site. As will be apparent to workers skilled in the art, other restriction sites could equivalently be used. Making primers with alternative restriction sites is well within the ordinary skills of the art.

We have used the primers of SEQ ID NOs.:17 and 18 to identify a mouse nucleotide sequence, presented as SEQ ID NO.:10, that is homologous to the *E. coli* mutS genes, the yeast genes of SEQ ID NO.:1 and SEQ ID NO.:2, and the human gene of SEQ ID NO.: 8. 25-µl PCR reactions contained 10 mM Tris buffer pH 8.5, 50 mM KCe, 3 mM Mgcl$_2$, 0.01% gelatin, 50 µM each dNTP, 1.5 unit Taq DNA polymerase, 5 pmole each primer and 0.4 µg mouse DNA from Corriel Cell, Camden, N.J. 30 cycles of 30 seconds at 94° C., 30 seconds at 55° C., and 1 minute at 72° C. were performed. We have found these reaction conditions, with some variation in number of cycles, to be generally useful with several different primer sets for amplifying nucleotide sequences that are homologous to the bacterial mutS/hexA genes from higher eukaryotes. The product band was cloned and sequenced by standard methods. All ten clones analyzed contained the same sequence (SEQ ID NO.:10). Thus, the combined information from our isolation of yeast and human nucleotide sequences that are homologous to the *E. coli* mutS gene allowed us to develop a protocol that gave 100% success in isolating a nucleotide sequence from a different sequence that is homologous to the *E. coli* mutS gene. The mouse sequence maps to a region of mouse chromosome 17 that is syntenic with human chromosome 2p21-22. This confirms that the human gene corresponding to SEQ ID NO.:8 is located on human chromosome 2 and is likely to be the gene responsible for conferring susceptibility to HNPCC.

Preferred clones of a eukaryotic nucleotide sequences that are homologous to the *E. coli* mutS mismatch repair gene include clones of any eukaryotic nucleotide sequence capable of encoding FATH(F/Y). Particularly preferred clones also include sequences that are capable of encoding TGPNM, a helix-turn-helix DNA binding motif and/or a Mg$^{2+}$-ATP binding site. Ideal clones contain a complete open reading frame, i.e. one that starts with a methionine and ends with a stop codon. It is also desirable to have cDNA and genomic clones that include all 5' and 3' untranslated sequences that are relevant to the expression of the endogenous gene. If it is necessary to assemble a long clone from short fragments, the short fragments can be aligned based upon overlapping sequences. Thereafter, the long clone can be prepared by, for example, ligating the fragments together using appropriate restriction enzymes or by using PCR to amplify intact clones.

In some instances, identification of preferred eukaryotic nucleotide sequences of the invention might first require identification of particular eukaryotic tissues or cell lines in which the nucleotide sequences of interest are expressed. Any of several standard techniques can be used to assay expression of nucleotide sequences. For example, PCR can be performed using isolated RNA samples as template nucleic acid. Western blotting can be used to assay expression of a protein encoded by the nucleotide sequences. Alternatively, Northern analysis of isolated total RNA or oligo(dT)-selected messenger RNA (mRNA) isolated from cells can be used to identify eukaryotic transcripts that are homologous to a bacterial mismatch repair gene. Any probe capable of hybridizing with a eukaryotic transcript that is homologous to a bacterial mismatch repair gene can be used. For example, the PCR-generated probes to the yeast and human clones described above could be used in this Northern analysis.

Northern analysis also indicates the size of a eukaryotic transcript that is homologous to a bacterial mismatch repair gene. This information allows one to determine whether a given identified cDNA clone is long enough to encompass the entire transcript or whether it is necessary to obtain further cDNA clones (i.e., if the length of the cDNA clone is less than the length of RNA transcripts as seen by Northern analysis), without having to first sequence identified clones and determine whether or not they contain a complete open reading frame.

If an identified cDNA clone is not long enough, any of several possible steps can be performed, such as: (i) rescreen the same library with the longest probes available or with probes derived form the 5' end of a related clone to identify a longer cDNA; (ii) screen a different cDNA library with the longest available probes; and (iii) prepare a primer-extended cDNA library by reverse transcription using a specific nucleotide primer corresponding to a region close to, but not at, the most 5' available region. This primer extended library can then be screened with a probe corresponding to available sequences located 5' to the primer. (See for example, Rupp et al., Neuron, 6: 811-823, 1991).

Eukaryotic nucleotide sequences of the invention also include isolated genomic clones which can be identified, for example, by using any available probe to screen genomic libraries by hybridization or by PCR amplification.

As discussed above, PCR-generated probes can be used to isolate yeast and human nucleotide sequences that are homologous to a bacterial mismatch repair gene. Such probes can also be used in the general protocol to isolate eukaryotic nucleotide sequences that are homologous to a bacterial mismatch repair gene. Other kinds of probes can also be used in the general protocol, including oligonucleotides that encode part of the yeast sequences shown in SEQ ID NOs.:1 or 2, part of the human sequence shown in SEQ ID NOs.:8, or part of the mouse sequence shown in SEQ ID NO.:10.

Eukaryotic nucleotide sequences of the invention can also be isolated by screening a polypeptide expression library using conventional immunization techniques, such as those described in Harlow and Lane, D, Antibodies, Cold Spring Harbor Press, New York (1988). For example, antibodies can be prepared against an isolated yeast or human polypeptide of the invention and can then be used to screen expression libraries, preferably after first being tested for cross-reactivity with polypeptides from other species that are encoded by eukaryotic nucleotide sequences that are homologous to a bacterial mismatch repair gene.

EXAMPLE 5

A Mouse Nucleotide Sequence that is Homologous to the E. coli mutS Mismatch Repair Gene Maps to Mouse Chromosome 17 in a Region that is Syntenic with Human Chromosome 2p21-22

Procedure

The map location of the human MSH-2 gene (corresponding to SEQ ID NO.: 8) was determined in greater detail by mapping the location of the mouse homologue (MSH-2$_{mouse}$: corresponding to SEQ ID NO.: 10). This was possible because the highly conserved region of human MSH-2 corresponding to SEQ ID NO.: 8 contains large stretches of 100% amino acid identity with the mouse homologue and the coding DNA sequence in this region contains segments as long as 100 bp that are 92% identical with the human DNA sequence (comparison of SEQ ID NO.: 8 and SEQ ID NO.: 10). A probe (SEQ ID NO.: 15) to a human conserved region, and a probe (SEQ ID NO.: 10) to a mouse conserved region were found to hybridize to a single locus in Southern blots of restriction digests of DNA obtained from the products of interspecific mouse crosses. This made it possible to map the human MSH-2 gene relative to restriction site polymorphism markers.

The mouse chromosomal location of human MSH-2 was determined by interspecific backcross analysis using progeny derived from matings of [(C57BL/6J×*Mus spretus*)F1× C57BL/6J] mice. This interspecific backcross mapping panel has been typed for over 1300 loci that are well distributed among all the autosomes as well as the X chromosome (Copeland and Jenkins, Trends Genet. 7: 13-18, 1991). C57BL/6J and *M. spretus* DNAs were digested with several enzymes and analyzed by Southern blot hybridization for informative restriction fragment length polymorphisms (RFLPs) using SEQ ID NO.: 15 as a probe. Southern analysis had previously confirmed SEQ ID NO.: 15 hcross-hybridized with both the MSH-2$_{mouse}$ and hamster (MSH-2$_{hamster}$) homologues. A 9.4 kb *M. spretus* HindIII RFLP was used to follow the segregation of the MSH-2$_{mouse}$ locus in backcross mice.

The mapping results indicated that MSH-2$_{mouse}$ is located in the distal region of mouse chromosome 17 linked to Lama, Tik, Msosl and Lcgr/Gpcr. Although 147 mice were analyzed for every marker, up to 176 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere— Lama-9/176-Tik-1/162-Msosl-3/161-MSH-2$_{mouse\_/\_}$Lcgr/ Gpcr. The recombination frequencies [expressed as genetic distances in centiMorgans (cM)+the standard error] are— Lama-5.1+/−1.7-Tik-0.6+/−0.6    Msosl-1.9+/−1.1–MSH-2$_{mouse\_+/-\_\_}$Lcgr/Gpcr.

Comparison of the interspecific map of chromosome 17 with a composite mouse linkage map that reports the map location of many uncloned mouse mutations (compiled by M. T. Davisson, T. H. Roderick, A. L. Hillyard, and D. P. Doolittle and provided from GBASE, a computerized database maintained at The Jackson Laboratory, Bar Harbor, Me.) suggested that MSH-2$_{mouse}$ mapped in a region of the composite map that lacks mouse mutations.

The distal region of mouse chromosome 17 shares a region of homology with human chromosome 2p. In particular, Msosl has been place on human 2p21-22. The tight linkage between Msosl and MSH-2$_{mouse}$ in mouse suggest that human MSH-2 will reside on or very near to human chromosome 2p21-22, as well. This map location is somewhat different from the reported location of HNPCC of 2p15-16. However, we believe that within the error of mapping of the HNPCC gene and the other genetic markers in this region, the human MSH-2 gene and the HNPCC gene appear to map in the same location.

Materials and Methods

Interspecific Backcross Mouse Mapping: Interspecific backcross progeny were generated by mating (C57BL/6J×*M. spretus*)F1 females and C57BL/6J males as described (Copeland and Jenkins, supra 1991). A total of 205 N2 mice were used to map the Hms2 locus. DNA isolation, restriction enzyme digestion, agarose gel electrophoresis, Southern blot transfer and hybridization were preformed essentially as described (Jenkins et al., J. Virol 43: 26-36, 1982). All blots were prepared with Zetabind nylon membrane (AMF-Cuno). The probe, an 360 bp human cDNA clone, was labelled with [$\alpha$-$^{32}$P]-dCTP using a random primed labeling kit (Stratagene); washing was done to a final stringency of 1.0×SSCP, 0.1% SDS, 65° C.

A fragment of 12.5 kb was detected in Hind~I digested C57BL/6J DNA and a fragment of 9.4 kb was detected in HindIII digested *M. spretus* DNA. The presence or absence of the 9.4 kb *M. spretus*-specific HindIII fragment was followed in backcross mice. A description of the probes and RFLPs for the loci linked to MSH-2 including laminin A subunit (Lama) and the mouse homologue-1 of Sos (Msosl) has been reported previously (Webb et al., submitted). One locus not previously reported is antiphosphotyrosine immunoreactive kinase (Tik) (Icely et al., J. Biol. Chem. 266: 16073-77, 1991). The probe was an 1733 bp BamHI fragment of mouse cDNA that detected 14.0, 6.1, 3.7, and 1.5 kb fragments in ScaI digested C57BL/6J DNA and 7.3, 5.6, 2.9, 2.1, and 1.5 kb fragments in ScaI digested *M. spretus* DNA. The *M. spretus*-specific RFLPs cosegregated and were followed in this analysis. Recombination distances were calculated as described (Green, Genetics and Probability in Animal Breeding Experiments, Oxford University Press, New York, pp. 77-113) using the computer program SPRETUS MADNESS. Gene determined by minimizing the number of recombination events required to explain the allele distribution patterns.

EXAMPLE 6

Preparation of Constructions for Transfections and Microinjections

Methods for purification of DNA for microinjection are well known to those of ordinary skill in the art. See, for example, Hogan et al., *Manipulating the Mouse Embryo*, Cold spring Harbor Laboratory, Cold Spring Harbor, N.Y. (1986); and Palmer et al., *Nature*, 300: 611 (1982).

Construction of Transgenic Animals: A variety of methods are available for the production genic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., Proc. Nat. Acad. Sci. USA, 82: 4438-4442 (1985)). Embryos can be infected with viruses, especially retroviruses, modified to bear genes of the invention.

Pluripotent stem cells derived from the inner cell mass of the embryo and stabilized in culture can be manipulated in culture to incorporate urea transporter genes of the invention. A transgenic animal can be produced from such cells through implantation into a blastocyst that is implanted into a foster mother and allowed to come to term.

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. B6D2F$_1$ males can be used for mating and vasectomized Swiss Webster studs can be used to stimulate pseudopregnancy. Vasectomized mice and rats can be obtained from the supplier.

Microinjection Procedures: The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, Experientia, 47: 897-905 (1991). Other procedures for introduction of DNA into tissues of animals are described in U.S. Pat. No. 4,945,050 (Sanford et al., Jul. 30, 1990).

Transgenic Mice: Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline (DPSS) with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10-12 embryos). The pipet tip is inserted into the infundibulum and the embryos transferred. After the transfer, the incision is closed by two sutures.

Transgenic Rats: The procedure for generating transgenic rats is similar to that of mice See Hammer et al., Cell, 63:1099-1112 (1990). Thirty day-old female rats are given a subcutaneous injection of 20 IU of PMSG (0.1 cc) and 48 hours later each female placed with a proven male. At the same time, 40-80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPSS with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10-12 embryos are transferred into each rat oviduct through the infundibulum. The incision is then closed with sutures, and the foster mothers are housed singly.

Embryonic Stem (ES) Cell Methods

Introduction of DNA into ES Cells

Methods for the culturing of ES cells and the subsequent production of transgenic animals by the introduction of DNA into ES cells using methods such as electroporation, calcium phosphate/DNA precipitation; and direct injection are well known to those of ordinary skill in the art. See, for example, Teratocarcinomas and Embryonic Stem Cells, A Practical Approach, E. J. Robertson, ed., IRL Press (1987). Selection of the desired clone of eukaryotic mismatch repair gene-containing ES cells is accomplished through one of several means. Although embryonic stem cells are currently available for mice only, it is expected that similar methods and procedures as described and cited here will be effective for embryonic stem cells from different species as they become available.

In cases involving random gene integration, a clone containing the gene sequence(s) of the invention is co-transfected with a gene encoding neomycin resistance. Alternatively, the gene encoding neomycin resistance is physically linked to the mismatch repair gene. Transfection is carried out by any one of several methods well known to those of ordinary skill in the art (E. J. Robertson, supra). Calcium phosphate/DNA precipitation, direct injection, and electroporation are the preferred methods. Following DNA introduction, cells are fed with selection medium containing 10% fetal bovine serum in DMEM supplemented with G418 (between 200 and 500 μg/ml biological weight). Colonies of cells resistant to G418 are isolated using cloning rings and expanded. DNA is extracted from drug resistant clones and Southern blotting experiments using a transgene-specific DNA probe are used to identify those clones carrying the mismatch repair gene sequence(s). In some experiments, PCR methods are used to identify the clones of interest.

DNA molecules introduced into ES cells can also be integrated into the chromosome through the process of homologous recombination. Copecchi, Science, 244: 1288-1292 (1989). Direct injection results in a high efficiency of integration. Desired clones are identified through PCR of DNA prepared from pools of injected ES cells. Positive cells within the pools are identified by PCR subsequent to cell cloning. DNA introduction by electroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by. Copecchi, supra and Joyner et al., Nature, 338: 153-156 (1989), the disclosures of which are incorporated herein.

Embryo Recovery and ES Cell Injection

Naturally cycling or superovulated female mice mated with males are used to harvest embryos for the implantation of ES cells. It is desirable to use the C57BL165 strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10-20 ES cells are injected into blastocysts using a glass microneedle with an internal diameter of approximately 20 μm.

Transfer of Embryos to Receptive Females

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

Identification of Transgenic Mice and Rats

Tail samples (1-2 cm) are removed from three week old animals. DNA is prepared and analyzed by Southern blot or PCR to detect transgenic founder ($F_0$) animals and their progeny ($F_1$ and $F_2$). In this way, animals that have become transgenic for the homologue of a bacterial mismatch repair gene are identified. Because not every transgenic animal expresses the mismatch repair polypeptide, and not all of those that do will have the expression pattern anticipated by the experimenter, it is necessary to characterize each line of transgenic animals with regard to expression of the polypeptide in different tissues.

Production of Non-Rodent Transgenic Animals: Procedures for the production of non-rodent mammals and other animals have been discussed by others. See Houdebine and Chourrout, supra; Pursel et al., Science 244: 1281-1288 (1989); and Simms et al., Bio/Technology, 6: 179-183 (1988).

Identification of Other Transgenic Organisms: An organism is identified as a potential transgenic by taking a sample of the organism for DNA extraction and hybridization analysis with a probe complementary to the gene of interest. Alternatively, DNA extracted from the organism can be subjected to PCR analysis using PCR primers complementary to the gene of interest.

EXAMPLE 7

Protocol for Inactivating a Mammalian Homologue of a Mismatch Repair Gene

Mouse genomic clones are isolated by screening a genomic library from the D3 strain of mouse with a human mismatch repair gene. Duplicate lifts are hybridized with a radiolabeled probe by established protocols (Sambrook, J. et al., The Cloning Manual, Cold Spring Harbor Press, N.Y.). Plaques that correspond to positive signal on both lifts are isolated and purified by successive screening rounds at decreasing plaque density. The validity of the isolated clones is confirmed by nucleotide sequencing. One of the many possible protocols for inactivating a eukaryotic homologue of a bacterial mismatch repair gene is presented below.

The genomic clones are used to prepare a gene targeting vector for the deletion of a mismatch repair gene in embryonic stem cells by homologous recombination. A neomycin resistance gene (neo) with its transcriptional and translational signals, is cloned into convenient sites that are near the 5' end of the gene. This will disrupt the coding sequence of the mismatch repair gene sequence and allow for selection by the drug Geneticin (G418) by embryonic stem (ES) cells transfected with the vector. The Herpes simplex virus thymidine kinase (HSV-tk) gene is placed at the other end of the genomic DNA as a second selectable marker. Only stem cells with the neo gene will grow in the presence of this drug.

Random integration of this construct into the ES genome will occur via sequences at the ends of the construct. In these cell lines, the HSV-tk gene will be functional and the drug gancyclovir will therefore be cytotoxic to cells having an integrated sequence of the altered mismatch repair coding sequence.

Homologous recombination will also take place between homologous DNA sequences of the ES mismatch repair gene and the targeting vector. This usually results in the excision of the HSV-tk gene because it is not homologous with the mismatch repair gene sequence.

Thus, by growing the transfected ES cells in G418 and gancyclovir, the cell lines in which homologous recombination has occurred will be highly enriched. These cells will contain a disrupted coding sequence of mismatch repair gene. Individual clones are isolated and grown up to produce enough cells for frozen stocks and for preparation of DNA. Clones in which the mismatch repair gene has been successfully targeted are identified by Southern blot analysis. The final phase of the procedure is to inject targeted ES cells into blastocysts and to transfer the blastocysts into pseudopregnant females. The resulting chimeric animals are bred and the offspring are analyzed by Southern blotting to identify individuals that carry the mutated form of the gene in the germ line. These animals will be mated to determine the effect of mismatch repair gene deficiency on murine development and physiology.

EXAMPLE 8

Amplification of hMSH2 Genomic Clones from a P1 Phage Library 25 ng genomic DNA was used in PCR reactions including:
0.05 mM dNTPs
50 mM KCl
3 mM Mg
10 mM Tris-HCl pH 8.5
0.01% gelatin
primers 16061 (SEQ ID NO.: 114) and 16062 (SEQ ID NO.: 115)

Reactions were performed on a Perkin-Elmer Cetus model 9600 thermal cycler. Reactions were incubated at 95° C. for 5 minutes, followed by 35 cycles of:
94° C. for 30 seconds
55° C. for 30 seconds
72° C. for 1 minute.

A final 7 minute extension reaction was then performed at 72° C. Desirable P1 clones were those from which an approximately 146 bp product band was produced.

EXAMPLE 9

Amplification of hMSH2 Sequences from Genomic DNA Using Nested PCR Primers

We performed two-step PCR amplification of hMSH2 sequences from genomic DNA as follows. Typically, the first amplification was performed in a 25 microliter reaction including:
25 ng of chromosomal DNA
Perkin Elmer PCR buffer II (any suitable buffer could be used)
3 mM $MgCl_2$
50 µM each dNTP
Taq DNA polymerase
5 µM primers and incubated at 95° C. for 5 minutes, followed by 20 cycles of:
94° C. for 30 seconds
55° C. for 30 seconds The product band was typically small enough (less than approximately 500 bp) that separate extension steps were not performed after each cycle. Rather, a single extension step was performed, at 72° C. for 7 minutes, after the 20 cycles were completed.

Reaction products were stored at 4° C.

The second amplification reaction, usually 25 or 50 microliters in volume, included:
1 or 2 microliters (depending on the volume of the reaction) of the first amplification reaction product
Perkin Elmer PCR buffer II (any suitable buffer could be used)
3 mM $MgCl_2$
50 µM each dNTP
Taq DNA polymerase
5 µM nested primers, and was incubated at 95° C. for 5 minutes, followed by 20-25 cycles of:
94° C. for 30 seconds
55° C. for 30 seconds A single extension step was performed, at 72° C. for 7 minutes, after the cycles were completed Reaction products were stored at 4° C.

Any set of primers capable of amplifying a target hMSH2 sequence can be used in the first amplification reaction. We have used each of the primer sets presented in Table 2 to amplify an individual hMSH2 exon in the first amplification reaction. We have also used combinations of those primer sets, thereby amplifying multiple individual hMSH2 exons in the first amplification reaction. In particular, we have used SEQ ID NOs.: 25, 26, 29, 30, 32, 63 and 64 together in a single reaction to simultaneously amplify hMSH2 exons 9, 10, 11, and 12.

The nested primers used in the first amplification step were designed relative to the primers used in the first amplification reaction. That is, where a single set of primers is used in the first amplification reaction, the primers used in the second amplification reaction should be identical to the primers used in the first reaction except that the primers used in the second reaction should not include the 5'-most nucleotides of the first amplification reaction primers, and should extend sufficiently more at the 3' end that the $T_m$ of the second amplification reaction primers is approximately the same as the $T_m$ of the first amplification reaction primers. Our second reaction primers typically lacked the 35'-most nucleotides of the first amplification reaction primers, and extended approximately 3-6 nucleotides farther on the 3' end. SEQ ID NOs.: 146/148-153/154 are examples of nested primer pairs that could be used in a second amplification reaction when SEQ ID NOs.: 62/63-64/32, respectively, were used in the first amplification reaction.

We have also found that it can be valuable to include a standard sequence (e.g. 5'-TGTAAAACGACGGCCAGT) that can be used, for example, to prime sequencing reactions at the 5' end of one or both of the second amplification reaction primers. Additionally, we have found it useful to biotinylate that last nucleotide of one or both of the second amplification reaction primers so that the product band can easily be purified using magnetic beads (see, for example Tong et al., Anal. Chem. 64:2672-2677, 1992) and then sequencing reactions can be performed directly on the bead-associated products (see, for example, Debuire et al., Clin. Chem. 39:1682-5, 1993; Wahlberg et al., Electrophonesis 13:547-551, 1992; Kaneoka et al., Biotechniques 10: 30, 32, 34, 1991; Huhman et al., Biotechniques 10:84-93, 1991; Hultman et al., Nuc. Acid. Res. 17:4937-46, 1989).

Genomic Sequencing

The cDNA sequence of hMSH2 is presented here as SEQ ID NO.:45, and can also be found in GenBank under Accession Number U03911 or Accession Number U04045. We note that there may be some variability in these different listings of the hMSH2 cDNA sequence, resulting from polymorphisms within the human population; degeneracy of the genetic code; and/or minor editing errors during compilation and interpretation of sequencing results.

To cover regions that might be absent from the lambda libraries, we designed oligonucleotide primers capable of amplifying a region of the hMSH2 cDNA, nucleotides 655 to 799, for which corresponding genomic sequences had not been identified in the lambda screen. The primers were then sent to Genome Sciences, Inc. (St. Louis, Mo.) and were used to amplify product bands from a human genomic P1 library. Positive clones identified by Genome Sciences, Inc. were further analyzed (i.e. sequenced etc.) by us. Two of these positive P1 clones, numbers 1315 and 1316 are shown in FIG. 5.

We sequenced our identified genomic clones using methods known in the art including cycle sequencing with SequiTherm™ cycle sequencing kit (available from Epicentre Technologies, Madison, Wis.). Sequencing primers were designed based on the known hMSH2 cDNA sequence. New primers were designed as new sequence was deduced. In particular, when potential exon/intron boundaries were identified in the genomic clones, new primers were designed that prime from coding (i.e. exonic) sequence, toward intronic sequence. As is known in the art, this process can be re-iterated as necessary to sequence as much intronic sequence as is desirable, and also can be used to sequence non-exonic upstream and downstream regions of a gene.

Generally, when accuracy is required in DNA sequencing studies, it is desirable to sequence both strands of the molecule and/or to sequence the molecule more than once, preferably using different nucleotide primers. New sequencing primers can be designed based on a known sequence, even if that sequence has not been confirmed. As is known in the art, it is not necessary that a sequencing primer hybridize perfectly with its target sequence, but only that it hybridize sufficiently specifically under the conditions of the sequencing reactions, including being able to base-pair with the template at its 3' end, that the resultant sequence is interpretable.

Through these genomic sequencing studies, we have identified all sixteen exons within the hMSH2 gene, and have mapped the intron/exon boundaries. Table 1 presents the nucleotide coordinates of the hMSH2 exons. The presented coordinates are based on the hMSH2 cDNA sequence, assigning position "1" to the "A" of the start "ATG" (which A is nucleotide number 1 in SEQ ID NO.:45).

TABLE 1

| exon 1 | 1 (ATG)-211 |
|---|---|
| exon 2 | 212-366 |
| exon 3 | 367-645 |
| exon 4 | 646-792 |
| exon 5 | 793-942 |
| exon 6 | 943-1076 |
| exon 7 | 1077-1276 |
| exon 8 | 1277-1386 |
| exon 9 | 1387-1510 |
| exon 10 | 1511-1661 |
| exon 11 | 1662-1759 |
| exon 12 | 1760-2005 |
| exon 13 | 2006-2210 |
| exon 14 | 2211-2458 |
| exon 15 | 2459-2634 |
| exon 16 | 2635-2803 (STOP) |

Our genomic sequencing studies have also allowed us to determine the nucleotide sequence of non-exonic regions of the hMSH2 gene. SEQ ID NOs.: 82-113 present upstream, downstream, and intronic hMSH2 sequences. Each of the nucleotide sequences presented in SEQ ID NOs.: 82-113 has been confirmed by sequencing of the complimentary DNA strand and/or by sequencing with more than one primer, although there may be some sequence ambiguities within the sites to which our primers hybridized, and also within the poly-A tract in SEQ ID NO.: 91. Each of the nucleotide sequences presented in SEQ ID NOs.:157 and 114-144 contains additional non-exonic sequence as compared with the sequences presented in SEQ ID NOs.: 82-113, respectively. The additional non-exonic sequences presented in SEQ ID NOs.: 157 and 114-144 have not been confirmed by sequencing of the complementary strand and therefore may contain some errors; however, these sequences provide useful information for further sequencing studies and for primer design, among other things.

In another aspect of the invention, the information provided by these genomic sequencing studies has allowed the design of nucleotide primers capable of amplifying individual hMSH2 exons. The nucleotide sequences of oligonucleotide primers that we have used to amplify individual hMSH2 exons from genomic DNA are presented in Table 2. We have used these primer sets in our studies of hMSH2 mutations that correlate with cancer susceptibility and/or that correlate with tumor development in particular individuals (see below).

TABLE 2

| EXON NO. | PRIMER LOCATION | PRIMER NO. | PRIMER SEQU. ID NO. | PRIMER NUCLEOTIDE SEQUENCE |
|---|---|---|---|---|
| 1 | upstream | 18538 | 46 | 5'-tcgcgcattttcttcaacc |
| 1 | downstream | 17209 | 47 | 5'-gtccctccccagcacgc |
| 2 | upstream | 18183 | 48 | 5'-gaagtccagctaatacagtgc |
| 2 | downstream | 18230 | 49 | 5'-cttcacatttttattttctactc |
| 3 | upstream | 18226 | 50 | 5'-gcttataaaattttaaagtatgttc |
| 3 | downstream | 18180 | 51 | 5'-gcctttcctaggcctggaatctcc |
| 4 | upstream | 18298 | 52 | 5'-ttcattttttgcttttcttattcc |
| 4 | downstream | 18545 | 53 | 5'-atatgacagaaatatccttc |
| 5 | upstream | 18220 | 54 | 5'-ccagtggtatagaaatcttcg |
| 5 | downstream | 18572 | 55 | 5'-ccaatcaacattttaaccc |
| 6 | upstream | 18221 | 56 | 5'-gttttcactaatgagcttgcc |
| 6 | downstream | 18900 | 57 | 5'-gtggtataatcatgtggg |
| 7 | upstream | 18573 | 58 | 5'-gacttacgtgcttagttg |
| 7 | downstream | 18222 | 59 | 5'-gtatatattgtatgagttgaagg |
| 8 | upstream | 18223 | 60 | 5'-gatttgtattctgtaaaatgagatc |
| 8 | downstream | 18294 | 61 | 5'-ggcctttgcttttaaaaataac |
| 9 | upstream | 17231 | 62 | 5'-gtctttacccattatttatagg |
| 9 | downstream | 17232 | 63 | 5'-gtatagacaaaagaattattcc |
| 10 | upstream | 16338 | 26 | 5'-ggtagtaggtatttatggaatac |
| 10 | downstream | 16337 | 25 | 5'-catgttagagcatttaggg |
| 11 | upstream | 16411 | 30 | 5'-cacattgcttctagtacac |
| 11 | downstream | 16323 | 29 | 5'-ccaggtgacattcagaac |
| 12 | upstream | 16325 | 64 | 5'-attcagtattcctgtgtac |
| 12 | downstream | 16390 | 32 | 5'-cgttacccccacaaagc |
| 13 | upstream | 16324 | 33 | 5'-cgcgattaatcatcagtg |
| 13 | downstream | 16340 | 34 | 5'-ggacagagacatacatttctatc |
| 14 | upstream | 16326 | 35 | 5'-taccacattttatgtgatgg |
| 14 | downstream | 16369 | 36 | 5'-ggggtagtaagtttccc |
| 15 | upstream | 16322 | 37 | 5'-ctcttctcatgctgtccc |
| 15 | downstream | 16339 | 38 | 5'-atagagaagctaagttaaac |
| 16 | upstream | 16412 | 40 | 5'-taattactcatgggacattc |
| 16 | downstream | 16858 | 65 | 5'-taccttcattccattactgg |

The primer pairs presented in Table 2 each hybridize to non-exonic sequences flanking an individual exon. As is known in the art, any of a variety of different primer pairs could be used to amplify an individual hMSH2 exon. For example, if it is not essential that every exonic nucleotide be amplified primers that hybridize to exon sequences can be used. Primers that hybridize across intron/exon boundaries can also be used, as can any variety of intron-binding primers.

The hMSH2 sequence information provided herein may be used to design any variety of oligonucleotide primers for use in identifying hMSH2 mutations that correlate with cancer susceptibility and/or with tumor development in an individual, including primers that will amplify more than one exon (and/or flanking non-exonic sequences) in a single product band. Recent results have shown that PCR can be used to amplify very large fragments, and perhaps could even be used to amplify an entire gene (see Barnes *Proc. Natl. Acad. Sci USA* 91:2216-2220, 1994; Cohen *Science* 263:1564-1565, 1994).

One of ordinary skill in the art would be familiar with considerations important to the design of PCR primers, (see for example, PCR Protocols: a Guide to Methods and Applications. Ed: Innis et al., Academic Press, 1990, incorporated herein by reference) for use to amplify the desired fragment or gene. These considerations may be similar, though not necessarily identical to those involved in design of sequencing primers, as discussed above. Generally, it is important that primers hybridize relatively specifically (i.e. have a $T_m$ of greater than about 55° C., and preferably around 60° C.). For most cases, primers of between about 17 and 25 nucleotides in length work well. Longer primers can be useful for amplifying longer fragments. In all cases, it is desirable to avoid using primers that are complementary to more than one sequence in the human genome, so that each pair of PCR primers amplifies only a single, correct fragment. Nonetheless, it is only absolutely necessary that the correct product band be distinguishable from other product bands in the PCR reaction.

The exact PCR conditions (e.g. salt concentration, number of rounds of amplification, type of DNA polymerase used, etc.) can be varied as known in the art to improve, for example, yield or specificity of the reaction. In particular, we have found it valuable to use nested primers in PCR reactions in order to improve amplification specificity (see Example 2). This approach allows us to use less substrate DNA and also improves amplification specificity.

Of course, the same approach described herein can be used to identify genomic sequences of mismatch repair genes from other, non-human eukaryotic organisms. As discussed above, we have identified sequences of a mouse gene, herein termed mMSH2, that is homologous to the yeast and human MSH2 genes.

EXAMPLE 10

Diagnosing Cancer Susceptibility

Mutations that confer cancer susceptibility (i.e. that confer a likelihood of developing a cancer that is higher than the likelihood that a subject not carrying a mutation will develop that cancer) to a subject are expected to be present throughout the tissues of that subject (i.e. not to be restricted to tumor tissue) and/or to be present in the germ line of at least one of the subject's parents. Tumor tissues may also contain additional mismatch repair gene mutations that are not present in the subject's other tissues, and that were not inherited, but were involved in (and/or necessary for) development of that tumor (see below and, for example, Parsons et al. Cell 75:1227-1236, 1993). The identification of such tumor-specific mutations is also valuable, and will be addressed further below.

We have previously demonstrated that the hMSH2 gene maps to human chromosome 2 and that mutations in hMSH2 are likely to confer susceptibility to HNPCC (see, Fishel et al. supra). We have confirmed this idea, and report studies linking mutation of the hMSH2 gene with incidence of cancer in HNPCC lineages. Yet another aspect of the invention, therefore, involves identification of mutations in mismatch repair genes (such as hMSH2), and particularly involves identification of mismatch repair gene mutations that correlate with cancer susceptibility.

We have analyzed one large HNPCC lineage (Pedigree 2; an extended Muir-Torre kindred showing positive linkage to chromosome 2p (Hall et al., Eur. J. Cancer 30A: 180-182, 1994) for the presence of mutations in the hMSH2 gene. The pedigree of this family is presented in FIG. 1. We note that members of this family developed many different kinds of cancer (see FIG. 1), which is consistent with the idea that the family carries a mutation in a gene involved in DNA repair (e.g. hMSH2).

DNA samples from 21 members of this family were provided by Dr. Timothy Bishop of the Imperial Cancer Research Fund, Genetic Epidemiology Laboratory at St. James University Hospital in Leeds, England. We used two different direct sequencing methods to detect hMSH2 mutations in this family. First, individual exons were amplified by PCR (using primers from Table 2) and were purified. Purified exons were sequenced using Taq DNA polymerase and dye terminator chemistry (see techniques described in Fishel et al., Cell 75:1027-1038, 1993). Second, individual exons were amplified using a multiplex protocol involving amplification with two sets of nested primers. The final PCR products were captured on magnetic beads, and were sequenced using Sequenase™ and dye terminator chemistry.

In affected individuals (e.g. individuals that had developed a characteristic cancer and/or that had been shown by, for example, linkage analysis, to be mutation carriers), the sequence became uninterpretable after the A at nucleotide position 1985 in exon 12 due to the presence of two signals at many individual nucleotide positions (see FIG. 2). Unaffected individuals that were determined by linkage analysis not to be mutation carriers did not show regions of uninterpretable sequence. These results are consistent with the idea that affected individuals are heterozygous for a frameshift mutation caused by deletion of nucleotides 1985 and 1986.

Analysis of the sequence data from affected individuals, using standard basecalling software (e.g. Sequence Analysis 1.2, from Applied Biosystems, Inc., in conjunction with Sequencher 2.0, available from Gene Codes, Inc.) on an Applied Biosystems 373 (ABI 373) automatic sequencer, confirmed the presence of a frameshift mutation—the deletion of an AT basepair at nucleotide position 1985 and of a GC basepair at nucleotide position 1986. This 2-basepair (bp) deletion causes a frameshift in the reading frame of the encoded protein, and results in termination of the polypeptide chain 11 amino acids later. This mutant hMSH2 allele is therefore predicted to produce a protein that lacks the most conserved region of Msh2 (corresponding to amino acids 662 to 934 (end) of hMsh2, as presented in SEQ ID NO.:16, see FIG. 3).

Interestingly, we found that different sequencing methods differed in allowing analysis of heterozygous sequences. Specifically, we found that the Sequenase™/dye primer chemistry resulted in more uniform nucleotide incorporation, compared to that found with the Taq DNA polymerase/dye terminator chemistry, and therefore allowed easier detection of heterozygosities.

The 2 bp deletion identified in affected members of Family 1 produces a new AflIII site in exon 12 (nucleotide position 1983). We amplified exon 12 from all 21 family members for whom DNA was available and analyzed the product bands by digestion with AflIII. The mutant AflIII digestion pattern (product bands of approximately 154, 114, and 57 bp) was observed in exon 12 DNA isolated and amplified from all affected individuals. These individuals also showed the normal AflIII restriction pattern (product bands of approximately 213 and 114 bp), indicating that they are heterozygous for the mutation. By contrast, all unaffected individuals who were predicted by linkage analysis not to be carriers showed only the normal AflIII restriction pattern.

Thus, we have identified a mutation in the hMSH2 gene that correlates with cancer susceptibility. Other hMSH2 mutations that correlate with cancer susceptibility can likewise easily be identified using mismatch repair gene sequence information.

In fact, other researchers have already reported the successful identification of such hMSH2 mutations, based on our previously provided sequence information. For example, Leach et al. (Cell 75:1215-1225, 1993, incorporated herein by reference) have identified the following hMSH2 mutations in HNPCC lineages:

(i) a C to T transition at codon 622 (nucleotide 1865) that results in a substitution of a leucine for a proline;

(ii) a presumptive splicing defect that removes codons 265-314 (exon 5) from the messenger RNA (mRNA); and (iii) a C to T transition at codon 406 (nucleotide 1216) that results in a substitution of a stop codon for an arginine residue.

Based on the information we have provided one of ordinary skill in the art could readily identify additional hMSH2 mutations that correlate with cancer susceptibility.

Not all of the identified cancer-susceptibility-associated hMSH2 mutations are found in coding sequence (see above). Mutations that affect any level (e.g. transcription, splicing, translation, post-translational modification, association with other factors, etc.) of hMSH2 expression or activity could potentially contribute to cancer susceptibility. In particular, some of the identified hMSH2 mutations discussed above apparently cause defects in splicing of the hMSH2 pre-messenger RNA (pre-mRNA). Also, the information provided herein allows for identification of, for example, promoter sequences, ribosome binding sites, etc. for the hMSH2 gene, and therefore allows identification of changes in such sites that affect expression of an hMSH2 gene product (e.g. pre-mRNA, mRNA, and/or encoded protein).

Any method known in the art may be used to identify changes in nucleotide sequence of hMSH2 DNA or RNA. Known methods include, but are not limited to, direct sequence analysis (often assisted by PCR amplification, as discussed above), single-strand conformational polymorphism analysis, denaturing polyacrylamide gel electrophoresis, etc. (see, for example, Grompe et al. Nature Genetics 5:111-117, 1993). Mutations that cause splicing defects can be identified by intron sequencing and/or by analysis of RNA. RNA can be analyzed by, for example, reverse-transcription coupled PCR or other methods known in the art (see, for example, Leach et al supra; Grompe et al. supra; Ikonen et al. PCR Methods and Applications 1:234-40, 1992). In some instances, changes in an hMSH2 nucleotide sequence may be identified by analysis of an encoded polypeptide using known methods such as western blots and/or activity assays (see Sambrook et al. supra and references cited below).

As we have discussed herein, the hMSH2 gene is homologous to the bacterial mutS gene, which bacterial mutS gene is part of a homologue mismatch repair pathway. Presumably, human homologues of other bacterial genes involved in this pathway (e.g. mutL, mutH, mutU(uvrD), etc.) also exist, although the different factors may not be equally conserved, especially given that most eukaryotic cells may not utilize the same methylation system used by E. coli (see, for example,) Proffitt et al. Mol. Cell. Biol. 4:985-988, 1984; Hare et al., Proc. Natl. Acad. Sci. USA, 82:7350-7354, 1985; Thomas et al., J. Biol. Chem., 266:3744-3751, 1991; Holmes et al., Proc. Natl. Acad. Sci. USA, 82; 5837-5841, 1990). We have taught methods of identifying such homologues and have suggested that mutations in other homologues could confer susceptibility to cancer.

In fact, the approach described herein has successfully been applied to the E. coli mutL gene, and a homologous human gene, hMLH1, has been identified (see Bronner et al. Nature 368:258-261, 1994; Papadopoulos et al. Science 263: 1625-1629, 1994, each of which is incorporated herein by reference). The cDNA sequence of the hMLH1 gene is presented as SEQ ID NO.:124 and can be found in GenBank as Accession Number 007343. Mutations in hMLH1 that correlate with the incidence of cancer in HNPCC lineages have also been identified. In particular, Bronner et al (supra) have found the following mutations in hMLH1 that correlate with susceptibility to HNPCC:
  (i) (a) C to T transition at nucleotide 131; in exon 2, a highly conserved region of the protein (see FIG. 4).

Papadopoulos et al. (supra) have found the following mutations that correlate with HNPCC susceptibility:
  (i) a deletion of exon 16 (codons 578-632), which includes several highly conserved amino acids (see FIG. 4);
  (ii) a 4-nucleotide deletion at position 2179-2182, in exon 19, that produces a frame-shift followed by a new stop codon;
  (iii) a 4-nucleotide insertion after position 2266, in exon 19 (between codons 755 and 756), that results in a frame-shift and extension of the open-reading frame; and
  (iv) a 371-nucleotide deletion beginning after position 1038, reportedly resulting in a frame-shift followed by a new stop codon. This mutation is likely to reflect a deletion of hMLH1 exon 12, and may represent a splicing defect that results in exon skipping.

Based on the information we have provided, one of ordinary skill in the art can likewise readily identify additional mismatch repair gene mutations that correlate with cancer susceptibility.

As mentioned above, it is likely that mutations in mismatch repair genes will confer susceptibility to hereditary cancers other than HNPCC. In particular, it is likely that mutations in mismatch repair genes will confer susceptibility to hereditary cancers that show genomic instability of short, repeated DNA sequences (see, for example Aaltonen et al. Science 260:812-816, 1993; Thibodeau et al. Science 260:816-819, 1993; Strand et al. Nature 365:274-276, 1993; Honchel et al., Cancer Res. 54:1159-1163, 1994; Risinger et al., Cancer Res., 53:5100-5103, 1993; Ionov et al., Nature 260:558-561; 1993; Han et al., Cancer Res. 53:5087-5089, 1993; Merlo et al., Cancer Res. 54:2098-2101, 1994). Such hereditary cancers can be identified by analyses of repeat instability in tumor tissues according to known methods (see, for example, Aaltonen et al. supra; Thibodeau et al. supra; Strand et al. supra; Risinger et al. supra; Ionov et al. supra; Han et al. supra). Diagnosis of susceptibility to such cancers can then be performed by identifying mutations in mismatch repair genes that correlate with cancer susceptibility and screening individuals (using available methods including those set forth herein) for the presence of identified mismatch repair gene mutations.

EXAMPLE 11

Identification and Characterization of Mismatch-Repair-Defective Tumors

As discussed herein, in addition to their usefulness in diagnosing cancer susceptibility in a subject, nucleotide sequences that are homologous to a bacterial mismatch repair gene can be valuable for, among other things, use in the identification and characterization of mismatch-repair-defective tumors. Such identification and characterization is valuable because mismatch-repair-defective tumors respond better to particular therapy regimens. For example, mismatch repair-defective tumors might be sensitive to DNA damaging agents, especially when administered in combination with other therapeutic agents.

Defects in mismatch repair genes need not be present throughout an individual's tissues to contribute to tumor formation in that individual. Spontaneous mutation of a mismatch repair gene in a particular cell or tissue can contribute to tumor formation in that tissue. In fact, at least in some cases, a single mutation in a mismatch repair gene is not sufficient for tumor development (see, for example, Parsons et al. supra). In such instances, an individual with a single mutation in a mismatch repair-gene is susceptible to cancer, but will not develop a tumor until a secondary mutation occurs. Additionally, in some instances, the same mismatch repair gene mutation that is strictly tumor-associated in an individual will be responsible for conferring cancer susceptibility in a family with a hereditary pre-disposition to cancer development.

In yet another aspect of the invention, the sequence information we have provided can be used, with methods known in the art and provided herein to analyze tumors (or tumor cell lines) and to identify tumor-associated mutations in mismatch repair genes. Preferably, it is possible to demonstrate that these tumor-associated mutations are not present in non-tumor tissues from the same individual. The information we have provided herein is particularly useful for the identification of mismatch repair gene mutations within tumors (or tumor cell lines) that display genomic instability of short repeated DNA elements.

In fact, such studies have already been successfully performed for the hMSH2 and hMLH1 genes. Leach et al. (supra) have identified two hMSH2 mutations that are associated with a tumor that shows instability of short, repeated genomic sequences (e.g. with an "RER+" tumor. In fact, the tumor analyzed by Leach et al. was from an HNPCC family. Both hMSH2 alleles isolated from the tumor contained a mutation. Presumably, one of the mutations was inherited, and was responsible for conferring cancer susceptibility in that HNPCC lineage, and the other was a secondary, tumor-specific, mutation involved in tumor development.

The mutations identified by Leach et al. (supra) are:
  (i) a C to T transition in codon 639 (nucleotide 1915) that results in a substitution of a tyrosine for a histidine; and
  (ii) a substitution of a TG dinucleotide for an A residue in codon 663 (at nucleotide position number 1987) that results in a frame-shift and produces a termination codon 36 nucleotides downstream.

Papadopoulos et al. (supra) have identified the following hMLH1 mutation in a cell line derived from a colorectal tumor that shows microsatellite instability:

(i) a C to A transversion at codon 252 (nucleotide position number 755) that replaces a Ser residue with a stop codon. In this study, the tumor tissue did not contain a wild-type hMLH1 allele.

Mutations Versus Polymorphisms

For studies of cancer susceptibility and for tumor identification and characterization, it is important to distinguish "mutations" from "polymorphisms". A "mutation" produces a "non-wild-type allele" of a gene. A non-wild-type allele of a gene produces a transcript and/or a protein product that does not function normally within a cell (see definition above). "Mutations" can be any alteration in nucleotide sequence including insertions, deletions, substitutions, and rearrangements.

"Polymorphisms", on the other hand, are sequence differences that are found within the population of normally-functioning (i.e. "wild-type") genes. Some polymorphisms result from the degeneracy of the nucleic acid code. That is, given that most amino acids are encoded by more than one triplet codon, many different nucleotide sequences can encode the same polypeptide. Other polymorphisms are simply sequence differences that do not have a significant effect on the function of the gene or encoded polypeptide. For example, polypeptides can often tolerate small insertions or deletions, or "conservative" substitutions in their amino acid sequence without significantly altering function of the polypeptide.

"Conservative" substitutions are those in which a particular amino acid is substituted by another amino acid of similar chemical characteristics. For example, the amino acids are often categorized as "non-polar (hydrophobic)", including alanine, leucine, isoleucine, valine, proline, phenylalanine, tryptophan, and methionine; "polar neutral", including glycine, serine, threonine, cysteine, tyrosine, asparagine, and glutamine; "positively charged (basic)", including arginine, lysine, and histidine; and "negatively charged (acidic)", including aspartic acid and glutamic acid. A substitution of one amino acid for another amino acid in the same group is generally considered to be "conservative", particularly if the side groups of the two relevant amino acids are of a similar size.

The first step in identifying a mutation or polymorphism in a mismatch repair gene sequence involves identification, using available techniques including those described herein of a mismatch repair gene (or gene fragment) sequence that differs from a known, normal (e.g. wild type) sequence of the same mismatch repair gene (or gene fragment). For example, a hMSH2 gene (or gene fragment) sequence could be identified that differs in at least one nucleotide position from a known normal (e.g. wild type) hMSH2 sequence such as any of SEQ ID NOs.: 45 or 65-113.

Mutations can be distinguished from polymorphisms using any of a variety of methods, perhaps the most direct of which is data collection and correlation with tumor development (see above). That is, for example, a subject might be identified whose hMSH2 gene sequence differs from a sequence reported in SEQ ID NOs.:45 or 65-113, but who does not have cancer and has no family history of cancer. Particularly if other, preferably senior, members of that subject's family have hMSH2 gene sequences that differ from SEQ ID NOs.: 45 or 65-113 in the same way(s), it is likely that subject's hMSH2 gene sequence could be categorized as a "polymorphism". If other, unrelated individuals are identified with the same hMSH2 gene sequence and no family history of cancer, the categorization may be confirmed.

Mutations that are responsible for conferring genetic susceptibility to cancer can be identified because, among other things, such mutations are likely to be present in all tissues of an affected individual and in the germ line of at least one of that individual's parents, and are not likely to be found in unrelated families with no history of cancer.

When distinguishing mutations from polymorphisms, it can sometimes be valuable to evaluate a particular sequence difference in the presence of at least one known mismatch repair gene mutation. In some instances, a particular sequence change will not have a detectable effect (i.e. will appear to be a polymorphism) when assayed alone, but will, for example, increase the penetrance of a known mutation, such that individuals carrying both the apparent polymorphism difference and a known mutation have higher probability of developing cancer than do individuals carrying only the mutation. Sequence differences that have such an effect are properly considered to be mutations, albeit weak ones.

As discussed above mutations in mismatch repair genes or gene products produce non-wild-type versions of those genes or gene products. Some mutations can therefore be distinguished from polymorphisms by their functional characteristics in in vivo or in vitro mismatch repair assays. Any available mismatch repair assay can be used to analyze these characteristics (for examples, see Examples 9-12; see also Bishop et al., Mol. Cell. Biol. 6, 3401-3409, 1986; Folger et-al., Mol. Cell. Biol. 5, 70-74, 1985; T. C. Brown et al., Cell 54, 705-711, 1988; T. C. Brown et al., Genome 31, 578-583, 1989; C. Muster-Nassal et al., Proc. Natl. Acad. Sci. U.S.A. 83, 7618-7622, 1986; I. Varlet et al., Proc. Natl. Acad. Sci. U.S.A. 87, 7883-7887, 1990; D. C. Thomas et al., J. Biol. Chem. 266, 3744-3751, 1991; J. J. Holmes et al., Proc. Natl. Acad. Sci. U.S.A. 87, 5837-5841, 1990; P. Branch et al., Nature 362, 652-654, 1993; A. Kat et al., Proc. Natl. Acad. Sci. U.S.A. 90, 6424-6428, 1993; K. Wiebauer et al., Nature 339, 234-236, 1989; K. Wiebauer et al., Proc. Natl. Acad. Sci. U.S.A. 87, 5842-5845, 1990; P. Neddermann et al., J. Biol. Chem. 268, 21218-24, 1993, Kramer et al. Mol. Cell. Biol. 9:4432-40, 1989; Kramer et al. J. Bacteriol. 171:5339-5346, 1989 and references cited therein). It is generally desirable to utilize more than one mismatch repair assay before classifying a sequence change as a polymorphism, since some mutations will have effects that will not be observed in all assays.

For example, as discussed herein a mismatch repair gene containing a mutation would not be expected to be able to replace an endogenous copy of the same gene in a host cell without detectably affecting mismatch repair in that cell; whereas a mismatch repair gene containing a sequence polymorphism would be expected to be able to replace an endogenous copy of the same gene in a host cell without detectably affecting mismatch repair in that cell. We note that for such "replacement" studies, it is generally desirable to introduce the gene to be tested into a host cell of the same (or at least closely related) species as the cell from which the test gene was derived, to avoid complications due to, for example, the inability of a gene product from one species to interact with other mismatch repair gene products from another species. Similarly, a mutant mismatch repair protein would not be expected to function normally in an in vitro mismatch repair system (preferably from a related organism); whereas a polymorphic mismatch repair protein would be expected to function normally. In particular, some hMsh2 mutant proteins will probably have lost the ability to bind to mismatched base pairs.

We note that the methods described herein allow identification of different kinds of mismatch repair gene mutations. In particular, without wishing to be bound by any particular theory, we point out that it is possible that some mismatch repair gene mutations could actually improve the efficiency and/or accuracy of mismatch repair in a cell. Some such mutations would probably not be expected to confer susceptibility to cancer and/or to be associated with tumor development.

Particularly preferred assays that can be used to distinguish mismatch repair gene mutations from polymorphisms are presented in Examples 12-15 below. In some cases, it may be valuable to use more than one of these assays when making a determination about the effects of a particular mismatch repair gene sequence alteration. For example the "Dominant Mutator Assay" described below in Example 12 can advantageously be combined with the "Mismatch Binding Assay" described in Example 13 to identify mutations in a hMSH2 gene that affect the ability of the encoded hMsh2 protein to bind to mismatched base pairs. Of course, these assays can also be used to determine the effects of mismatch repair gene sequence alterations that have been engineered in the laboratory and are not necessary known to be associated with an HNPCC (or other cancer-susceptible) lineage and/or with a tumor.

We have already discussed various mutations that have been identified in human mismatch repair genes. The same studies have also identified human mismatch repair gene polymorphisms. In particular, our sequencing studies, described above, have identified a polymorphism in the hMSH2 gene:

(i) a C or a T at position 399 of the hMSH2 cDNA sequence set forth in SEQ ID NO.:45.

Also, Leach et al. supra have identified the following hMSH2 polymorphism:

(i) C to T transition in the polypyrimidine tract 6 bp upstream of exon 13, which exon begins at nucleotide position 2006 of the hMSH2 cDNA sequence set forth in SEQ ID NO.:45. We note that the same C to T transition was identified by Fishel et al. supra and it is possible that this change is not a truly silent polymorphism. That is, this change may in fact be a weak mutation, whose effects are not apparent (or are not significant) unless, for example, the cell contains additional, mismatch repair defects. For example, other mismatch repair gene mutations, particularly hMSH2 gene mutations, may have more dramatic phenotypes in cells that also have this C to T transition (e.g. this transition may increase the penetrance of other mutations).

Our research has indicated that a substitution of C for T in the intronic splice acceptor site six bares upstream of position 2006 MSH2 (SEQ ID NO:45) (exon 13, SEQ ID NO:78) is a polymorphism.

Our research has also indicated that a three base pair deletion removing codon 596 of the MSH2 gene (SEQ ID NO:45) is indicative of colon cancer. Furthermore, our research has also indicated that a C to T change at nucleotide position 1801 of the MSH2 gene (SEQ ID NO:45) creates a nonsense codon in place of the GLN codon 601, while a deletion of 2 bp, AG at nucleotide positions 1985 and 1986 causes a frame shift. These mutations are indicative of cancer.

Muir-Torre syndrome is thought to be a variant of Lynch syndrome (Lynch, et al., *Br. J. Dermatol* 118:295-801 (1985)), and this has been supported by recent linkage studies of Muir-Torre kindreds (Hall, et al., *Eur. J. Cancer* 30A:180-182)). We have analyzed two Muri-Torre kindreds for the presence of msh2 mutations and have identified a nonsense mutation and a frame shift mutation in exon 12 of MSH2, discussed above, that are linked to inheritance of cancer susceptibility in these kindreds. Both of these mutations are predicted to lead to the synthesis of truncated MSH2 proteins lacking the most conserved region of MSH2 (Fishel, et al., Cell 75:1027-1038 (1993), Leach, et al, *Cell,* 75:1215-1225 (1993)). In vitro mutagenesis studies have shown that this conserved region contains an ATP binding site that is essential for production of a functional protein (Haber and Walker, *EMBO J.* 10:2707-2715 (1991)). Thus, in these kindreds, affected members inherit one copy of an MSH2 gene that produces a nonfunctional protein; presumably loss of the second copy of MSH2 leads to repair-defective cells that can progress to become tumor cells.

Using the information provided by us herein one of ordinary skill in the art could readily identify other mutations and polymorphisms in mismatch repair genes and gene products.

EXAMPLE 12

Dominant Mutator Assay

Introduction of the hMSH2 gene into bacterial cells (*E. coli* cells in particular) results in a dominant mutator phenotype (Fishel et al., 1993 supra). A similar dominant mutator phenotype has been observed when the *S. pneumonae* MutS homolog, HexA, is expressed in *E. coli* (see Prudhomme et al. J. Bacteriol. 173:7196-203, 1991). A likely explanation for this effect is that the heterologous MutS homologues (e.g. HexA or hMsh2) are capable of binding to mismatched basepairs in *E. coli* cells, but do not interact productively with other components of the *E. coli* mismatch repair system (i.e. with MutL, MutH, etc.) and therefore prevent repair of the mismatched basepairs to which they bind.

We have developed an expression construct, pTTQ18-MSH2, into which MSH2 sequence alterations, such as those identified in HNPCC kindreds or found to be associated with particular tumors, can be introduced. pTTQ18-MSH2 is derived from pTTQ18 (Stark Gene 51:255-267, 1987) by insertion of a hMSH2 cDNA sequence (SEQ ID NO.:1) that has been modified to have useful cloning sites at its N-terminus.

One advantage to the pTTQ18 vector is that it is fully inducible with IPTG and appears to be completely "off" (i.e. appears not to be expressed even at a low level) in the absence of IPTG. These characteristics are valuable because even a low level of expression prior to induction with IPTG could lead to accumulation of mutations that could complicate interpretation of results analyzed after induction, and/or could affect, for example, expression level from or copy number of the vector.

Briefly, hMSH2 sequence alterations are introduced into the pTTQ18-MSH2 expression using any technique known in the art (see, for example, Sambrook et al. supra; *Directed Mutagenesis* McPherson, ed. IRL Press at Oxford University Press, 1991, incorporated herein by reference) including PCR protocols (see, for example, *PCR Protocols: A guide to methods and applications* Innis et al. ed., Academic Press, San Diego, Calif., 1990; *PCR Technology: Principles and applications for DNA amplification* Erlich et al. ed., Stockton Press, NY, N.Y., 1989). Altered constructs can be sequenced, for example using 15 lanes (of 36 available) of an Applied Biosystems 373A sequencer, to be certain that they contain only the desired change(s). Altered constructs are then transformed into bacteria, and the rate of accumulation of $Rif^r$ mutations is determined using known techniques (see, for example, Prudhomme et al. supra; Fishel et al. supra), and is compared to the rate observed in the presence of a non-altered construct. It is desirable to analyze at least five independent transformants for each altered construct. An approximately ten-fold reduction in the rate of accumulation of Rif$^r$ mutations is considered a sufficient decrease in hMSH2 function that the sequence alteration is classified as a mutation.

EXAMPLE 13

Mismatch Binding Assay

Another way to assay the effects that particular hMSH2 sequence changes may have on the function of the hMSH2 gene or gene products, and thereby to classify those sequence changes as "mutations" or "polymorphisms", is to assay the ability of an encoded hMsh2 protein to bind to mismatch basepairs.

hMsh2 protein has been overproduced and substantially purified from *E. coli* using a pET vector derivative construct that contains a hexa-HIS and factor Xa leader peptide at the hMSH2 N-terminus (Invitrogen, San Diego, Calif.). Preparation of a clarified bacterial extract followed by chromatography on a Nickel NTA column (Qiagen, Chatsworth, Calif.) resulted in a 500-fold enrichment of hMsh2 protein that is greater than 50% pure as judged by SDS-PAGE gel electrophoresis.

Mismatch binding by human mismatch repair proteins was studied using a gel-shift binding assay. Briefly, protein fractions are incubated with a $^{32}$P-labelled 39-basepair oligonucleotide duplex that was designed to minimize intra-molecular interactions (Oligo Designs), and also contained a GT mismatch at position 20. Incubations were done for 10 minutes at 23° C. in 20 mM Tris (pH 7.5), 50 mM KCl, 1 mM DTT, and 0.1 mM EDTA to allow formation of protein-DNA complexes. Several different competitor nucleic acids (e.g. poly dI-dC, an otherwise identical 39-mer that lacked the mismatch, and/or unlabelled mismatched substrate) were added to minimize nonspecific binding. Reactions were then loaded onto a 6% acrylamide gel in TBE, and were electrophoresed. The results suggested that hMsh2 binds specifically to oligonucleotide DNA containing a mismatch. The results further suggested that the on-off rate for mismatch binding for hMsh2 may be an order of magnitude slower for mismatch-containing DNA than for homoduplex DNA, and that hMsh2 protein produced by the above method is stable to freezing, is stable during incubation times of up to 4 hours at 37° C., demonstrates detectable mismatch binding activity without cleavage of the hexa-HIS leader peptide, and has high affinity for multi-nucleotide, looped-mismatch-containing DNA.

A "Mismatch Binding Assay" can also be used to identify mutations in hMLH1 gene sequences. pET-based expression vectors similar to the hMSH2-overproducers described above have been constructed to overproduce hMLH1. Clarified bacterial extracts prepared from *E. coli* cells containing such pET-hMLH1 constructs are capable of "supershifting" (i.e. of producing a higher molecular weight shift) the hMsh2-mismatch complex described above. This observation suggests that the hMsh2 and hMlh1 proteins interact with one another, and provides the basis for identifying mutations in hMLH1 and/or hMSH2 that disrupt or enhance the interaction of the hMsh2 and hMlh1 proteins. For example, changes in hMLH1 gene sequences (e.g. SEQ ID NO.:155) that result in production of an hMlh1 protein that does not supershift the hMsh2-mismatch complex, or that supershifts it to a reduced or increased extent, or to a different position, can be classified as hMLH1 mutations. Similarly, sequence changes in hMSH2 gene sequences (e.g. SEQ ID NOs.: 45 and 82-113) that result in production of an Msh2 protein that can bind to mispairs but cannot be supershifted by interaction with hMlh1, or is supershifted to a reduced or increased extent, or to a different position, can be classified as hMSH2 mutations. hMLH1 and hMSH2 sequence changes that do not affect the extent of supershifting and the position of the supershifted band are likely to be polymorphisms. However, given that individual mismatch repair activity assays such as this Mismatch Binding Assay typically test only one or a few aspects or activities of a mismatch repair component or components, it is often desirable to perform multiple different activity assays, preferably detecting different aspects of mismatch repair activity, before definitively classifying a sequence change as a polymorphism versus as a mutation.

EXAMPLE 14

Protein-Protein Interaction Assay: a Genetic Assay for hMsh2-hMlh1 Interactions

A Protein-Protein Interaction Assay can also be used to analyze sequence alterations in mismatch repair genes and to classify them as mutations or polymorphisms. In *E. coli*, the MutL protein increases the size of the footprint observed when MutS is bound to DNA containing a mismatch. It is likely that MutL serves as a bridge between MutS protein bound to a mismatch and MutH protein bound to a nearby Dam site.

A yeast Two-Hybrid system has been used to demonstrate that hMsh2 and hMlh1 proteins, like the bacterial MutS and MutL proteins, interact with one another. Specifically, the hMsh2 protein has been fused to the DNA-binding domain of Gal4 (pAS1-hMSH2) and the hMlh1 protein has been fused to the activation domain of Gal4 (pACTII-hMLH1) (Harper et al. Cell 75:805-16, 1993). The GAL4 promoter has been constructed to be upstream of a β-galactosidase reporter gene. An intact Gal4 protein will activate transcription of this β-galactosidase reporter gene, producing a blue colony in which β-galactosidase activity has increased significantly, typically several-thousand-fold. When the Gal4 DNA binding domain and Gal4 activation domain are separated from one another, no activation of β-galactosidase expression occurs. However, if these domains are brought together by fusion to proteins that interact with one another (in this case, by fusion to hMsh2 and hMlh1), activation of β-galactosidase expression is observed.

Neither the (Gal4 binding domain)-hMsh2 fusion nor the (Gal4 activation domain)-hMlh1 fusion alone stimulates β-galactosidase activity. However, when both constructs are present in the same cell, β-galactosidase activity increases approximately 100-fold. Mutations in hMSH2 and MLH1 can therefore be identified by their quantitative effect on β-galactosidase expression in this Two-Hybrid assay system. hMSH2 or hMLH1 sequence alterations that result in greater than or equal to an approximately two-fold decrease in β-galactosidase activity in this assay can be classified as mutations rather than polymorphisms. hMSH2 or hMLH1 sequence alterations that result in greater than or equal to an approximately two-fold increase in β-galactosidase activity in this assay are also likely to represent mutations. hMSH2 or hMLH1 sequence alterations that do not affect the level of β-galactosidase activity detected in this assay are likely to be polymorphisms. However, given that individual mismatch repair activity assays, such as this Two-Hybrid assay, typically test only one or a few aspects of activities or a mismatch repair component or components, it is often desirable to perform multiple different activity assays, preferably detecting different aspects of mismatch repair activity.

EXAMPLE 15

Analysis of Possible Mutations in Human Mismatch Repair Genes by Investigating the Effects of Similar Changes in Homologous Yeast Genes Another possible way to distinguish polymorphisms from mutations is to utilize an assay system in which a detectable phenotype is under the control of a mismatch repair gene. That is, any system in which a particular behavior requires a functional mismatch repair gene and a change in that behavior is detectable, could be used to categorize different mismatch repair gene alleles as "mutant" or "polymorphic".

In particular, a Saccharomyces cerevisiae system could be used for quantitatively analyzing the effect of particular mutations on the mismatch repair pathway. Given the relatively high level of conservation between yeast mismatch repair genes and their known human homologues (e.g. between yeast and human MSH2, and between yeast and human MLH1; see FIGS. 3 and 4), it is likely that, in many cases, it will be possible to make changes in the S. cerevisiae mismatch repair gene sequence that are equivalent to sequence changes observed in human mismatch repair genes in HNPCC kindreds. The effects of those changes can then be studied in the yeast system, for which mismatch repair assays have been well characterized (see, for example, D. K. Bishop et al., Mol. Cell. Biol. 6, 3401-3409, 1986; E. Alani et al., Genetics 137, 19-39, 1994; R. A. G. Reenan et al., Genetics 132, 963-973, 1992; R. A. G. Reenan et al., Genetics 132, 975-985, 1992; L. New et al., Mol. Gen. Genet. 239, 97-108, 1993; E. Alani et al., J. Biol. Chem. In preparation, 1994; N.-W. Chi, J. Biol. Chem. Submitted, 1994; T. A. Prolla et al., Science in preparation, 1994; M. Strand et al., Nature 365, 274-276, 1993) to determine if the sequence change represents a mutation or a polymorphism. This sort of approach will likely be most successful for sequence changes that result in substitutions of amino acid residues at positions that are conserved among all known mismatch repair gene homologues and that are found within a block of conserved amino acid residues. There are likely to be many such mutations that are responsible for conferring susceptibility to various cancers and/or that are associated with tumor development.

For example, the above-mentioned HNPCC-associated hMSH2 C to T transition at codon 622 results in substitution of an amino acid residue (Pro 622) that is conserved in 11 of 11 known MSH genes. Similarly, the tumor-associated hMSH2 C to T transition at nucleotide position number 1915 (see above) results in substitution of a tyrosine residue for histidine 639 (His 639). His 639 is conserved in 10 of 11 known MSH genes; and the hMLH1 Ser 44 to Phe change affects a highly conserved residue. These same amino acid changes can be made in the corresponding S. cerevisiae genes by altering a single nucleotide.

In the cases of nonsense and frameshift mutations where the mutations lead to the synthesis of a truncated protein, a mutation can be made in the S. cerevisiae gene to produce a truncated protein that is similar to that produced by the mutant human gene in that essentially the same region was eliminated from both proteins.

For example, the above-described 2-basepair deletion of hMSH2 nucleotides 1985 and 1986 can be reproduced in a yeast system. This mutation results in a frameshift that introduces 11 new amino acids beginning at hMsh2 amino acid number 663 (see SEQ ID NO.:2), and then prematurely terminates the polypeptide chain, eliminating the most highly conserved region of the hMsh2 protein (see FIG. 3). A 2-basepair deletion of the analogous S. cerevisiae nucleotides will cause a similar frameshift mutation that both eliminates the conserved region of the protein by premature translation termination and produces a mutant protein that has 11 new amino acids at it's C-terminus. Five of the 11 amino acids that will be introduced into the S. cerevisiae mutant protein are identical with the corresponding amino acids introduced into the mutant form of hMsh2.

A second example of such a mutation that may be studied in a S. cerevisiae system is the above-mentioned Arg 406 to Opal stop codon change. A similar change, introducing an Amber stop codon, can easily be made in the analogous codon of the S. cerevisiae gene, resulting in production of a similar truncated protein.

Small, in frame deletion mutations may also be made in yeast genes to produce mutant proteins that are quite similar to the proteins produced by mutant human genes. An example of this is the hMSH2 splice site mutation that results in skipping of exon 5 and hence results in a mutant protein from which amino acids 265 to 314 are deleted. In this case, an in frame deletion can be made in the S. cerevisiae gene, resulting in the synthesis of a protein from which the corresponding amino acids had been deleted.

Another way to analyze mismatch repair gene sequences and to identify mutations versus polymorphisms is to utilize a yeast strain in which mismatch repair depends upon functional human mismatch repair proteins and/or upon functional yeast/human chimeric mismatch repair proteins.

These types of studies can be performed using standard plasmid expression systems. For example, the S. cerevisiae MSH2 and MLH1 genes, under control of their native promoter, have been cloned on low copy CEN vectors containing a variety of selectable markers. Selected mutations can be made in these genes using standard site directed mutagenesis techniques to introduce the mutations of interest. Sequencing studies can confirm the presence of the mutation and can also verify that no additional mutations have been introduced.

Mutated msh2 plasmids can then be transformed into isogenic wild type and msh2 null mutant strains; and mutated mlh 1 mutant plasmids can be transformed into isogenic wild type and mlh 1 null mutant strains. Control strains could include the isogenic wild type, msh2 null mutant and mlh 1 null mutant strains transformed with the cloning vector; isogenic wild type and msh2 null mutant strains transformed with the wild type MSH2 plasmid; and isogenic wild type and mlh 1 null mutant strains transformed with the wild type MLH1 plasmid.

All of the resulting strains can be tested to determine the effects of the introduced nucleotide change using, for example, fluctuation analysis and established mutagenesis assays such as, for example:

1) the forward mutation to canavanine resistance (see R. A. G. Reenan et al., Genetics 132, 963-973, 1992; R. A. G. Reenan et al., Genetics 132, 975-985);

2) the reversion of a frameshift mutation in LYS2 (see L. New et al., Mol. Gen. Genet. 239, 97-108, 1993); and 3) CA repeat instability using a CA repeat containing plasmid vector (see Strand et al. Nature 365:274-276, 1993).

The presence or absence, as well as the extent, of a mutant phenotype can be determined by comparing the results of these assays for null strains transformed with these mutagenized plasmids with the results of these assays for null strains transformed a wild-type allele of the appropriate mismatch repair gene and/or with the results found with wild-type (i.e. not null) strains. Generally, increased spontaneous mutation rates in strains containing mutagenized plasmids indicate that the change in the mismatch repair gene on the plasmid is a mutation (and not a polymorphism). Furthermore, comparisons of spontaneous mutation rates observed for strains transformed with different mismatch repair gene mutants allows determination of the relative severity of the mutations (stronger mutations result in higher mutation rates).

Comparison of mutagenesis assay results for wild type strains transformed with the mutagenized plasmids, for wild-type strains transformed with the wild type plasmid, and for non-transformed wild type strains further allows identification of "dominant negative" mutations, that interfere with mismatch repair in cells that have a wild type mismatch repair system. It may also be of interest to express each mutant on a high copy 2 micron plasmid to determine if overexpression of the mutant protein is required to cause a dominant phenotype or a stronger dominant phenotype than observed when the protein is expressed from a low copy number vector.

It is possible that the phenotypes caused by different MSH2 and MLH1 mutations could be quite subtle. For example, the magnitude of the effect of a specific mutation on the forward mutation assay that in principle can detect a broad spectrum of mutations, could be different than the effect observed in the reversion or CA repeat instability assay that detects frameshift mutations. These types of effects might be indicative of mutations that cause an alteration in the specificity of mismatch repair. Such types of MSH2 and MLH1 mutations might be found in tumors that do not show a repeat instability phenotype or show tri- and tetranucleotide repeat instability but not dinucleotide repeat instability. In such selected cases, it will be of interest to determine if the mismatch repair defect is restricted to specific types of mispairs. This could be analyzed, for example, by transforming the *S. cerevisiae* strains containing the msh2 or mlh 1 mutant plasmids with plasmids containing defined mispairs and measuring the frequency of repair of these individual mispairs. Previously developed plasmid systems for analyzing each of the 8 possible single base mispairs and different 1 and multiple base insertion mutations (see ref. D. K. Bishop et al., Mol. Cell. Biol. 6, 3401-3409, 1986; D. K. Bishop et al., Proc. Natl. Acad. Sci. U.S.A. 86, 3713-3717, 1989; B. Kramer et al., Mol. Cell. Biol. 9, 4432-4440, 1989) can be used for this analysis.

Of course, the *S. cerevisiae* system is suggested primarily for its ease of experimental manipulation. Similar studies could be performed in other cell types, such as, for example, human, murine, *Drosophila*, etc. using available mutagenesis, transfection, and assay systems.

This type of analysis should also allow us to determine if any particular types of mutations correlate with different phenotypic properties of HNPCC kindreds such as age of onset, occurrence of multiple tumors and occurrence of different types of tumors, and if the mutations that are found in sporadic tumors cause different phenotypes that the germ line mutations found in HNPCC kindreds.

EQUIVALENTS

It should be understood that the preceding is merely a detailed description of certain preferred embodiments. It therefore should be apparent to those skilled in the art that various modifications and equivalents can be made without departing from the spirit or scope of the invention.

What is claimed is:

1. An isolated nucleotide segment having the sequence as set forth in SEQ ID NO: 8.

2. A vector containing the isolated nucleotide segment of claim 1.

3. An isolated nucleic acid segment having a nucleotide sequence selected from the group consisting of SEQ ID NOs: 15, 17-23, 25, 26, 28, 42, 45-154, and 157.

4. A vector containing the isolated nucleotide segment of claim 3.

5. An isolated nucleotide segment, wherein said nucleotide segment is SEQ ID NO: 45.

6. The vector of claim 5, said vector is a retroviral vector.

7. An isolated nucleotide segment, wherein said nucleotide sequence is selected from the group consisting of SEQ ID NOs: 41, 42 and 45-50.

* * * * *

SEQUENCE LISTING

```
(1) GENERAL INFORMATION:

(iii) NUMBER OF SEQUENCES: 157

(2) INFORMATION FOR SEQ ID NO:1:

(i) SEQUENCE CHARACTERISTICS:
        (A) LENGTH: 5608 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Saccharomyces cerevisiae (vii) IMMEDIATE SOURCE:
        (B) CLONE: MSH2

(xi) SEQUENCE DESCRIPTION: SEQ ID NO:1:

TGTATCAACT AGTGAAGAAG AATTCCGCGC TAGAAGAACA AAGATAACAA GACTATGCCT        60

CTAAACTTAA AGAAAAGAA GCGCAATTAA AAAGTCAAAT GCAAATTTTG AAGTTAGAAA        120

CAACAAACAA GGCCTACAAA ACTAAATACA AGGAGGCTCT CTCGGAAAAT AAGAAAATAA        180

AAGAGGCTTT CAAAGAACTA GACAATGAGT CATACAATCA CGATGAGGAA TTACTAAAAA        240
```

| | |
|---|---|
| AATACAAATA TACTAGGGAA ACCTTAGATA GGGTCAATAG AGAACAGCAA TTAATCATTG | 300 |
| ATCAAAACGA GTTTTTGAAG AAAAGTGTCA ATGAACTACA AAATGAGGTT AATGCTACCA | 360 |
| ACTTCAAGTT CTCTTTATTT AAAGAAAAAT ATGCAAAATT AGCTGATAGC ATCACTGAAT | 420 |
| TGAATACCTC TACGAAAAAA AGAGAGGCCC TGGGAGAAAA CTTAACTTTT GAATGCAATG | 480 |
| AATTAAAAGA AATATGTTTG AAATACAAAA AAACATCGA AAATATATCA AATACCAATA | 540 |
| AGAATTTACA AAATTCGTTC AAAAATGAAA GGAAAAAAGT TTTAGATTTG AGAAATGAGA | 600 |
| GAAATTTGTT GAAAAAGGAA ATACTGTTGA TTGAATGTCA TGGTTCATAT TCTCTACTCC | 660 |
| TTGTATCTAA TATTCTGACA TGTTATCGGT TCTTACTGCC AAGTGATACT ATTATTGAAA | 720 |
| CTGAAAGCTT AATTAAGGAG CTACTCAACA TGAATAATTC ACTTTCGAAC CATGTGTCTT | 780 |
| CTTCTGACGA GCCTCCAGCG GAGTACTCGA AAAGATTAGA ATTAAAATGT GTAGAGTTTG | 840 |
| AGGAAAAGTT ACTTTATTTC TATCAAGAAC TTGTGACGAA GAAAATTATA GACGTCATTT | 900 |
| ACAAGTGCTT TATTAATTAT TACAAGAAAA GTAGGCAAAC TGACCAAAAA TCCAATCAGA | 960 |
| ACTCCAGCAC TCCGTATAAA CAAAGCCAAA GACAAGTTCC GCACTCCATC AAGTGAACCT | 1020 |
| CAACAGCTAC ACATTCTTTT ATAATCCTTA ATATTCTATA TATACATATA TGAAAAAATA | 1080 |
| GAAAACGCGA AAACTTGTCA TTTTTTTTTT AGGCGTTTTT ATAATATACT GAAAATAAAA | 1140 |
| AGAGGCTCTT TAAATGTTGA CACTCTACTC CAATATCAAC TGTAAAAAAT CTCTTTATCT | 1200 |
| GCTGACCTAA CATCAAAATC CTCAGATTAA AAGTATGTCC TCCACTAGGC CAGAGCTAAA | 1260 |
| ATTCTCTGAT GTATCAGAGG AGAGAAACTT CTATAAGAAG TATACAGGGT TGCCGAAGAA | 1320 |
| ACCATTAAAA ACCATTAGAT TAGTGGATAA AGGCGACTAT TACACAGTTA TAGGTTCAGA | 1380 |
| TGCGATATTT GTGGCAGATT CAGTCTATCA TACTCAATCT GTTTTAAAGA ACTGCCAATT | 1440 |
| GGACCCTGTA ACGGCAAAGA ACTTCCATGA ACCAACTAAA TATGTTACTG TTTCGCTACA | 1500 |
| AGTTCTTGCC ACTCTGCTGA AGTTATGTTT GTTGGATCTG GGATATAAAG TTGAGATATA | 1560 |
| CGATAAGGGT TGGAAATTAA TAAAAAGCGC ATCTCCAGGG AACATTGAGC AAGTTAATGA | 1620 |
| GCTAATGAAT ATGAATATTG ATTCGAGTAT CATCATTGCA AGTTTGAAAG TTCAATGGAA | 1680 |
| TTCCCAAGAT GGAAACTGCA TTATTGGAGT TGCTTTCATT GATACCACTG CATACAAGGT | 1740 |
| GGGAATGCTT GATATTGTCG ATAATGAAGT GTATTCCAAC CTAGAGAGTT TCTTGATTCA | 1800 |
| ATTGGGTGTA AAGGAATGTT TGGTGCAGGA CTTGACATCA AATTCAAACT CCAATGCTGA | 1860 |
| AATGCAGAAA GTAATAAATG TAATTGATCG CTGTGGGTGC GTCGTTACAT TATTGAAAAA | 1920 |
| CTCAGAATTT TCTGAAAAAG ATGTCGAACT GGATTTAACC AAGTTACTGG GCGATGATTT | 1980 |
| GGCATTATCG TTACCACAAA AATACTCTAA ATTATCTATG GGTGCATGCA ATGCATTGAT | 2040 |
| TGGATATTTA CAATTGCTCT CAGAGCAAGA TCAAGTAGGC AAGTATGAAT TAGTTGAACA | 2100 |
| TAAATTAAAG GAGTTTATGA AGTTGGATGC CTCCGCTATT AAAGCCCTTA ATTTATTCCC | 2160 |
| ACAAGGACCA CAAATCCAT TTGGTAGCAA CAATTTAGCT GTATCTGGAT TTACGAGTGC | 2220 |
| TGGTAATTCT GGTAAAGTAA CTTCTCTTTT CCAGTTACTG AATCATTGCA AAACAAATGC | 2280 |
| TGGTGTTCGG CTTTTAAATG AATGGTTGAA GCAACCACTG ACCAATATTG ACGAAATTAA | 2340 |
| TAAAAGACAT GATTTAGTCG ACTATCTAAT TGACCAAATC GAGTTAAGAC AGATGTTGAC | 2400 |
| TTCTGAATAT TTACCCATGA TTCCAGATAT TCGTAGATTG ACTAAGAAAT TAAATAAAAG | 2460 |
| AGGAAACTTA GAGGATGTCT TGAAATTTA CCAATTCAGT AAAAGAATAC CAGAAATTGT | 2520 |
| TCAAGTTTTC ACTTCGTTCT TGGAGGACGA CAGCCCCACT GAACCAGTAA ACGAACTGGT | 2580 |
| CCGCTCCGTT TGGCTAGCTC CTTTAAGCCA CCACGTTGAA CCTTTGTCCA AATTCGAAGA | 2640 |

```
AATGGTTGAA ACAACGGTTG ATTTGGATGC TTATGAAGAA AATAACGAAT TTATGATTAA    2700

AGTTGAGTTT AATGAGGAAT TAGGAAAGAT AAGAAGTAAA CTGGATACGT TGCGTGATGA    2760

AATTCATTCA ATCCATCTTG ATTCTGCTGA AGATCTAGGA TTCGATCCGG ACAAAAAACT    2820

GAAGTTGGAG AACCATCATC TGCATGGTTG GTGTATGAGG TTGACACGTA ATGACGCCAA    2880

GGAGTTACGT AAACATAAGA AGTACATTGA GTTGTCGACA GTAAAAGCTG GTATATTTTT    2940

TAGTACCAAA CAATTAAAGT CAATCGCCAA TGAAACCAAT ATTCTTCAAA AGGAGTACGA    3000

CAAGCAACAA TCGGCTCTGG TTAGAGAAAT TATAAATATT ACATTAACGT ACACACCAGT    3060

TTTTGAAAAA CTATCCTTAG TCTTAGCGCA TTTAGATGTG ATTGCCTCTT TTGCTCATAC    3120

TTCCTCGTAT GCTCCTATAC CATACATTAG ACCCAAGTTG CATCCCATGG ATTCGGAAAG    3180

AAGAACTCAC CTAATAAGCT CCCGTCATCC AGTACTGGAA ATGCAAGACG ATATAAGCTT    3240

TATATCTAAT GATGTCACAT TAGAGAGTGG AAAGGGCGAC TTTTTAATCA TAACTGGACC    3300

AAACATGGGA GGTAAATCTA CTTACATCAG ACAGGTTGGT GTGATTTCTT TAATGGCCCA    3360

AATTGGTTGT TTCGTACCTT GTGAAGAAGC TGAAATAGCC ATAGTAGATG CAATTCTTTG    3420

CAGGGTCGGG GCAGGAGATT CCCAATTGAA AGGTGTTTCC ACATTTATGG TTGAAATATT    3480

GGAAACTGCT TCTATACTAA AGAATGCGAG TAAGAATTCT TTGATTATTG TAGATGAACT    3540

AGGGCGTGGT ACTAGTACAT ATGATGGTTT TGGTCTAGCT TGGGCAATTG CTGAACATAT    3600

CGCAAGTAAG ATTGGATGTT TCGCTTTGTT TGCAACTCAC TTTCATGAAT TGACAGAATT    3660

GTCTGAAAAA TTGCCCAATG TCAAGAATAT GCATGTTGTT GCACATATCG AGAAAAATTT    3720

AAAAGAACAA AAACATGACG ATGAGGACAT CACGTTGTTA TACAAAGTTG AGCCTGGTAT    3780

TTCAGATCAG TCTTTTGGTA TTCATGTTGC AGAAGTTGTT CAATTTCCAG AAAAAATTGT    3840

TAAAATGGCT AAACGTAAAG CCAATGAATT GGACGATCTA AAAACTAATA ATGAAGATTT    3900

GAAAAAAGCT AAGCTATCAT TACAGGAAGT TAACGAAGGT AATATTCGTT TGAAGGCTTT    3960

ACTGAAAGAG TGGATTAGAA AAGTGAAGGA GGAGGGTTTA CATGACCCAA GCAAAATTAC    4020

TGAAGAAGCT TCCCAGCATA AAATACAAGA GCTATTGCGT GCTATAGCAA ATGAACCAGA    4080

AAAGGAAAAC GATAATTACC TTGAAATATA TAAAAGCCCT TGTTGTTATA ATTAATATTA    4140

CAACGACATC TTAAGTGAGA ATCGATAGAT AATATATAGA TACAAATAGT ACATATAATA    4200

TGCATTGGAA AGAATTTTAT TTTTTACAAT CTTTGTAGAC AAGGTACAGT TTATTCATAA    4260

TCCCTAAAAG TGTTCACGAA AGAATAATCT CTGTCATAGA TCAATTTTCC TAAAGGCAAT    4320

AAGGCTCTAA AAGCTTCGAA ATCTTCCTTT ATTCCACTGT CACTATTAAA ATTAGAATTT    4380

TCAGGGGTCT CTAGACCACT GGAAAGAGTA TCTCCGGTAT CAGAACTATG GATGGGATAA    4440

ACAAGAGATG TTAGGTCCGA ACGAATTGGG TACAAAGATG AGTCATCAGA TATTCCTTTC    4500

CTATTTGAAG ATGGCGATAG GTCTCCAAAA TTTGAGATGG GGGAGTGAGA TTTTAATAGT    4560

TTTAAAATTT CGACTGATAA CTCTCCAAAT AAGTTTATTG GTGCTTCCTC CGCAAAGTCT    4620

TCTGAAGAAA TATCATTCGT ATTCAGTCCA TCATCGGCGA GATCGGCTTC GTTGCCCTTT    4680

TGTAAAGAAT GGAGAGAACC ATATGATTTT AGACTCATAA TTAGTTGATC GACTGTTTCA    4740

TCTTTTATCT TTCTTGAATG CATAATAACT TTCGTTATCG TTTCATCATA AGGTTTAGAA    4800

TCAAATATTG ACGTAGAATC GTTCAAAGCA TGATAACGTT GCAAACGTA TTTCAAAAAG    4860

TGGCTGTAGA ACACAATCAA AGTGTTCCAT TTGACATTGT CAAACAGCTC ATCATTTTCT    4920

CCCACTAATC GATCATAAGA TTTTTTTAGG ATATCGATGA TCTCTTTTAC CTCACCTTTC    4980
```

-continued

```
TTTTTTAGAT CGTTCATATT ATCCACAACG TAAAAGAAGA GAACAAACAT AGCAGTAGAG    5040

AACTGATACA TAACCTCGTT ATACATATGC GCCTGGTAAT TGATGCCTTG AAACAGCTGT    5100

AACATTTCTT TACTGGCGTT TAAGTATTGA CTTGAAAAAA GAATGAATAG CTGAGGAATA    5160

TCATGGCGAG AACCTTTGTA TAGGCGTTCG TTATCAATCA ATAAGGATGT AGTCATCATG    5220

CTCAAAATCA CTTTAGAATA TAGCGCCCTA AAATGACAAT TCAAACACG AGAGCATGCA     5280

ATCTCAAAAC TTAAAGCCGG ATTTTCTTGG GATTTTTGAG CGTAAAGTAC CGATAAATAC    5340

TGTTTATAAC TTTTTAGTTT CATACTTACG TGCAAGTTGT CTCTCCAATT GTTCAAAGAA    5400

TCATTGAGAT CTTTGATTTT ATCAAGCATG GCATCGAATG AAAGATCTAG AGTACTTCTG    5460

ACAGCAAAAC AAGTAGAGTA TATTTTACTC TCAATACTAA CCAATTTTGA AACATAATAT    5520

GATATGAAAA GGGATATGTG CTGACAAAAA TTTACAACTA CATTCAATGC AGAGTTGACA    5580

TCAGTAATTT TATCGAGATC CACAGGAC                                      5608
```

(2) INFORMATION FOR SEQ ID NO:2:

(i) SEQUENCE CHARACTERISTICS:
        (A) LENGTH: 4410 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Saccharomyces cerevisiae (vii) IMMEDIATE SOURCE:
        (B) CLONE: MSH1

(xi) SEQUENCE DESCRIPTION: SEQ ID NO:2:

```
ATGTATCTAT GCACTGCGTG ATATCGCGGC AAGCGAAGAG TTGACATATG ATTACAAATT      60

TGAGAGAGAA AAGGATGACG AGGAAAGACT TCCTTGTTTA TGTGGAGCAC CTAATTGTAA     120

AGGTTTCTTG AACTGACGAT GATACATTGA TTTGTTTGGA GCTTCCTGAT TTAACATATC     180

GTTGCTTTCC AGCAAAAGGT AAAGATAAAT ACTAAACTGT ATACATCTAT AAGTAATCTC     240

GGCCATTATT TTAACGATTA GTACTTTTGT TCGTGTCATT TTTTTGGAAA ATTTTGCGAT     300

CTCTCACTGT TGAAGAATAA AGATTTCGCG ATGACTTTTG CTTGCAGAGA AATGCCTGAA     360

AACACGAACA TTCAATAATA TAGATGGTAC ATAACATATG CGCAAGAAAA CGTAAAGGCC     420

ACGGATGAAG CATTTCTTTA GGCTACCGAC AGCATTCCGG CCCATTTCTA GGGTTTCCTT     480

ACGATATTCT AGTACTGATA CCGCTCAACC AAAAATATCA AAACTCAAAA TTAGTTTTAA     540

TAAAATTTCT GAATCAAATA GCGAAAAAAA AGATAATTTG GGTTCAATTG ACACACGAAA     600

TTGTCTTTCG ACTCAGCAAG ATGACAAACT ATCAAGCACT GAGCCCTCGA AGGCTTCCCT     660

TCCACCATCA TTACATATG TTCGTGACTT GATGGATTTG TATAAGGATC ATGTGGTTTT      720

AACACAAATG GGGTCATTTT ATGAACTTTA CTTTGAACAA GCAATTAGAT ACGCTCCAGA     780

ATTAAATATA TCATTGACGA ATCGAGCTTA TAGTCATGGC AAAGTTCCAT TTGCTGGGTT     840

TCCTGTACAC CAGTTAAGTC GACATTTAAA AATGCTTGTT AACAATTGCG GATACAGTGT     900

AACTATCGCA GAGCAATTCA AAAAAAAGGA CGTGGCAGAT AATGAAGCCA ATAAATTCTA     960

TAGGAGAGTG ACTAGAATCG TTACTCCCGG CACTTTTATT GATGAAGCAT TTGAAAATTT    1020
```

```
GAGGGAAAAT ACATATCTCC TGAACATCGA ATTTCCTGAA AACTGTATGA GTCAAGTGGC    1080

AGACACGAGT CTAAAAGTTG GTATATGTTG GTGTGATGTG AGTACTGGGG AGATATTTGT    1140

TCAACAAGTG TATCTTAGAG ATTTGGTTTC TGCAATAACA AGAATTCAAC CTAAGGAGAT    1200

TTTATTAGAT GAAAGATTAC TTGAGTTTCA TATCGAGTCA GGGACGTGGT ATCCTGAACT    1260

TGTTGAGCTT AAAAAATTTT TTATAAAATA TCAGAAAATG CCCAGTCAAC ATCGCACTAT    1320

TGAATCATTC TATGGGCTGT TTAATTTGGG AGGTAAAGAA GCAACGGAAA GGCAATTGAA    1380

AATCCAATTT CAAACTTTTA CTCAGAAGGA GTTAGCTGCT TTGAGGAATA CATTAATATA    1440

CGTAAGTAAT CATCTACCTG ATTTCTCTAT TAATTTTCAG ATTCCTCAGA GACAATTAGC    1500

AACGGCGATA ATGCAAATTG ATTCAAGAAC CAGCACTGCA CTTGAATTGC ATTCTACTGT    1560

AAGAGACAAC AATAAAAAAG GCTCTCTGTT ATCATCTATA AGAAGGACAG TTACACCTTC    1620

AGGAACAAGA CTTCTGTCTC AATGGTTGAG TGGACCTTCC CTTGATTTGA AGAAATTAA    1680

AAAGCGTCAG AAAATTGTAG CATTTTTCAA AGACAACCGT GATATCACTG AAAACCTACG    1740

GACTATGTTG AAAAAAGTAA ATGATCTATC CCGTATACTT CAAAAGTTTA GTTTCGGAAG    1800

GGGCGAGGCA TTAGAACTTA TTCAAATGGC ACGTTCACTA GAGGTTTCAA GAGAAATAAG    1860

AAAATATTTA CTAAATAACA CGTCGTTGAT GAAAGCTACA TTAAAGAGTC AAATCACACA    1920

GCTGACTGAG TCTTTAAATT TTGAAAAAAA TTTGATTGAT GATATTTTGA AGTTTTTAAA    1980

TGAGGAAGAG CTAGCAAAGT CACAAGATGC TAAACAGAAT GCAGATGTAA CTAGAATGCT    2040

TGACATAGAT GTAAAAGACA AGAAAGAAAG TAACAAAGAT GAGATTTTTG AATTAAGAGA    2100

TTTTATCGTA AACCCTTCGT TCAATACCAA ACTTAGGAAA TTGCATGACA CTTATCAGGG    2160

CGTTTGGCAA AAAAAAACTG AGTACAATGC TTTATTAAAA GGTTTTTTTG TTGGCGACCT    2220

AGGTGCTAAG ACTTTCACCT TGAAGGAAAG GCAAAACGGT GAGTATGCCC TCCATGTGAC    2280

AGGAACAGCC TCTAGTTTAA AGAAAATTGA TGAGTTAATT AGTAAATCGA CGGAGTACCA    2340

CGGAAGTTGC TTCCATATTT TGCAAAAATC AAGCCAAACA CGATGGTTGA GTCACAAAAT    2400

TTGGACAGAC TTGGGGCACG AGTTGGAATT ATTAAATTTA AAGATTAGGA ATGAAGAGGC    2460

TAATATTATT GATCTTTTTA AAAGGAAATT TATTGATAGA AGTAACGTGG TCAGACAAGT    2520

TGCAACTACA CTGGGCTATC TTGATACCTT ATCGTCCTTT GCTGTGTTAG CTAACGAGAG    2580

AAATTTAGTC TGCCCAAAAG TGGATGAGAG CAATAAACTA GAAGTAGTGA ATGGGAGACA    2640

TCTAATGGTT GAAGAGGGTC TTTCCGCGCG CTCTTTGGAG ACATTCACGG CCAATAACTG    2700

CGAATTGGCG AAGGACAATT TATGGGTAAT TACCGGTCCG AATATGGGTG GTAAATCTAC    2760

ATTCTTAAGA CAGAATGCAA TTATAGTCAT TCTGGCGCAA ATTGGATGTT TTGTTCCATG    2820

CAGTAAGGCG CGTGTGGGTA TTGTAGATAA GCTTTTTAGC CGAGTTGGTT CAGCAGATGA    2880

TCTGTACAAT GAGATGAGTA CGTTCATGGT TGAGATGATA GAAACGTCGT TCATCTTGCA    2940

AGGAGCTACG GAACGGTCTT TAGCTATTCT AGATGAGATT GGCCGAGGGA CTAGTGGTAA    3000

AGAAGGCATT AGCATCGCTT ATGCAACTTT AAAGTATTTG TTAGAGAACA ATCAATGCAG    3060

AACGCTTTTT GCTACACATT TTGGTCAAGA ACTGAAGCAA ATCATTGATA ACAAATGTTC    3120

GAAAGGAATG AGCGAAAAGG TCAAGTTTTA CCAAAGCGGA ATCACTGATT AGGTGGAAA    3180

CAATTTTTGT TACAACCATA AGTTGAAGCC GGGCATCTGC ACGAAATCAG ATGCCATTAG    3240

AGTTGCGGAA TTGGCCGGAT TTCCAATGGA AGCGTTAAAA GAAGCCCGCG AAATATTGGG    3300

ATAACTTTTG AATACAACTA TTAATTGTAT ATAATTTGAC ATGTAATATA ATAAGATGTG    3360

GAATCAATTT CCCTGTCTTT TTTTTCAAAA GCGACTGTGA AGATACTTAG AAAATGGCAA    3420
```

```
AAACGGTAGT TTGCAAATTT CCGTAGTTTG TCGCGCGAAT GATATTAGCG GAAACAAAAC    3480

GATCAAACCT TATACCATGA ATATAATGGT GGATATTTAT TACGGTAAGG AAACACTCTG    3540

AGCCAGGCTT GTAAATAGCG GTTATCTAAG CTTGTAACTA AAGAAATCAA TTTGCATCTT    3600

TCGTCCATGA GTGTCAGCCT TGAGCAAACG CTCGGATTCA GAATAAAAGT TACGCACGTG    3660

TTGGATGTAG TTACTGAAGG AAGATTGTAT TCGTTCAATT CATCCAACAA CACTCTTACT    3720

ATCCAAACAA CAAAGAAGAA TCAATCTCCA CAAAACTTCA AGGTGATAAA ATGTACATTC    3780

ATCAAGCATT TGGAAGTCAT TGGTGATAAG CCCTCGTTTA ACTCATTCAA AAAGCAACAA    3840

ATCAAACCCT CATATGTCAA CGTGGAAAGA GTTGAGAAGC TTTTGAAAGA AAGTGTAATA    3900

GCATCTAAAA GAAAGAACTC TTAAGGGCAA GGGTGTGAGT GCAGAGGGTC AGTTCATTTT    3960

CGATCAAATC TTCAAGACCA TAGGAGATAC TAAGTGGGTG GCTAAAGACA TCATTATTCT    4020

TGATGACGTT AAGGTGCAAC CTCCATACAA GGTCGAAGAT ATCAAAGTGC TACATGAGGG    4080

AAGTAACCAA TCCATTACAT TAATTCAAAG AATAGTGGAA AGAAGCTGGG AGCAGCTAGA    4140

ACAAGACGAT GGTAGGAAAG GCGGATAGAT TAATTAATGA CGGAAACGAT AATATACGTT    4200

ATATATTTTT ATCCGTACTT CTATAATGTC AACTATTGTT TATAAAGAGA TCCATTTGAG    4260

TCTACAGATT TTTCTATTTA TCAAACTATA ATATTCCACC ACTCTCTTCT CAGTCGCAAT    4320

GCTTGGGTGT ACGGTGTTTG AATAATTGAA TTAGATTTAA AGCGAATAAG TGATGACTAA    4380

CAAGCAAAAA AATCGAGTAT TTCAAGATCC                                      4410
```

(2) INFORMATION FOR SEQ ID NO:3:

(i) SEQUENCE CHARACTERISTICS:
        (A) LENGTH: 966 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Saccharomyces cerevisiae (vii) IMMEDIATE SOURCE:
        (B) CLONE: Msh2

(xi) SEQUENCE DESCRIPTION: SEQ ID NO:3:

```
Met Ser Ser Thr Arg Pro Glu Leu Lys Phe Ser Asp Val Ser Glu Glu
1               5                   10                  15

Arg Asn Phe Tyr Lys Lys Tyr Thr Gly Leu Pro Lys Lys Pro Leu Lys
                20                  25                  30

Thr Ile Arg Leu Val Asp Lys Gly Asp Tyr Tyr Thr Val Ile Gly Ser
            35                  40                  45

Asp Ala Ile Phe Val Ala Asp Ser Val Tyr His Thr Gln Ser Val Leu
        50                  55                  60

Lys Asn Cys Gln Leu Asp Pro Val Thr Ala Lys Asn Phe His Glu Pro
65                  70                  75                  80

Thr Lys Tyr Val Thr Val Ser Leu Gln Val Leu Ala Thr Leu Leu Lys
                85                  90                  95

Leu Cys Leu Leu Asp Leu Gly Tyr Lys Val Glu Ile Tyr Asp Lys Gly
                100                 105                 110

Trp Lys Leu Ile Lys Ser Ala Ser Pro Gly Asn Ile Glu Gln Val Asn
            115                 120                 125
```

```
Glu Leu Met Asn Met Asn Ile Asp Ser Ser Ile Ile Ile Ala Ser Leu
    130                 135                 140

Lys Val Gln Trp Asn Ser Gln Asp Gly Asn Cys Ile Ile Gly Val Ala
145                 150                 155                 160

Phe Ile Asp Thr Thr Ala Tyr Lys Val Gly Met Leu Asp Ile Val Asp
                165                 170                 175

Asn Glu Val Tyr Ser Asn Leu Glu Ser Phe Leu Ile Gln Leu Gly Val
            180                 185                 190

Lys Glu Cys Leu Val Gln Asp Leu Thr Ser Asn Ser Asn Ser Asn Ala
        195                 200                 205

Glu Met Gln Lys Val Ile Asn Val Ile Asp Arg Cys Gly Cys Val Val
    210                 215                 220

Thr Leu Lys Asn Ser Glu Phe Ser Glu Lys Asp Val Glu Leu Asp
225                 230                 235                 240

Leu Thr Lys Leu Leu Gly Asp Asp Leu Ala Leu Ser Leu Pro Gln Lys
                245                 250                 255

Tyr Ser Lys Leu Ser Met Gly Ala Cys Asn Ala Leu Ile Gly Tyr Leu
            260                 265                 270

Gln Leu Leu Ser Glu Gln Asp Gln Val Gly Lys Tyr Glu Leu Val Glu
        275                 280                 285

His Lys Leu Lys Glu Phe Met Lys Leu Asp Ala Ser Ala Ile Lys Ala
    290                 295                 300

Leu Asn Leu Phe Pro Gln Gly Pro Gln Asn Pro Phe Gly Ser Asn Asn
305                 310                 315                 320

Leu Ala Val Ser Gly Phe Thr Ser Ala Gly Asn Ser Gly Lys Val Thr
                325                 330                 335

Ser Leu Phe Gln Leu Leu Asn His Cys Lys Thr Asn Ala Gly Val Arg
            340                 345                 350

Leu Leu Asn Glu Trp Leu Lys Gln Pro Leu Thr Asn Ile Asp Glu Ile
        355                 360                 365

Asn Lys Arg His Asp Leu Val Asp Tyr Leu Ile Asp Gln Ile Glu Leu
    370                 375                 380

Arg Gln Met Leu Thr Ser Glu Tyr Leu Pro Met Ile Pro Asp Ile Arg
385                 390                 395                 400

Arg Leu Thr Lys Lys Leu Asn Lys Arg Gly Asn Leu Glu Asp Val Leu
                405                 410                 415

Lys Ile Tyr Gln Phe Ser Lys Arg Ile Pro Glu Ile Val Gln Val Phe
            420                 425                 430

Thr Ser Phe Leu Glu Asp Asp Ser Pro Thr Glu Pro Val Asn Glu Leu
        435                 440                 445

Val Arg Ser Val Trp Leu Ala Pro Leu Ser His Val Glu Pro Leu
450                 455                 460

Ser Lys Phe Glu Glu Met Val Glu Thr Thr Val Asp Leu Asp Ala Tyr
465                 470                 475                 480

Glu Glu Asn Asn Glu Phe Met Ile Lys Val Glu Phe Asn Glu Glu Leu
                485                 490                 495

Gly Lys Ile Arg Ser Lys Leu Asp Thr Leu Arg Asp Glu Ile His Ser
            500                 505                 510

Ile His Leu Asp Ser Ala Glu Asp Leu Gly Phe Asp Pro Asp Lys Lys
        515                 520                 525

Leu Lys Leu Glu Asn His His Leu His Gly Trp Cys Met Arg Leu Thr
530                 535                 540

Arg Asn Asp Ala Lys Glu Leu Arg Lys His Lys Lys Tyr Ile Glu Leu
```

```
                545                 550                 555                 560
Ser Thr Val Lys Ala Gly Ile Phe Phe Ser Thr Lys Gln Leu Lys Ser
                565                 570                 575

Ile Ala Asn Glu Thr Asn Ile Leu Gln Lys Glu Tyr Asp Lys Gln Gln
                580                 585                 590

Ser Ala Leu Val Arg Glu Ile Asn Ile Thr Leu Thr Tyr Thr Pro
                595                 600                 605

Val Phe Glu Lys Leu Ser Leu Val Leu Ala His Leu Asp Val Ile Ala
                610                 615                 620

Ser Phe Ala His Thr Ser Ser Tyr Ala Pro Ile Pro Tyr Ile Arg Pro
625                 630                 635                 640

Lys Leu His Pro Met Asp Ser Glu Arg Arg Thr His Leu Ile Ser Ser
                645                 650                 655

Arg His Pro Val Leu Glu Met Gln Asp Asp Ile Ser Phe Ile Ser Asn
                660                 665                 670

Asp Val Thr Leu Glu Ser Gly Lys Gly Asp Phe Leu Ile Ile Thr Gly
                675                 680                 685

Pro Asn Met Gly Gly Lys Ser Thr Tyr Ile Arg Gln Val Gly Val Ile
                690                 695                 700

Ser Leu Met Ala Gln Ile Gly Cys Phe Val Pro Cys Glu Glu Ala Glu
705                 710                 715                 720

Ile Ala Ile Val Asp Ala Ile Leu Cys Arg Val Gly Ala Gly Asp Ser
                725                 730                 735

Gln Leu Lys Gly Val Ser Thr Phe Met Val Glu Ile Leu Glu Thr Ala
                740                 745                 750

Ser Ile Leu Lys Asn Ala Ser Lys Asn Ser Leu Ile Ile Val Asp Glu
                755                 760                 765

Leu Gly Arg Gly Thr Ser Thr Tyr Asp Gly Phe Gly Leu Ala Trp Ala
                770                 775                 780

Ile Ala Glu His Ile Ala Ser Lys Ile Gly Cys Phe Ala Leu Phe Ala
785                 790                 795                 800

Thr His Phe His Glu Leu Thr Glu Leu Ser Glu Lys Leu Pro Asn Val
                805                 810                 815

Lys Asn Met His Val Val Ala His Ile Glu Lys Asn Leu Lys Glu Gln
                820                 825                 830

Lys His Asp Asp Glu Asp Ile Thr Leu Leu Tyr Lys Val Glu Pro Gly
                835                 840                 845

Ile Ser Asp Gln Ser Phe Gly Ile His Val Ala Glu Val Val Gln Phe
                850                 855                 860

Pro Glu Lys Ile Val Lys Met Ala Lys Arg Lys Ala Asn Glu Leu Asp
865                 870                 875                 880

Asp Leu Lys Thr Asn Asn Glu Asp Leu Lys Lys Ala Lys Leu Ser Leu
                885                 890                 895

Gln Glu Val Asn Glu Gly Asn Ile Arg Leu Lys Ala Leu Leu Lys Glu
                900                 905                 910

Trp Ile Arg Lys Val Lys Glu Glu Gly Leu His Asp Pro Ser Lys Ile
                915                 920                 925

Thr Glu Glu Ala Ser Gln His Lys Ile Gln Glu Leu Leu Arg Ala Ile
                930                 935                 940

Ala Asn Glu Pro Glu Lys Glu Asn Asp Asn Tyr Leu Glu Ile Tyr Lys
945                 950                 955                 960

Ser Pro Cys Cys Tyr Asn
                965
```

(2) INFORMATION FOR SEQ ID NO:4:

(i) SEQUENCE CHARACTERISTICS:
    (A) LENGTH: 959 amino acids
    (B) TYPE: amino acid
    (D) TOPOLOGY: linear (ii) MOLECULE TYPE: protein (iii) HYPOTHETICAL: NO (vi) ORIGINAL SOURCE:
    (A) ORGANISM: Saccharomyces cerevisiae (vii) IMMEDIATE SOURCE:
    (B) CLONE: Msh1

(xi) SEQUENCE DESCRIPTION: SEQ ID NO:4:

```
Met Lys His Phe Phe Arg Leu Pro Thr Ala Phe Arg Pro Ile Ser Arg
1               5                   10                  15

Val Ser Leu Arg Tyr Ser Ser Thr Asp Thr Ala Gln Pro Lys Ile Ser
            20                  25                  30

Lys Leu Lys Ile Ser Phe Asn Lys Ile Ser Glu Ser Asn Ser Glu Lys
        35                  40                  45

Lys Asp Asn Leu Gly Ser Ile Asp Thr Arg Asn Cys Leu Ser Thr Gln
50                  55                  60

Gln Asp Asp Lys Leu Ser Ser Thr Glu Pro Ser Lys Ala Ser Leu Pro
65                  70                  75                  80

Pro Ser Leu Gln Tyr Val Arg Asp Leu Met Asp Leu Tyr Lys Asp His
            85                  90                  95

Val Val Leu Thr Gln Met Gly Ser Phe Tyr Glu Leu Tyr Phe Glu Gln
            100                 105                 110

Ala Ile Arg Tyr Ala Pro Glu Leu Asn Ile Ser Leu Thr Asn Arg Ala
        115                 120                 125

Tyr Ser His Gly Lys Val Pro Phe Ala Gly Phe Pro Val His Gln Leu
130                 135                 140

Ser Arg His Leu Lys Met Leu Val Asn Asn Cys Gly Tyr Ser Val Thr
145                 150                 155                 160

Ile Ala Glu Gln Phe Lys Lys Lys Asp Val Ala Asp Asn Glu Ala Asn
                165                 170                 175

Lys Phe Tyr Arg Arg Val Thr Arg Ile Val Thr Pro Gly Thr Phe Ile
            180                 185                 190

Asp Glu Ala Phe Glu Asn Leu Arg Glu Asn Thr Tyr Leu Leu Asn Ile
        195                 200                 205

Glu Phe Pro Glu Asn Cys Met Ser Gln Val Ala Asp Thr Ser Leu Lys
210                 215                 220

Val Gly Ile Cys Trp Cys Asp Val Ser Thr Gly Glu Ile Phe Val Gln
225                 230                 235                 240

Gln Val Tyr Leu Arg Asp Leu Val Ser Ala Ile Thr Arg Ile Gln Pro
                245                 250                 255

Lys Glu Ile Leu Leu Asp Glu Arg Leu Leu Glu Phe His Ile Glu Ser
            260                 265                 270

Gly Thr Trp Tyr Pro Glu Leu Val Glu Leu Lys Lys Phe Phe Ile Lys
        275                 280                 285

Tyr Gln Lys Met Pro Ser Gln His Arg Thr Ile Glu Ser Phe Tyr Gly
290                 295                 300

Leu Phe Asn Leu Gly Gly Lys Glu Ala Thr Glu Arg Gln Leu Lys Ile
```

-continued

```
            305                 310                 315                 320
Gln Phe Gln Thr Phe Thr Gln Lys Glu Leu Ala Ala Leu Arg Asn Thr
                325                 330                 335

Leu Ile Tyr Val Ser Asn His Leu Pro Asp Phe Ser Ile Asn Phe Gln
                340                 345                 350

Ile Pro Gln Arg Gln Leu Ala Thr Ala Ile Met Gln Ile Asp Ser Arg
                355                 360                 365

Thr Ser Thr Ala Leu Glu Leu His Ser Thr Val Arg Asp Asn Asn Lys
                370                 375                 380

Lys Gly Ser Leu Leu Ser Ser Ile Arg Arg Thr Val Thr Pro Ser Gly
385                 390                 395                 400

Thr Arg Leu Leu Ser Gln Trp Leu Ser Gly Pro Ser Leu Asp Leu Lys
                405                 410                 415

Glu Ile Lys Lys Arg Gln Lys Ile Val Ala Phe Phe Lys Asp Asn Arg
                420                 425                 430

Asp Ile Thr Glu Asn Leu Arg Thr Met Leu Lys Lys Val Asn Asp Leu
                435                 440                 445

Ser Arg Ile Leu Gln Lys Phe Ser Phe Gly Arg Gly Glu Ala Leu Glu
                450                 455                 460

Leu Ile Gln Met Ala Arg Ser Leu Glu Val Ser Arg Glu Ile Arg Lys
465                 470                 475                 480

Tyr Leu Leu Asn Asn Thr Ser Leu Met Lys Ala Thr Leu Lys Ser Gln
                485                 490                 495

Ile Thr Gln Leu Thr Glu Ser Leu Asn Phe Glu Lys Asn Leu Ile Asp
                500                 505                 510

Asp Ile Leu Lys Phe Leu Asn Glu Glu Glu Leu Ala Lys Ser Gln Asp
                515                 520                 525

Ala Lys Gln Asn Ala Asp Val Thr Arg Met Leu Asp Ile Asp Val Lys
                530                 535                 540

Asp Lys Lys Glu Ser Asn Lys Asp Glu Ile Phe Glu Leu Arg Asp Phe
545                 550                 555                 560

Ile Val Asn Pro Ser Phe Asn Thr Lys Leu Arg Lys Leu His Asp Thr
                565                 570                 575

Tyr Gln Gly Val Trp Gln Lys Lys Thr Glu Tyr Asn Ala Leu Leu Lys
                580                 585                 590

Gly Phe Phe Val Gly Asp Leu Gly Ala Lys Thr Phe Thr Leu Lys Glu
                595                 600                 605

Arg Gln Asn Gly Glu Tyr Ala Leu His Val Thr Gly Thr Ala Ser Ser
                610                 615                 620

Leu Lys Lys Ile Asp Glu Leu Ile Ser Lys Ser Thr Glu Tyr His Gly
625                 630                 635                 640

Ser Cys Phe His Ile Leu Gln Lys Ser Ser Gln Thr Arg Trp Leu Ser
                645                 650                 655

His Lys Ile Trp Thr Asp Leu Gly His Glu Leu Glu Leu Leu Asn Leu
                660                 665                 670

Lys Ile Arg Asn Glu Glu Ala Asn Ile Ile Asp Leu Phe Lys Arg Lys
                675                 680                 685

Phe Ile Asp Arg Ser Asn Val Val Arg Gln Val Ala Thr Thr Leu Gly
                690                 695                 700

Tyr Leu Asp Thr Leu Ser Ser Phe Ala Val Leu Ala Asn Glu Arg Asn
705                 710                 715                 720

Leu Val Cys Pro Lys Val Asp Glu Ser Asn Lys Leu Glu Val Val Asn
                725                 730                 735
```

-continued

```
Gly Arg His Leu Met Val Glu Glu Gly Leu Ser Ala Arg Ser Leu Glu
            740                 745                 750
Thr Phe Thr Ala Asn Asn Cys Glu Leu Ala Lys Asp Asn Leu Trp Val
            755                 760                 765
Ile Thr Gly Pro Asn Met Gly Gly Lys Ser Thr Phe Leu Arg Gln Asn
            770                 775                 780
Ala Ile Ile Val Ile Leu Ala Gln Ile Gly Cys Phe Val Pro Cys Ser
785                 790                 795                 800
Lys Ala Arg Val Gly Ile Val Asp Lys Leu Phe Ser Arg Val Gly Ser
            805                 810                 815
Ala Asp Asp Leu Tyr Asn Glu Met Ser Thr Phe Met Val Glu Met Ile
            820                 825                 830
Glu Thr Ser Phe Ile Leu Gln Gly Ala Thr Glu Arg Ser Leu Ala Ile
            835                 840                 845
Leu Asp Glu Ile Gly Arg Gly Thr Ser Gly Lys Glu Gly Ile Ser Ile
            850                 855                 860
Ala Tyr Ala Thr Leu Lys Tyr Leu Leu Glu Asn Asn Gln Cys Arg Thr
865                 870                 875                 880
Leu Phe Ala Thr His Phe Gly Gln Glu Leu Lys Gln Ile Ile Asp Asn
            885                 890                 895
Lys Cys Ser Lys Gly Met Ser Glu Lys Val Lys Phe Tyr Gln Ser Gly
            900                 905                 910
Ile Thr Asp Leu Gly Gly Asn Asn Phe Cys Tyr Asn His Lys Leu Lys
            915                 920                 925
Pro Gly Ile Cys Thr Lys Ser Asp Ala Ile Arg Val Ala Glu Leu Ala
            930                 935                 940
Gly Phe Pro Met Glu Ala Leu Lys Glu Ala Arg Glu Ile Leu Gly
945                 950                 955
```

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:5:

```
Thr Gly Pro Asn Met
1               5
```

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:6:

Phe Ala Thr His Phe

```
1               5

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:7:

Phe Ala Thr His Tyr
1               5

(2) INFORMATION FOR SEQ ID NO:8:

(i) SEQUENCE CHARACTERISTICS:
        (A) LENGTH: 3110 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (vii) IMMEDIATE SOURCE:
        (B) CLONE: hMSH2

(xi) SEQUENCE DESCRIPTION: SEQ ID NO:8:

ATTCGGCACG AGGACATGGC GGTGCAGCCG AAGGAGACGC TGCAGTTGGA GAGCGCGGCC        60

GAGGTCGGCT TCGTGCGCTT CTTTCAGGGC ATGCCGGAGA AGCCGACCAC CACAGTGCGC       120

CTTTTCGACC GGGGCGACTT CTATACGGCG CACGGCGAGG ACGCGCTGCT GGCCGCCCGG       180

GAGGTGTTCA AGACCCAGGG GGTGATCAAG TACATGGGGC CGGCAGGAGC AAAGAATCTG       240

CAGAGTGTTG TGCTTAGTAA AATGAATTTT GAATCTTTTG TAAAAGATCT TCTTCTGGTT       300

CGTCAGTATA GAGTTGAAGT TTATAAGAAT AGAGCTGGAA ATAAGGCATC CAAGGAGAAT       360

GATTGGTATT TGGCATATAA GGCTTCTCCT GGCAATCTCT CTCAGTTTGA AGATATTCTC       420

TTTGGTAACA ATGATATGTC AGCTTCCATT GGTGTTGTGG GTGTTAAAAT GTCCGCAGTT       480

GATGGCCAGA GACAGGTTGG AGTTGGGTAT GTGGATTCCA TACAGAGGAA ACTAGGACTG       540

TGTGAATTCC CTGATAATGA TCAGTTCTCC AATCTTGAGG CTCTCCTCAT CCAGATTGGA       600

CCAAAGGAAT GTGTTTTACC CGGAGGAGAG ACTGCTGGAG ACATGGGGAA ACTGAGACAG       660

ATAATTCAAA GAGGAGGAAT TCTGATCACA GAAAGAAAAA AAGCTGACTT TTCCACAAAA       720

GACATTTATC AGGACCTCAA CCGGTTGTTG AAAGGCAAAA AGGGAGAGCA GATGAATAGT       780

GCTGTATTGC AGAAATGGA GAATCAGGTT GCAGTTTCAT CACTGTCTGC GGTAATCAAG       840

TTTTTAGAAC TCTTATCAGA TGATTCCAAC TTTGGACAGT TGAACTGAC TACTTTTGAC       900

TTCAGCCAGT ATATGAAATT GGATATTGCA GCAGTCAGAG CCCTTAACCT TTTTCAGGGT       960

TCTGTTGTAG ATACCACTGG CTCTCAGTCT CTGGCTGCCT TGCTGAATAA GTGTAAAACC      1020

CCTCAAGGAC AAAGACTTGT TAACCAGTGG ATTAAGCAGC CTCTCATGGA TAAGAACAGA      1080
```

```
ATAGAGGAGA GATTGAATTT AGTGGAAGCT TTTGTAGAAG ATGCAGAATT GAGGCAGACT    1140

TTACAAGAAG ATTTACTTCG TCGATTCCCA GATCTTAACC GACTTGCCAA GAAGTTTCAA    1200

AGACAAGCAG CAAACTTACA AGATTGTTAC CGACTCTATC AGGGTATAAA TCAACTACCT    1260

AATGTTATAC AGGCTCTGGA AAAACATGAA GGAAACACC AGAAATTATT GTTGGCAGTT     1320

TTTGTGACTC CTCTTACTGA TCTTCGTTCT GACTTCTCCA AGTTTCAGGA AATGATAGAA    1380

ACAACTTTAG ATATGGATCA GGTGGAAAAC CATGAATTCC TTGTAAAACC TTCATTTGAT    1440

CCTAATCTCA GTGAATTAAG AGAAATAATG AATGACTTGG AAAAGAAGAT GCAGTCAACA    1500

TTAATAAGTG CAGCCAGAGA TCTTGGCTTG GACCCTGGCA AACAGATTAA ACTGGATTCC    1560

AGTGCACAGT TTGGATATTA CTTTCGTGTA ACCTGTAAGG AAGAAAAAGT CCTTCGTAAC    1620

AATAAAAACT TTAGTACTGT AGATATCCAG AAGAATGGTG TTAAATTTAC CAACAGCAAA    1680

TTGACTTCTT TAAATGAAGA GTATACCAAA AATAAAACAG AATATGAAGA AGCCCAGGAT    1740

GCCATTGTTA AAGAAATTGT CAATATTTCT TCAGGCTATG TAGAACCAAT GCAGACACTC    1800

AATGATGTGT TAGCTCAGCT AGATGCTGTT GTCAGCTTTG CTCACGTGTC AAATGGAGCA    1860

CCTGTTCCAT ATGTACGACC AGCCATTTTG GAGAAAGGAC AAGGAAGAAT TATATTAAAA    1920

GCATCCAGGC ATGCTTGTGT TGAAGTTCAA GATGAAATTG CATTTATTCC TAATGACGTA    1980

TACTTTGAAA AAGATAAACA GATGTTCCAC ATCATTACTG GCCCCAATAT GGGAGGTAAA    2040

TCAACATATA TTCGACAAAC TGGGGTGATA GTACTCATGG CCCAAATTGG GTGTTTTGTG    2100

CCATGTGAGT CAGCAGAAGT GTCCATTGTG GACTGCATCT TAGCCCGAGT AGGGGCTGGT    2160

GACAGTCAAT TGAAAGGAGT CTCCACGTTC ATGGCTGAAA TGTTGGAAAC TGCTTCTATC    2220

CTCAGGTCTG CAACCAAAGA TTCATTAATA ATCATAGATG AATTGGGAAG AGGAACTTCT    2280

ACCTACGATG GATTTGGGTT AGCATGGGCT ATATCAGAAT ACATTGCAAC AAAGATTGGT    2340

GCTTTTTGCA TGTTTGCAAC CCATTTTCAT GAACTTACTG CCTTGGCCAA TCAGATACCA    2400

ACTGTTAATA ATCTACATGT CACAGCACTC ACCACTGAAG AGACCTTAAC TATGCTTTAT    2460

CAGGTGAAGA AAGGTGTCTG TGATCAAAGT TTTGGGATTC ATGTTGCAGA GCTTGCTAAT    2520

TTCCCTAAGC ATGTAATAGA GTGTGCTAAA CAGAAAGCCC TGGAACTTGA GGAGTTTCAG    2580

TATATTGGAG AATCGCAAGG ATATGATATC ATGGAACCAG CAGCAAAGAA GTGCTATCTG    2640

GAAAGAGAGC AAGGTGAAAA AATTATTCAG GAGTTCCTGT CCAAGGTGAA ACAAATGCCC    2700

TTTACTGAAA TGTCAGAAGA AAACATCACA ATAAAGTTAA AACAGCTAAA AGCTGAAGTA    2760

ATAGCAAAGA ATAATAGCTT TGTAAATGAA ATCATTTCAC GAATAAAAGT TACTACGTGA    2820

AAAATCCCAG TAATGGAATG AAGGTAATAT TGATAAGCTA TTGTCTGTAA TAGTTTTATA    2880

TTGTTTTATA TTAACCCTTT TTCCATAGTG TTAACTGTCA GTGCCCATGG CTATCAACT     2940

TAATAAGATA TTTAGTAATA TTTTACTTTG AGGACATTTT CAAAGATTTT TATTTTGAAA    3000

AATGAGAGCT GTAACTGAGG ACTGTTTGCA ATTGACATAG GCAATAATAA GTGATGTGCT    3060

GAATTTTTAT AAAAAATCAT GAGTTTGGGA AAAAAAAAA AAAAAAAAA                 3110
```

(2) INFORMATION FOR SEQ ID NO:10:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
            (B) CLONE: mMSH2 fragment (xi) SEQUENCE DESCRIPTION: SEQ ID NO:10:

CTTAATAATC ATTGATGAGC TGGGAAGAGG AACCTCTACC TATGATGGAT TTGGGTTAGC    60

ATGGGCTATA TCAGATTACA TT    82

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

CTGGATCCRT GNGTNRCRAA    20

(2) INFORMATION FOR SEQ ID NO:12:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

CTGGATCCAC NGGNCCNAAY ATG    23

(2) INFORMATION FOR SEQ ID NO:13:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

CGCGGATCCR WARTGNGTNG CRAA    24

(2) INFORMATION FOR SEQ ID NO:14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

CGCGGATCCR WARTGNGTNG TRAA                                                   24

(2) INFORMATION FOR SEQ ID NO:15:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (vii) IMMEDIATE SOURCE:
        (B) CLONE: PCR clone 22.1

(xi) SEQUENCE DESCRIPTION: SEQ ID NO:15:

GGAGGTAAAT CAACATATAT TCGACAAACT GGGGTGATAG TACTCATGGC CCAAATTGGG            60

TGTTTTGTGC CATGTGAGTC AGCAGAAGTG TCCATTGTGG ACTGCATCTT AGCCCGAGTA          120

GGGGCTGGTG ACAGTCAATT GAAAGGAGTC TCCACGTTCA TGGCTGAAAT GTTGGAAACT          180

GCTTCTATCC TCAGGTCTGC AACCAAAGAT TCATTAATAA TCATAGATGA ATTGGGAAGA          240

GGAACTTCTA CCTACGATGG ATTTGGGTTA GCATGGGCTA TATCAGAATA CATTGCAACA          300

AAGATTGGTG CTTTTTGCAT G                                                   321

(2) INFORMATION FOR SEQ ID NO:16:

(i) SEQUENCE CHARACTERISTICS:
        (A) LENGTH: 934 amino acids
        (B) TYPE: amino acid
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (B) CLONE: hMsh2

(xi) SEQUENCE DESCRIPTION: SEQ ID NO:16:

Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

```
Ser Lys Met Asn Phe Glu Ser Phe Val Lys Asp Leu Leu Val Arg
            85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
            115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Gly Glu Gln Met Asn Ser Ala
            245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Val Asp Thr
305                 310                 315                 320

Thr Gly Ser Gln Ser Leu Ala Ala Leu Leu Asn Lys Cys Lys Thr Pro
            325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
        355                 360                 365

Asp Ala Glu Leu Arg Gln Thr Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
            405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
        435                 440                 445

Lys Phe Gln Glu Met Ile Glu Thr Thr Leu Asp Met Asp Gln Val Glu
    450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
            485                 490                 495

Ile Ser Ala Ala Arg Asp Leu Gly Leu Asp Pro Gly Lys Gln Ile Lys
```

-continued

```
                500                 505                 510
Leu Asp Ser Ser Ala Gln Phe Gly Tyr Tyr Phe Arg Val Thr Cys Lys
            515                 520                 525
Glu Glu Lys Val Leu Arg Asn Asn Lys Asn Phe Ser Thr Val Asp Ile
        530                 535                 540
Gln Lys Asn Gly Val Lys Phe Thr Asn Ser Lys Leu Thr Ser Leu Asn
545                 550                 555                 560
Glu Glu Tyr Thr Lys Asn Lys Thr Glu Tyr Glu Ala Gln Asp Ala
            565                 570                 575
Ile Val Lys Glu Ile Val Asn Ile Ser Ser Gly Tyr Val Glu Pro Met
            580                 585                 590
Gln Thr Leu Asn Asp Val Leu Ala Gln Leu Asp Ala Val Val Ser Phe
            595                 600                 605
Ala His Val Ser Asn Gly Ala Pro Val Pro Tyr Val Arg Pro Ala Ile
            610                 615                 620
Leu Glu Lys Gly Gln Gly Arg Ile Ile Leu Lys Ala Ser Arg His Ala
625                 630                 635                 640
Cys Val Glu Val Gln Asp Glu Ile Ala Phe Ile Pro Asn Asp Val Tyr
                645                 650                 655
Phe Glu Lys Asp Lys Gln Met Phe His Ile Ile Thr Gly Pro Asn Met
                660                 665                 670
Gly Gly Lys Ser Thr Tyr Ile Arg Gln Thr Gly Val Ile Val Leu Met
            675                 680                 685
Ala Gln Ile Gly Cys Phe Val Pro Cys Glu Ser Ala Glu Val Ser Ile
            690                 695                 700
Val Asp Cys Ile Leu Ala Arg Val Gly Ala Gly Asp Ser Gln Leu Lys
705                 710                 715                 720
Gly Val Ser Thr Phe Met Ala Glu Met Leu Glu Thr Ala Ser Ile Leu
                725                 730                 735
Arg Ser Ala Thr Lys Asp Ser Leu Ile Ile Ile Asp Glu Leu Gly Arg
                740                 745                 750
Gly Thr Ser Thr Tyr Asp Gly Phe Gly Leu Ala Trp Ala Ile Ser Glu
                755                 760                 765
Tyr Ile Ala Thr Lys Ile Gly Ala Phe Cys Met Phe Ala Thr His Phe
770                 775                 780
His Glu Leu Thr Ala Leu Ala Asn Gln Ile Pro Thr Val Asn Asn Leu
785                 790                 795                 800
His Val Thr Ala Leu Thr Thr Glu Glu Thr Leu Thr Met Leu Tyr Gln
                805                 810                 815
Val Lys Lys Gly Val Cys Asp Gln Ser Phe Gly Ile His Val Ala Glu
                820                 825                 830
Leu Ala Asn Phe Pro Lys His Val Ile Glu Cys Ala Lys Gln Lys Ala
            835                 840                 845
Leu Glu Leu Glu Glu Phe Gln Tyr Ile Gly Glu Ser Gln Gly Tyr Asp
            850                 855                 860
Ile Met Glu Pro Ala Ala Lys Lys Cys Tyr Leu Glu Arg Glu Gln Gly
865                 870                 875                 880
Glu Lys Ile Ile Gln Glu Phe Leu Ser Lys Val Lys Gln Met Pro Phe
                885                 890                 895
Thr Glu Met Ser Glu Glu Asn Ile Thr Ile Lys Leu Lys Gln Leu Lys
                900                 905                 910
Ala Glu Val Ile Ala Lys Asn Asn Ser Phe Val Asn Glu Ile Ile Ser
            915                 920                 925
```

Arg Ile Lys Val Thr Thr
    930

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

CGCGGATCCA GCACCAATCT TTGTTGC                                               27

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

CGCGGATCCG GTCTGCAACC AAAGATTC                                              28

(2) INFORMATION FOR SEQ ID NO:19:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Saccharomyces cerevisiae (vii) IMMEDIATE SOURCE:
        (B) CLONE: PCR clone ms351-I (xi) SEQUENCE DESCRIPTION: SEQ ID NO:19:

GGTGGTAAAT CTACATTCTT AAGACAGAAT GCAATTATAG TCATTCTGGC GCAAATTGGA            60

TGTTTTGTTC CATGCAGTAA GGCGCGTGTG GGTATTGTAG ATAAGCTTTT TAGCCGAGTT           120

GGTTCAGCAG ATGATCTGTA CAATGAGATG AGTACGTTCA TGGTTGAGAT GATAGAAACG           180

TCGTTCATCT TGCAAGGAGC TACGGAACGG TCTTTAGCTA TTCTAGATGA GATTGGCCGA           240

GGGACTAGTG GTAAAGAAGG CATTAGCATC GCTTATGCAA CTTTAAAGTA TTTGTTAGAG           300

AACAATCAAT GCAGAACGCT T                                                    321

(2) INFORMATION FOR SEQ ID NO:20:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Saccharomyces cerevisiae (vii) IMMEDIATE SOURCE:
        (B) CLONE: PCR clone ms351-II (xi) SEQUENCE DESCRIPTION: SEQ ID NO:20:

GGAGGTAAAT CTACTTACAT CAGACAGGTT GGTGTGATTT CTTTAATGGC CCAAATTGGT      60

TGTTTCGTAC CTTGTGAAGA AGCTGAAATA GCCATAGTAG ATGCAATTCT TTGCAGGGTC     120

GGGGCAGGAG ATTCCCAATT GAAAGGTGTT TCCACATTTA TGGTTGAAAT ATTGGAAACT     180

GCTTCTATAC TAAAGAATGC GAGTAAGAAT TCTTTGATTA TTGTAGATGA ACTAGGGCGT     240

GGTACTAGTA CATATGATGG TTTTGGTCTA GCTTGGGCAA TTGCTGAACA TATCGCAAGT     300

AAGATTGGAT GTTTCGCTTT G                                              321

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

GTTTTTCCTT TCATCCGTTG                                                  20

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

AAACTAGCCA GGTATGG                                                     17

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

GTGATAGTAC TCATGGCC                                                         18

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16337

(xi) SEQUENCE DESCRIPTION: SEQ ID NO:25:

CATGTTAGAG CATTTAGGG                                                        19

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16338

(xi) SEQUENCE DESCRIPTION: SEQ ID NO:26:

GGTAGTAGGT ATTTATGGAA TAC                                                   23

(2) INFORMATION FOR SEQ ID NO:27:

(i) SEQUENCE CHARACTERISTICS:
        (A) LENGTH: 971 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:27:

Met Lys His Phe Phe Arg Leu Pro Thr Ala Phe Arg Pro Ile Ser Arg
1               5                   10                  15

Val Ser Leu Arg Tyr Ser Ser Thr Tyr Pro Tyr Asp Val Pro Asp Tyr
                20                  25                  30

Ala Ser Ser Thr Asp Thr Ala Gln Pro Lys Ile Ser Lys Leu Lys Ile
            35                  40                  45

Ser Phe Asn Lys Ile Ser Glu Ser Asn Ser Glu Lys Lys Asp Asn Leu

```
                50                  55                  60
Gly Ser Ile Asp Thr Arg Asn Cys Leu Ser Thr Gln Gln Asp Asp Lys
 65                  70                  75                  80

Leu Ser Ser Thr Glu Pro Ser Lys Ala Ser Leu Pro Pro Ser Leu Gln
                 85                  90                  95

Tyr Val Arg Asp Leu Met Asp Leu Tyr Lys Asp His Val Val Leu Thr
                100                 105                 110

Gln Met Gly Ser Phe Tyr Glu Leu Tyr Phe Glu Gln Ala Ile Arg Tyr
                115                 120                 125

Ala Pro Glu Leu Asn Ile Ser Leu Thr Asn Arg Ala Tyr Ser His Gly
130                 135                 140

Lys Val Pro Phe Ala Gly Phe Pro Val His Gln Leu Ser Arg His Leu
145                 150                 155                 160

Lys Met Leu Val Asn Asn Cys Gly Tyr Ser Val Thr Ile Ala Glu Gln
                165                 170                 175

Phe Lys Lys Lys Asp Val Ala Asp Asn Glu Ala Asn Lys Phe Tyr Arg
                180                 185                 190

Arg Val Thr Arg Ile Val Thr Pro Gly Thr Phe Ile Asp Glu Ala Phe
                195                 200                 205

Glu Asn Leu Arg Glu Asn Thr Tyr Leu Leu Asn Ile Glu Phe Pro Glu
210                 215                 220

Asn Cys Met Ser Gln Val Ala Asp Thr Ser Leu Lys Val Gly Ile Cys
225                 230                 235                 240

Trp Cys Asp Val Ser Thr Gly Glu Ile Phe Val Gln Gln Val Tyr Leu
                245                 250                 255

Arg Asp Leu Val Ser Ala Ile Thr Arg Ile Gln Pro Lys Glu Ile Leu
                260                 265                 270

Leu Asp Glu Arg Leu Leu Glu Phe His Ile Glu Ser Gly Thr Trp Tyr
                275                 280                 285

Pro Glu Leu Val Glu Leu Lys Phe Ile Lys Tyr Gln Lys Met
                290                 295                 300

Pro Ser Gln His Arg Thr Ile Glu Ser Phe Tyr Gly Leu Phe Asn Leu
305                 310                 315                 320

Gly Gly Lys Glu Ala Thr Glu Arg Gln Leu Lys Ile Gln Phe Gln Thr
                325                 330                 335

Phe Thr Gln Lys Glu Leu Ala Ala Leu Arg Asn Thr Leu Ile Tyr Val
                340                 345                 350

Ser Asn His Leu Pro Asp Phe Ser Ile Asn Phe Gln Ile Pro Gln Arg
                355                 360                 365

Gln Leu Ala Thr Ala Ile Met Gln Ile Asp Ser Arg Thr Ser Thr Ala
370                 375                 380

Leu Glu Leu His Ser Thr Val Arg Asp Asn Lys Lys Gly Ser Leu
385                 390                 395                 400

Leu Ser Ser Ile Arg Arg Thr Val Thr Pro Ser Gly Thr Arg Leu Leu
                405                 410                 415

Ser Gln Trp Leu Ser Gly Pro Ser Leu Asp Leu Lys Glu Ile Lys Lys
                420                 425                 430

Arg Gln Lys Ile Val Ala Phe Phe Lys Asp Asn Arg Asp Ile Thr Glu
                435                 440                 445

Asn Leu Arg Thr Met Leu Lys Lys Val Asn Asp Leu Ser Arg Ile Leu
450                 455                 460

Gln Lys Phe Ser Phe Gly Arg Gly Glu Ala Leu Glu Leu Ile Gln Met
465                 470                 475                 480
```

-continued

```
Ala Arg Ser Leu Glu Val Ser Arg Glu Ile Arg Lys Tyr Leu Leu Asn
                485                 490                 495

Asn Thr Ser Leu Met Lys Ala Thr Leu Lys Ser Gln Ile Thr Gln Leu
                500                 505                 510

Thr Glu Ser Leu Asn Phe Glu Lys Asn Leu Ile Asp Ile Leu Lys
                515                 520                 525

Phe Leu Asn Glu Glu Leu Ala Lys Ser Gln Asp Ala Lys Gln Asn
                530                 535                 540

Ala Asp Val Thr Arg Met Leu Asp Ile Asp Val Lys Asp Lys Glu
545                 550                 555                 560

Ser Asn Lys Asp Glu Ile Phe Glu Leu Arg Asp Phe Ile Val Asn Pro
                565                 570                 575

Ser Phe Asn Thr Lys Leu Arg Lys Leu His Asp Thr Tyr Gln Gly Val
                580                 585                 590

Trp Gln Lys Lys Thr Glu Tyr Asn Ala Leu Leu Lys Gly Phe Phe Val
                595                 600                 605

Gly Asp Leu Gly Ala Lys Thr Phe Thr Leu Lys Glu Arg Gln Asn Gly
                610                 615                 620

Glu Tyr Ala Leu His Val Thr Gly Thr Ala Ser Ser Leu Lys Lys Ile
625                 630                 635                 640

Asp Glu Leu Ile Ser Lys Ser Thr Glu Tyr His Gly Ser Cys Phe His
                645                 650                 655

Ile Leu Gln Lys Ser Ser Gln Thr Arg Trp Leu Ser His Lys Ile Trp
                660                 665                 670

Thr Asp Leu Gly His Glu Leu Glu Leu Leu Asn Leu Lys Ile Arg Asn
                675                 680                 685

Glu Glu Ala Asn Ile Ile Asp Leu Phe Lys Arg Lys Phe Ile Asp Arg
                690                 695                 700

Ser Asn Val Val Arg Gln Val Ala Thr Thr Leu Gly Tyr Leu Asp Thr
705                 710                 715                 720

Leu Ser Ser Phe Ala Val Leu Ala Asn Glu Arg Asn Leu Val Cys Pro
                725                 730                 735

Lys Val Asp Glu Ser Asn Lys Leu Glu Val Val Asn Gly Arg His Leu
                740                 745                 750

Met Val Glu Glu Gly Leu Ser Ala Arg Ser Leu Glu Thr Phe Thr Ala
                755                 760                 765

Asn Asn Cys Glu Leu Ala Lys Asp Asn Leu Trp Val Ile Thr Gly Pro
                770                 775                 780

Asn Met Gly Gly Lys Ser Thr Phe Leu Arg Gln Asn Ala Ile Ile Val
785                 790                 795                 800

Ile Leu Ala Gln Ile Gly Cys Phe Val Pro Cys Ser Lys Ala Arg Val
                805                 810                 815

Gly Ile Val Asp Lys Leu Phe Ser Arg Val Gly Ser Ala Asp Asp Leu
                820                 825                 830

Tyr Asn Glu Met Ser Thr Phe Met Val Glu Met Ile Glu Thr Ser Phe
                835                 840                 845

Ile Leu Gln Gly Ala Thr Glu Arg Ser Leu Ala Ile Leu Asp Glu Ile
                850                 855                 860

Gly Arg Gly Thr Ser Gly Lys Glu Gly Ile Ser Ile Ala Tyr Ala Thr
865                 870                 875                 880

Leu Lys Tyr Leu Leu Glu Asn Asn Gln Cys Arg Thr Leu Phe Ala Thr
                885                 890                 895
```

```
His Phe Gly Gln Glu Leu Lys Gln Ile Ile Asp Asn Lys Cys Ser Lys
            900                 905                 910
Gly Met Ser Glu Lys Val Lys Phe Tyr Gln Ser Gly Ile Thr Asp Leu
            915                 920                 925
Gly Gly Asn Asn Phe Cys Tyr Asn His Lys Leu Lys Pro Gly Ile Cys
    930                 935                 940
Thr Lys Ser Asp Ala Ile Arg Val Ala Glu Leu Ala Gly Phe Pro Met
945                 950                 955                 960
Glu Ala Leu Lys Glu Ala Arg Glu Ile Leu Gly
                965                 970
```

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

CGCGGATCCR WARTGNGTNA CRAA                                      24

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16323

(xi) SEQUENCE DESCRIPTION: SEQ ID NO:29:

CCAGGTGACA TTCAGAAC                                          18

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16411

(xi) SEQUENCE DESCRIPTION: SEQ ID NO:30:

CACATTGCTT CTAGTACAC                                        19

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16325

(xi) SEQUENCE DESCRIPTION: SEQ ID NO:31:

AATCAGTATT CCTGTGTAC                                        19

(2) INFORMATION FOR SEQ ID NO:32:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16390

(xi) SEQUENCE DESCRIPTION: SEQ ID NO:32:

CGTTACCCCC ACAAAGC                                          17

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16324

(xi) SEQUENCE DESCRIPTION: SEQ ID NO:33:

CGCGATTAAT CATCAGTG                                        18

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO

```
    (vii) IMMEDIATE SOURCE:
          (B) CLONE: oligo 16340

(xi) SEQUENCE DESCRIPTION: SEQ ID NO:34:

GGACAGAGAC ATACATTTCT ATC                                              23

(2) INFORMATION FOR SEQ ID NO:35:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: oligo 16326

(xi) SEQUENCE DESCRIPTION: SEQ ID NO:35:

TACCACATTT TATGTGATGG                                                  20

(2) INFORMATION FOR SEQ ID NO:36:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: oligo 16369

(xi) SEQUENCE DESCRIPTION: SEQ ID NO:36:

GGGGTAGTAA GTTTCCC                                                     17

(2) INFORMATION FOR SEQ ID NO:37:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: oligo 16322

(xi) SEQUENCE DESCRIPTION: SEQ ID NO:37:

CTCTTCTCAT GCTGTCCC                                                    18

(2) INFORMATION FOR SEQ ID NO:38:

(i) SEQUENCE CHARACTERISTICS:
         (A) LENGTH: 20 base pairs
```

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16339

(xi) SEQUENCE DESCRIPTION: SEQ ID NO:38:

ATAGAGAAGC TAAGTTAAAC                                                      20

(2) INFORMATION FOR SEQ ID NO:39:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16066

(xi) SEQUENCE DESCRIPTION: SEQ ID NO:39:

GCCTATGTCA ATTGCAAACA GTCCTCAG                                             28

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligo 16412

(xi) SEQUENCE DESCRIPTION: SEQ ID NO:40:

TAATTACTCA TGGGACATTC                                                      20

(2) INFORMATION FOR SEQ ID NO:41:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

TTYGCNACNC AYTTY
```

(2) INFORMATION FOR SEQ ID NO:42:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

```
TTYGCNACNC AYTAY                                                15
```

(2) INFORMATION FOR SEQ ID NO:43:

(i) SEQUENCE CHARACTERISTICS:
        (A) LENGTH: 3327 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Escherichia coli (vii) IMMEDIATE SOURCE:
        (B) CLONE: mutS (xi) SEQUENCE DESCRIPTION: SEQ ID NO:43:

```
AACTGCAAAT TGCCGGACAG ATCTGCCTGT CCGGCATACT ATTCATGAGG TTTTTTCGGA      60

CGATATTTTT CCGGCAGTTC TGGCACCGGA CGCTTGTCAT CGATGAGATG ACGCACGGTT     120

AAGATCGGAT GACGCCACAG CATTCTCGGC CCGGCCCAAC GCATAATCTG TTTCATCTCT     180

TCACGCTTTG CAGGCTGGTA ACAGTGCACC GGACACTGCT TACAGGCTGG TTTCTCTTCG     240

CCGAACACAC ATTTATCCAG CCGCTTTTGC GCGTAAACAA CAACGCCTC GTAATGCTCC      300

GGCTCCGCTG ACGCCTGCGG GCATTTCGCT TGATAAAGAT CGATCATTTT TTTAATCGTC     360

AGTTTTTCAC GAGAGATACG CTTGCCGGAC ATGCTGCCTC CACCTCATTA AGATGTATTT     420

ATATTACATC TTAATCTTAA AGGGCACTAT GACTCCAAAG AAGAAGGGTT AGCCAACCGA     480

TACAATTTTG CGTACTTGCT TCATAAGCAT CACGCAAAAG CTGCAAAACA GCATCTTTCC     540

CGGAACCAGC ATCAAGAACT CGCCGTTCGC TTCTTCCCCT GAAATGATTA ACTCCGGTAT     600

CATGTGCGCC TTATGTGATT ACAACGAAAA TAAAAACCAT CACACCCCAT TTAATATCAG     660

GGAACCGGAC ATAACCCCAT GAGTGCAATA GAAAATTTCG ACGCCCATAC GCCCATGATG     720

CAGCAGTATC TCAGGCTGAA AGCCCAGCAT CCCGAGATCC TGCTGTTTTA CCGGATGGGT     780

GATTTTATG AACTGTTTTA TGACGACGCA AAACGCGCGT CGCAACTGCT GGATATTTCA      840

CTGACCAAAC GCGGTGCTTC GGCGGGAGAG CCGATCCCGA TGGCGGGAT TCCCTACCAT      900

GCGGTGGAAA ACTATCTCGC CAAACTGGTG AATCAGGGAG AGTCCGTTGC CATCTGCGAA     960

CAAATTGGCG ATCCGGCGAC CAGCAAAGGT CCGGTTGAGC GCAAAGTTGT GCGTATCGTT    1020

ACGCCAGGCA CCATCAGCGA TGAAGCCCTG TTGCAGGAGC GTCAGGACAA CCTGCTGGCG    1080
```

```
GCTATCTGGC AGGACAGCAA AGGTTTCGGC TACGCGACGC TGGATATCAG TTCCGGGCGT      1140

TTTCGCCTGA GCGAACCGGC TGACCGCGAA ACGATGGCGG CAGAACTGCA ACGCACTAAT      1200

CCTGCGGAAC TGCTGTATGC AGAAGATTTT GCTGAAATGT CGTTAATTGA AGGCCGTCGC      1260

GGCCTGCGCC GTCGCCCGCT GTGGGAGTTT GAAATCGACA CCGCGCGCCA GCAGTTGAAT      1320

CTGCAATTTG GGACCCGCGA TCTGGTCGGT TTTGGCGTCG AGAACGCGCC GCGCGGACTT      1380

TGTGCTGCCG GTTGTCTGTT GCAGTATGCG AAAGATACCC AACGTACGAC TCTGCCGCAT      1440

ATTCGTTCCA TCACCATGGA ACGTGAGCAG GACAGCATCA TTATGGATGC CGCGACGCGT      1500

CGTAATCTGG AAATCACCCA GAACCTGGCG GGTGGTGCGG AAAATACGCT GGCTTCTGTG      1560

CTCGACTGCA CCGTCACGCC GATGGGCAGC CGTATGCTGA AACGCTGGCT GCATATGCCA      1620

GTGCGCGATA CCCGCGTGTT GCTTGAGCGC CAGCAAACTA TTGGCGCATT GCAGGATTTC      1680

ACCGCCGGGC TACAGCCGGT ACTGCGTCAG GTCGGCGACC TGGAACGTAT TCTGGCACGT      1740

CTGGCTTTAC GAACTGCTCG CCCACGCGAT CTGGCCCGTA TGCGCCACGC TTTCCAGCAA      1800

CTGCCGGAGC TGCGTGCGCA GTTAGAAACT GTCGATAGTG CACCGGTACA GGCGCTACGT      1860

GAGAAGATGG CGGAGTTTGC CGAGCTGCGC GATCTGCTGG AGCGAGCAAT CATCGACACA      1920

CCGCCGGTGC TGGTACGCGA CGGTGGTGTT ATCGCATCGG GCTATAACGA AGAGCTGGAT      1980

GAGTGGCGCG CGCTGGCTGA CGGCGCGACC GATTATCTGG AGCGTCTGGA AGTCCGCGAG      2040

CGTGAACGTA CCGGCCTGGA CACGCTGAAA GTTGGCTTTA ATGCGGTGCA CGGCTACTAC      2100

ATTCAAATCA GCCGTGGGCA AAGCCATCTG GCACCCATCA ACTACATGCG TCGCCAGACG      2160

CTGAAAAACG CCGAGCGCTA CATCATTCCA GAGCTAAAAG AGTACGAAGA TAAAGTTCTC      2220

ACCTCAAAAG GCAAAGCACT GGCACTGGAA AAACAGCTTT ATGAAGAGCT GTTCGACCTG      2280

CTGTTGCCGC ATCTGGAAGC GTTGCAACAG AGCGCGAGCG CGCTGGCGGA ACTCGACGTG      2340

CTGGTTAACC TGGCGGAACG GGCCTATACC CTGAACTACA CCTGCCCGAC CTTCATTGAT      2400

AAACCGGGCA TTCGCATTAC CGAAGGTCGC CATCCGGTAG TTGAACAAGT ACTGAATGAG      2460

CCATTTATCG CCAACCCGCT GAATCTGTCG CCGCAGCGCC GCATGTTGAT CATCACCGGT      2520

CCGAACATGG GCGGTAAAAG TACCTATATG CGCCAGACCG CACTGATTGC GCTGATGGCC      2580

TACATCGGCA GCTATGTACC GGCACAAAAA GTCGAGATTG GACCTATCGA TCGCATCTTT      2640

ACCCGCGTAG GCGCGGCAGA TGACCTGGCG TCCGGGCGCT CAACCTTTAT GGTGGAGATG      2700

ACTGAAACCG CCAATATTTT ACATAACGCC ACCGAATACA GTCTGGTGTT AATGGATGAG      2760

ATCGGGCGTG GAACGTCCAC CTACGATGGT CTGTCGCTGG CGTGGGCGTG CGCGGAAAAT      2820

CTGGCGAATA AGATTAAGGC ATTGACGTTA TTTGCTACCC ACTATTTCGA GCTGACCCAG      2880

TTACCGGAGA AAATGGAAGG CGTCGCTAAC GTGCATCTCG ATGCACTGGA GCACGGCGAC      2940

ACCATTGCCT TTATGCACAG CGTGCAGGAT GGCGCGGCGA GCAAAAGCTA CGGCCTGGCG      3000

GTTGCAGCTC TGGCAGGCGT GCCAAAAGAG GTTATTAAGC GCGCACGGCA AAAGCTGCGT      3060

GAGCTGGAAA GCATTTCGCC GAACGCCGCC GCTACGCAAG TGGATGGTAC GCAAATGTCT      3120

TTGCTGTCAG TACCAGAAGA AACTTCGCCT GCGGTCGAAG CTCTGGAAAA TCTTGATCCG      3180

GATTCACTCA CCCCGCGTCA GGCGCTGGAG TGGATTTATC GCTTGAAGAG CCTGGTGTAA      3240

TAACAATTCC CGATAGTCTT TTGCTATCGG GAATATTAAC GACAACTGAC GAATAAAATA      3300

AAAACACCCT GTATAATAGG AAAGCTT                                         3327
```

(2) INFORMATION FOR SEQ ID NO:44:

(i) SEQUENCE CHARACTERISTICS:
    (A) LENGTH: 853 amino acids
    (B) TYPE: amino acid
    (D) TOPOLOGY: linear (ii) MOLECULE TYPE: protein (iii) HYPOTHETICAL: NO (iv) ANTI-SENSE: NO (vi) ORIGINAL SOURCE:
    (A) ORGANISM: Escherichia coli (vii) IMMEDIATE SOURCE:
    (B) CLONE: MutS protein (xi) SEQUENCE DESCRIPTION: SEQ ID NO:44:

```
Met Ser Ala Ile Glu Asn Phe Asp Ala His Thr Pro Met Met Gln Gln
1               5                   10                  15

Tyr Leu Arg Leu Lys Ala Gln His Pro Glu Ile Leu Leu Phe Tyr Arg
            20                  25                  30

Met Gly Asp Phe Tyr Glu Leu Phe Tyr Asp Asp Ala Lys Arg Ala Ser
        35                  40                  45

Gln Leu Leu Asp Ile Ser Leu Thr Lys Arg Gly Ala Ser Ala Gly Glu
50                  55                  60

Pro Ile Pro Met Ala Gly Ile Pro Tyr His Ala Val Glu Asn Tyr Leu
65                  70                  75                  80

Ala Lys Leu Val Asn Gln Gly Glu Ser Val Ala Ile Cys Glu Gln Ile
                85                  90                  95

Gly Asp Pro Ala Thr Ser Lys Gly Pro Val Glu Arg Lys Val Val Arg
            100                 105                 110

Ile Val Thr Pro Gly Thr Ile Ser Asp Glu Ala Leu Leu Gln Glu Arg
        115                 120                 125

Gln Asp Asn Leu Leu Ala Ala Ile Trp Gln Asp Ser Lys Gly Phe Gly
130                 135                 140

Tyr Ala Thr Leu Asp Ile Ser Ser Gly Arg Phe Arg Leu Ser Glu Pro
145                 150                 155                 160

Ala Asp Arg Glu Thr Met Ala Ala Glu Leu Gln Arg Thr Asn Pro Ala
                165                 170                 175

Glu Leu Leu Tyr Ala Glu Asp Phe Ala Glu Met Ser Leu Ile Glu Gly
            180                 185                 190

Arg Arg Gly Leu Arg Arg Arg Pro Leu Trp Glu Phe Glu Ile Asp Thr
        195                 200                 205

Ala Arg Gln Gln Leu Asn Leu Gln Phe Gly Thr Arg Asp Leu Val Gly
210                 215                 220

Phe Gly Val Glu Asn Ala Pro Arg Gly Leu Cys Ala Ala Gly Cys Leu
225                 230                 235                 240

Leu Gln Tyr Ala Lys Asp Thr Gln Arg Thr Thr Leu Pro His Ile Arg
                245                 250                 255

Ser Ile Thr Met Glu Arg Glu Gln Asp Ser Ile Ile Met Asp Ala Ala
            260                 265                 270

Thr Arg Arg Asn Leu Glu Ile Thr Gln Asn Leu Ala Gly Gly Ala Glu
        275                 280                 285

Asn Thr Leu Ala Ser Val Leu Asp Cys Thr Val Thr Pro Met Gly Ser
290                 295                 300

Arg Met Leu Lys Arg Trp Leu His Met Pro Val Arg Asp Thr Arg Val
305                 310                 315                 320
```

-continued

```
Leu Leu Glu Arg Gln Gln Thr Ile Gly Ala Leu Gln Asp Phe Thr Ala
            325                 330                 335

Gly Leu Gln Pro Val Leu Arg Gln Val Gly Asp Leu Glu Arg Ile Leu
        340                 345                 350

Ala Arg Leu Ala Leu Arg Thr Ala Arg Pro Arg Asp Leu Ala Arg Met
    355                 360                 365

Arg His Ala Phe Gln Gln Leu Pro Glu Leu Arg Ala Gln Leu Glu Thr
370                 375                 380

Val Asp Ser Ala Pro Val Gln Ala Leu Arg Glu Lys Met Gly Glu Phe
385                 390                 395                 400

Ala Glu Leu Arg Asp Leu Leu Glu Arg Ala Ile Ile Asp Thr Pro Pro
                405                 410                 415

Val Leu Val Arg Asp Gly Gly Val Ile Ala Ser Gly Tyr Asn Glu Glu
            420                 425                 430

Leu Asp Glu Trp Arg Ala Leu Ala Asp Gly Ala Thr Asp Tyr Leu Glu
        435                 440                 445

Arg Leu Glu Val Arg Glu Arg Glu Arg Thr Gly Leu Asp Thr Leu Lys
    450                 455                 460

Val Gly Phe Asn Ala Val His Gly Tyr Tyr Ile Gln Ile Ser Arg Gly
465                 470                 475                 480

Gln Ser His Leu Ala Pro Ile Asn Tyr Met Arg Arg Gln Thr Leu Lys
                485                 490                 495

Asn Ala Glu Arg Tyr Ile Ile Pro Glu Leu Lys Glu Tyr Glu Asp Lys
            500                 505                 510

Val Leu Thr Ser Lys Gly Lys Ala Leu Ala Leu Glu Lys Gln Leu Tyr
        515                 520                 525

Glu Glu Leu Phe Asp Leu Leu Pro His Leu Glu Ala Leu Gln Gln
    530                 535                 540

Ser Ala Ser Ala Leu Ala Glu Leu Asp Val Leu Val Asn Leu Ala Glu
545                 550                 555                 560

Arg Ala Tyr Thr Leu Asn Tyr Thr Cys Pro Thr Phe Ile Asp Lys Pro
                565                 570                 575

Gly Ile Arg Ile Thr Glu Gly Arg His Pro Val Val Glu Gln Val Leu
            580                 585                 590

Asn Glu Pro Phe Ile Ala Asn Pro Leu Asn Leu Ser Pro Gln Arg Arg
        595                 600                 605

Met Leu Ile Ile Thr Gly Pro Asn Met Gly Gly Lys Ser Thr Tyr Met
    610                 615                 620

Arg Gln Thr Ala Leu Ile Ala Leu Met Ala Tyr Ile Gly Ser Tyr Val
625                 630                 635                 640

Pro Ala Gln Lys Val Glu Ile Gly Pro Ile Asp Arg Ile Phe Thr Arg
                645                 650                 655

Val Gly Ala Ala Asp Asp Leu Ala Ser Gly Arg Ser Thr Phe Met Val
            660                 665                 670

Glu Met Thr Glu Thr Ala Asn Ile Leu His Asn Ala Thr Glu Tyr Ser
        675                 680                 685

Leu Val Leu Met Asp Glu Ile Gly Arg Gly Thr Ser Thr Tyr Asp Gly
    690                 695                 700

Leu Ser Leu Ala Trp Ala Cys Ala Glu Asn Leu Ala Asn Lys Ile Lys
705                 710                 715                 720

Ala Leu Thr Leu Phe Ala Thr His Tyr Phe Glu Leu Thr Gln Leu Pro
                725                 730                 735

Glu Lys Met Glu Gly Val Ala Asn Val His Leu Asp Ala Leu Glu His
```

```
                    740            745             750
Gly Asp Thr Ile Ala Phe Met His Ser Val Gln Asp Gly Ala Ala Ser
            755                 760                 765
Lys Ser Tyr Gly Leu Ala Val Ala Ala Leu Ala Gly Val Pro Lys Glu
            770                 775                 780
Val Ile Lys Arg Ala Arg Gln Lys Leu Arg Glu Leu Glu Ser Ile Ser
785                 790                 795                 800
Pro Asn Ala Ala Ala Thr Gln Val Asp Gly Thr Gln Met Ser Leu Leu
                805                 810                 815
Ser Val Pro Glu Glu Thr Ser Pro Ala Val Glu Ala Leu Glu Asn Leu
                820                 825                 830
Asp Pro Asp Ser Leu Thr Pro Arg Gln Ala Leu Glu Trp Ile Tyr Arg
                835                 840                 845
Leu Lys Ser Leu Val
                850

(2) INFORMATION FOR SEQ ID NO:45:

(i) SEQUENCE CHARACTERISTICS:
        (A) LENGTH: 3095 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Homo sapiens (vii) IMMEDIATE SOURCE:
          (B) CLONE: hMSH2 cDNA (xi) SEQUENCE DESCRIPTION: SEQ ID NO:45:

ATGGCGGTGC AGCCGAAGGA GACGCTGCAG TTGGAGAGCG CGGCCGAGGT CGGCTTCGTG      60

CGCTTCTTTC AGGGCATGCC GGAGAAGCCG ACCACCACAG TGCGCCTTTT CGACCGGGGC     120

GACTTCTATA CGGCGCACGG CGAGGACGCG CTGCTGGCCG CCCGGGAGGT GTTCAAGACC     180

CAGGGGGTGA TCAAGTACAT GGGGCCGGCA GGAGCAAAGA ATCTGCAGAG TGTTGTGCTT     240

AGTAAAATGA ATTTTGAATC TTTTGTAAAA GATCTTCTTC TGGTTCGTCA GTATAGAGTT     300

GAAGTTTATA AGAATAGAGC TGGAAATAAG GCATCCAAGG AGAATGATTG GTATTTGGCA     360

TATAAGGCTT CTCCTGGCAA TCTCTCTCAG TTTGAAGATA TTCTCTTTGG TAACAATGAT     420

ATGTCAGCTT CCATTGGTGT TGTGGGTGTT AAAATGTCCG CAGTTGATGG CCAGAGACAG     480

GTTGGAGTTG GGTATGTGGA TTCCATACAG AGGAAACTAG GACTGTGTGA ATTCCCTGAT     540

AATGATCAGT TCTCCAATCT TGAGGCTCTC CTCATCCAGA TTGGACCAAA GGAATGTGTT     600

TTACCCGGAG AGAGACTGCT GGAGACATG GGGAAACTGA CAGATAAT TCAAAGAGGA        660

GGAATTCTGA TCAGAGAAAG AAAAAAAGCT GACTTTTCCA CAAAAGACAT TTATCAGGAC     720

CTCAACCGGT TGTTGAAAGG CAAAAAGGGA GAGCAGATGA ATAGTGCTGT ATTGCCAGAA     780

ATGGAGAATC AGGTTGCAGT TTCATCACTG TCTGCGGTAA TCAAGTTTTT AGAACTCTTA     840

TCAGATGATT CCAACTTTGG ACAGTTTGAA CTGACTACTT TTGACTTCAG CCAGTATATG     900

AAATTGGATA TTGCAGCAGT CAGAGCCCTT AACCTTTTTC AGGGTTCTGT TGTAGATACC     960

ACTGGCTCTC AGTCTCTGGC TGCCTTGCTG AATAAGTGTA AACCCCTCA AGGACAAAGA    1020
```

```
CTTGTTAACC AGTGGATTAA GCAGCCTCTC ATGGATAAGA ACAGAATAGA GGAGAGATTG    1080

AATTTAGTGG AAGCTTTTGT AGAAGATGCA GAATTGAGGC AGACTTTACA AGAAGATTTA    1140

CTTCGTCGAT TCCCAGATCT TAACCGACTT GCCAAGAAGT TTCAAAGACA AGCAGCAAAC    1200

TTACAAGATT GTTACCGACT CTATCAGGGT ATAAATCAAC TACCTAATGT TATACAGGCT    1260

CTGGAAAAAC ATGAAGGAAA ACACCAGAAA TTATTGTTGG CAGTTTTTGT GACTCCTCTT    1320

ACTGATCTTC GTTCTGACTT CTCCAAGTTT CAGGAAATGA TAGAAACAAC TTTAGATATG    1380

GATCAGGTGG AAAACCATGA ATTCCTTGTA AAACCTTCAT TGATCCTAA TCTCAGTGAA     1440

TTAAGAGAAA TAATGAATGA CTTGGAAAAG AAGATGCAGT CAACATTAAT AAGTGCAGCC    1500

AGAGATCTTG GCTTGGACCC TGGCAAACAG ATTAAACTGG ATTCCAGTGC ACAGTTTGGA    1560

TATTACTTTC GTGTAACCTG TAAGGAAGAA AAAGTCCTTC GTAACAATAA AAACTTTAGT    1620

ACTGTAGATA TCCAGAAGAA TGGTGTTAAA TTTACCAACA GCAAATTGAC TTCTTTAAAT    1680

GAAGAGTATA CCAAAAATAA AACAGAATAT GAAGAAGCCC AGGATGCCAT TGTTAAAGAA    1740

ATTGTCAATA TTTCTTCAGG CTATGTAGAA CCAATGCAGA CACTCAATGA TGTGTTAGCT    1800

CAGCTAGATG CTGTTGTCAG CTTTGCTCAC GTGTCAAATG GAGCACCTGT TCCATATGTA    1860

CGACCAGCCA TTTTGGAGAA AGGACAAGGA AGAATTATAT TAAAAGCATC CAGGCATGCT    1920

TGTGTTGAAG TTCAAGATGA AATTGCATTT ATTCCTAATG ACGTATACTT TGAAAAGAT     1980

AAACAGATGT TCCACATCAT TACTGGCCCC AATATGGGAG GTAAATCAAC ATATATTCGA    2040

CAAACTGGGG TGATAGTACT CATGGCCCAA ATTGGGTGTT TTGTGCCATG TGAGTCAGCA    2100

GAAGTGTCCA TTGTGGACTG CATCTTAGCC CGAGTAGGGG CTGGTGACAG TCAATTGAAA    2160

GGAGTCTCCA CGTTCATGGC TGAAATGTTG GAAACTGCTT CTATCCTCAG GTCTGCAACC    2220

AAAGATTCAT TAATAATCAT AGATGAATTG GGAAGAGGAA CTTCTACCTA CGATGGATTT    2280

GGGTTAGCAT GGGCTATATC AGAATACATT GCAACAAAGA TTGGTGCTTT TTGCATGTTT    2340

GCAACCCATT TTCATGAACT TACTGCCTTG GCCAATCAGA TACCAACTGT TAATAATCTA    2400

CATGTCACAG CACTCACCAC TGAAGAGACC TTAACTATGC TTTATCAGGT GAAGAAAGGT    2460

GTCTGTGATC AAAGTTTTGG GATTCATGTT GCAGAGCTTG CTAATTTCCC TAAGCATGTA    2520

ATAGAGTGTG CTAAACAGAA AGCCCTGGAA CTTGAGGAGT TCAGTATAT  TGGAGAATCG    2580

CAAGGATATG ATATCATGGA ACCAGCAGCA AGAAGTGCT  ATCTGGAAAG AGAGCAAGGT    2640

GAAAAATTA  TTCAGGAGTT CCTGTCCAAG GTGAAACAAA TGCCCTTTAC TGAAATGTCA    2700

GAAGAAAACA TCACAATAAA GTTAAAACAG CTAAAAGCTG AAGTAATAGC AAAGAATAAT    2760

AGCTTTGTAA ATGAAATCAT TTCACGAATA AAAGTTACTA CGTGAAAAAT CCCAGTAATG    2820

GAATGAAGGT AATATTGATA AGCTATTGTC TGTAATAGTT TTATATTGTT TTATATTAAC    2880

CCTTTTTCCA TAGTGTTAAC TGTCAGTGCC CATGGGCTAT CAACTTAATA AGATATTTAG    2940

TAATATTTTA CTTTGAGGAC ATTTTCAAAG ATTTTTATTT TGAAAATGA  GAGCTGTAAC    3000

TGAGGACTGT TTGCAATTGA CATAGGCAAT AATAAGTGAT GTGCTGAATT TTTATAAAAA    3060

ATCATGAGTT TGGGAAAAAA AAAAAAAAAA AAAAA                              3095
```

(2) INFORMATION FOR SEQ ID NO:46:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: primer 18538

(xi) SEQUENCE DESCRIPTION: SEQ ID NO:46:

TCGCGCATTT TCTTCAACC                                                        19

(2) INFORMATION FOR SEQ ID NO:47:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: primer 17209

(xi) SEQUENCE DESCRIPTION: SEQ ID NO:47:

GTCCCTCCCC AGCACGC                                                          17

(2) INFORMATION FOR SEQ ID NO:48:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: primer 18183

(xi) SEQUENCE DESCRIPTION: SEQ ID NO:48:

GAAGTCCAGC TAATACAGTG C                                                     21

(2) INFORMATION FOR SEQ ID NO:49:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: primer 18230

(xi) SEQUENCE DESCRIPTION: SEQ ID NO:49:

CTTCACATTT TTATTTTTCT ACTC                                                  24

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18226

(xi) SEQUENCE DESCRIPTION: SEQ ID NO:50:

GCTTATAAAA TTTTAAAGTA TGTTC                                              25

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18180

(xi) SEQUENCE DESCRIPTION: SEQ ID NO:51:

GCCTTTCCTA GGCCTGGAAT CTCC                                               24

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18298

(xi) SEQUENCE DESCRIPTION: SEQ ID NO:52:

TTCATTTTTG CTTTTCTTAT TCC                                                23

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: primer 18545

(xi) SEQUENCE DESCRIPTION: SEQ ID NO:53:

ATATGACAGA AATATCCTTC                                                   20

(2) INFORMATION FOR SEQ ID NO:54:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: primer 18220

(xi) SEQUENCE DESCRIPTION: SEQ ID NO:54:

CCAGTGGTAT AGAAATCTTC G                                                 21

(2) INFORMATION FOR SEQ ID NO:55:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: primer 18572

(xi) SEQUENCE DESCRIPTION: SEQ ID NO:55:

CCAATCAACA TTTTTAACCC                                                   20

(2) INFORMATION FOR SEQ ID NO:56:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: primer 18221

(xi) SEQUENCE DESCRIPTION: SEQ ID NO:56:

GTTTTCACTA ATGAGCTTGC C                                                 21

(2) INFORMATION FOR SEQ ID NO:57:

-continued

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18900

(xi) SEQUENCE DESCRIPTION: SEQ ID NO:57:

GTGGTATAAT CATGTGGG                                               18

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18573

(xi) SEQUENCE DESCRIPTION: SEQ ID NO:58:

GACTTACGTG CTTAGTTG                                               18

(2) INFORMATION FOR SEQ ID NO:59:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18222

(xi) SEQUENCE DESCRIPTION: SEQ ID NO:59:

GTATATATTG TATGAGTTGA AGG                                         23

(2) INFORMATION FOR SEQ ID NO:60:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
```

(B) CLONE: primer 18223

(xi) SEQUENCE DESCRIPTION: SEQ ID NO:60:

GATTTGTATT CTGTAAAATG AGATC                                                25

(2) INFORMATION FOR SEQ ID NO:61:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18294

(xi) SEQUENCE DESCRIPTION: SEQ ID NO:61:

GGCCTTTGCT TTTAAAAAT AAC                                                   23

(2) INFORMATION FOR SEQ ID NO:62:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 17231

(xi) SEQUENCE DESCRIPTION: SEQ ID NO:62:

GTCTTTACCC ATTATTTATA GG                                                   22

(2) INFORMATION FOR SEQ ID NO:63:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 17232

(xi) SEQUENCE DESCRIPTION: SEQ ID NO:63:

GTATAGACAA AAGAATTATT CC                                                   22

(2) INFORMATION FOR SEQ ID NO:64:

(i) SEQUENCE CHARACTERISTICS:
        (A) LENGTH: 19 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 16325

(xi) SEQUENCE DESCRIPTION: SEQ ID NO:64:

ATTCAGTATT CCTGTGTAC                                                    19

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 16858

(xi) SEQUENCE DESCRIPTION: SEQ ID NO:65:

TACCTTCATT CCATTACTGG                                                   20

(2) INFORMATION FOR SEQ ID NO:66:

(i) SEQUENCE CHARACTERISTICS:
        (A) LENGTH: 211 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 1

(xi) SEQUENCE DESCRIPTION: SEQ ID NO:66:

ATGGCGGTGC AGCCGAAGGA GACGCTGCAG TTGGAGAGCG CGGCCGAGGT CGGCTTCGTG        60

CGCTTCTTTC AGGGCATGCC GGAGAAGCCG ACCACCACAG TGCGCCTTTT CGACCGGGGC       120

GACTTCTATA CGGCGCACGG CGAGGACGCG CTGCTGGCCG CCCGGGAGGT GTTCAAGACC       180

CAGGGGGTGA TCAAGTACAT GGGGCCGGCA G                                      211

(2) INFORMATION FOR SEQ ID NO:67:

(i) SEQUENCE CHARACTERISTICS:
        (A) LENGTH: 155 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 2

(xi) SEQUENCE DESCRIPTION: SEQ ID NO:67:

GAGCAAAGAA TCTGCAGAGT GTTGTGCTTA GTAAAATGAA TTTTGAATCT TTTGTAAAAG    60

ATCTTCTTCT GGTTCGTCAG TATAGAGTTG AAGTTTATAA GAATAGAGCT GGAAATAAGG   120

CATCCAAGGA GAATGATTGG TATTTGGCAT ATAAG                              155

(2) INFORMATION FOR SEQ ID NO:68:

(i) SEQUENCE CHARACTERISTICS:
        (A) LENGTH: 279 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 3

(ix) FEATURE:
        (A) NAME/KEY: allele
        (B) LOCATION: replace T(33) with C (xi) SEQUENCE DESCRIPTION: SEQ ID NO:68:

GCTTCTCCTG GCAATCTCTC TCAGTTTGAA GATATTCTCT TTGGTAACAA TGATATGTCA    60

GCTTCCATTG GTGTTGTGGG TGTTAAAATG TCCGCAGTTG ATGGCCAGAG ACAGGTTGGA   120

GTTGGGTATG TGGATTCCAT ACAGAGGAAA CTAGGACTGT GTGAATTCCC TGATAATGAT   180

CAGTTCTCCA ATCTTGAGGC TCTCCTCATC CAGATTGGAC CAAAGGAATG TGTTTTACCC   240

GGAGGAGAGA CTGCTGGAGA CATGGGGAAA CTGAGACAG                          279

(2) INFORMATION FOR SEQ ID NO:69:

(i) SEQUENCE CHARACTERISTICS:
        (A) LENGTH: 147 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 4

(xi) SEQUENCE DESCRIPTION: SEQ ID NO:69:

ATAATTCAAA GAGGAGGAAT TCTGATCACA GAAAGAAAAA AAGCTGACTT TTCCACAAAA    60

GACATTTATC AGGACCTCAA CCGGTTGTTG AAAGGCAAAA AGGGAGAGCA GATGAATAGT   120

GCTGTATTGC CAGAAATGGA GAATCAG                                      147

(2) INFORMATION FOR SEQ ID NO:70:

(i) SEQUENCE CHARACTERISTICS:
        (A) LENGTH: 150 base pairs
        (B) TYPE: nucleic acid
        (C) STRANDEDNESS: both (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 5

(xi) SEQUENCE DESCRIPTION: SEQ ID NO:70:

```
GTTGCAGTTT CATCACTGTC TGCGGTAATC AAGTTTTTAG AACTCTTATC AGATGATTCC        60

AACTTTGGAC AGTTTGAACT GACTACTTTT GACTTCAGCC AGTATATGAA ATTGGATATT       120

GCAGCAGTCA GAGCCCTTAA CCTTTTTCAG                                        150
```

(2) INFORMATION FOR SEQ ID NO:71:

(i) SEQUENCE CHARACTERISTICS:
        (A) LENGTH: 134 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 6

(xi) SEQUENCE DESCRIPTION: SEQ ID NO:71:

```
GGTTCTGTTG AAGATACCAC TGGCTCTCAG TCTCTGGCTG CCTTGCTGAA TAAGTGTAAA        60

ACCCCTCAAG GACAAAGACT TGTTAACCAG TGGATTAAGC AGCCTCTCAT GGATAAGAAC       120

AGAATAGAGG AGAG                                                         134
```

(2) INFORMATION FOR SEQ ID NO:72:

(i) SEQUENCE CHARACTERISTICS:
        (A) LENGTH: 200 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 7

(xi) SEQUENCE DESCRIPTION: SEQ ID NO:72:

```
ATTGAATTTA GTGGAAGCTT TTGTAGAAGA TGCAGAATTG AGGCAGACTT TACAAGAAGA        60

TTTACTTCGT CGATTCCCAG ATCTTAACCG ACTTGCCAAG AAGTTTCAAA GACAAGCAGC       120

AAACTTACAA GATTGTTACC GACTCTATCA GGGTATAAAT CAACTACCTA ATGTTATACA       180

GGCTCTGGAA AAACATGAA G                                                  200
```

(2) INFORMATION FOR SEQ ID NO:73:

(i) SEQUENCE CHARACTERISTICS:
        (A) LENGTH: 110 base pairs
        (B) TYPE: nucleic acid (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 8

(xi) SEQUENCE DESCRIPTION: SEQ ID NO:73:

GAAAACACCA GAAATTATTG TTGGCAGTTT TTGTGACTCC TCTTACTGAT CTTCGTTCTG      60

ACTTCTCCAA GTTTCAGGAA ATGATAGAAA CAACTTTAGA TATGGATCAG                110

(2) INFORMATION FOR SEQ ID NO:74:

(i) SEQUENCE CHARACTERISTICS:
        (A) LENGTH: 124 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 43

(xi) SEQUENCE DESCRIPTION: SEQ ID NO:74:

GTGGAAAACC ATGAATTCCT TGTAAAACCT TCATTTGATC CTAATCTCAG TGAATTAAGA      60

GAAATAATGA ATGACTTGGA AAAGAAGATG CAGTCAACAT TAATAAGTGC AGCCAGAGAT    120

CTTG                                                                 124

(2) INFORMATION FOR SEQ ID NO:75:

(i) SEQUENCE CHARACTERISTICS:
        (A) LENGTH: 151 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 10

(xi) SEQUENCE DESCRIPTION: SEQ ID NO:75:

GCTTGGACCC TGGCAAACAG ATTAAACTGG ATTCCAGTGC ACAGTTTGGA TATTACTTTC      60

GTGTAACCTG TAAGGAAGAA AAAGTCCTTC GTAACAATAA AAACTTTAGT ACTGTAGATA    120

TCCAGAAGAA TGGTGTTAAA TTTACCAACA G                                   151

(2) INFORMATION FOR SEQ ID NO:76:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 11

(xi) SEQUENCE DESCRIPTION: SEQ ID NO:76:

CAAATTGACT TCTTTAAATG AAGAGTATAC CAAAAATAAA ACAGAATATG AAGAAGCCCA        60

GGATGCCATT GTTAAAGAAA TTGTCAATAT TTCTTCAG        98

(2) INFORMATION FOR SEQ ID NO:77:

(i) SEQUENCE CHARACTERISTICS:
        (A) LENGTH: 246 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 12

(xi) SEQUENCE DESCRIPTION: SEQ ID NO:77:

GCTATGTAGA ACCAATGCAG ACACTCAATG ATGTGTTAGC TCAGCTAGAT GCTGTTGTCA        60

GCTTTGCTCA CGTGTCAAAT GGAGCACCTG TTCCATATGT ACGACCAGCC ATTTTGGAGA       120

AAGGACAAGG AAGAATTATA TTAAAAGCAT CCAGGCATGC TTGTGTTGAA GTTCAAGATG       180

AAATTGCATT TATTCCTAAT GACGTATACT TGAAAAAGA TAAACAGATG TTCCACATCA       240

TTACTG       246

(2) INFORMATION FOR SEQ ID NO:78:

(i) SEQUENCE CHARACTERISTICS:
        (A) LENGTH: 205 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 13

(xi) SEQUENCE DESCRIPTION: SEQ ID NO:78:

GCCCCAATAT GGGAGGTAAA TCAACATATA TTCGACAAAC TGGGGTGATA GTACTCATGG        60

CCCAAATTGG GTGTTTTGTG CCATGTGAGT CAGCAGAAGT GTCCATTGTG GACTGCATCT       120

TAGCCCGAGT AGGGGCTGGT GACAGTCAAT TGAAAGGAGT CTCCACGTTC ATGGCTGAAA       180

TGTTGGAAAC TGCTTCTATC CTCAG       205

(2) INFORMATION FOR SEQ ID NO:79:

(i) SEQUENCE CHARACTERISTICS:
        (A) LENGTH: 248 base pairs
        (B) TYPE: nucleic acid

```
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 14

(xi) SEQUENCE DESCRIPTION: SEQ ID NO:79:

GTCTGCAACC AAAGATTCAT TAATAATCAT AGATGAATTG GGAAGAGGAA CTTCTACCTA      60

CGATGGATTT GGGTTAGCAT GGGCTATATC AGAATACATT GCAACAAAGA TTGGTGCTTT     120

TTGCATGTTT GCAACCCATT TTCATGAACT TACTGCCTTG GCCAATCAGA TACCAACTGT     180

TAATAATCTA CATGTCACAG CACTCACCAC TGAAGAGACC TTAACTATGC TTTATCAGGT     240

GAAGAAAG                                                              248

(2) INFORMATION FOR SEQ ID NO:80:

(i) SEQUENCE CHARACTERISTICS:
        (A) LENGTH: 176 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 15

(xi) SEQUENCE DESCRIPTION: SEQ ID NO:80:

GTGTCTGTGA TCAAAGTTTT GGGATTCATG TTGCAGAGCT TGCTAATTTC CCTAAGCATG      60

TAATAGAGTG TGCTAAACAG AAAGCCCTGG AACTTGAGGA GTTTCAGTAT ATTGGAGAAT     120

CGCAAGGATA TGATATCATG GAACCAGCAG CAAAGAAGTG CTATCTGGAA AGAGAG        176

(2) INFORMATION FOR SEQ ID NO:81:

(i) SEQUENCE CHARACTERISTICS:
        (A) LENGTH: 171 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: hMSH2 exon 16

(xi) SEQUENCE DESCRIPTION: SEQ ID NO:81:

CAAGGTGAAA AAATTATTCA GGAGTTCCTG TCCAAGGTGA ACAAATGCC CTTTACTGAA       60

ATGTCAGAAG AAAACATCAC AATAAAGTTA AACAGCTAA AAGCTGAAGT AATAGCAAAG     120

AATAATAGCT TTGTAAATGA AATCATTTCA CGAATAAAAG TTACTACGTG A             171

(2) INFORMATION FOR SEQ ID NO:82:
```

(i) SEQUENCE CHARACTERISTICS:
        (A) LENGTH: 68 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed sequence upstream of hMSH2 exon 1

(xi) SEQUENCE DESCRIPTION: SEQ ID NO:82:

GGCGGGAAAC AGCTTAGTGG GTGTGGGGTC GCGCATTTTC TTCAACCAGG AGGTGAGGAG    60

GTTTCGAC                                                            68

(2) INFORMATION FOR SEQ ID NO:83:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 1

(xi) SEQUENCE DESCRIPTION: SEQ ID NO:83:

GTGAGGGCCG GGACGGCGCG TGCTGGGGAG GGAC                                34

(2) INFORMATION FOR SEQ ID NO:84:

(i) SEQUENCE CHARACTERISTICS:
        (A) LENGTH: 70 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 2

(xi) SEQUENCE DESCRIPTION: SEQ ID NO:84:

GAAGTCCAGC TAATACAGTG CTTGAACATG TAATATCTCA AATCTGTAAT GTACTTTTTT    60

TTTTTTTAAG                                                          70

(2) INFORMATION FOR SEQ ID NO:85:

(i) SEQUENCE CHARACTERISTICS:
        (A) LENGTH: 61 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
    (B) CLONE: confirmed intron sequence downstream of hMSH2 exon 2

(xi) SEQUENCE DESCRIPTION: SEQ ID NO:85:

```
GTAATTATCT TCCTTTTTAA TTTACTTATT TTTTTAAGAG TAGAAAAATA AAAATGTGAA    60

G                                                                    61
```

(2) INFORMATION FOR SEQ ID NO:86:

(i) SEQUENCE CHARACTERISTICS:
       (A) LENGTH: 65 base pairs
       (B) TYPE: nucleic acid
       (C) STRANDEDNESS: both
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
       (B) CLONE: confirmed intron sequence upstream of hMSH2 exon 3

(xi) SEQUENCE DESCRIPTION: SEQ ID NO:86:

```
TGCTTATAAA ATTTTAAAGT ATGTTCAAGA GTTTGTTAAA TTTTTAAAAT TTTATTTTTA    60

CTTAG                                                                65
```

(2) INFORMATION FOR SEQ ID NO:87:

(i) SEQUENCE CHARACTERISTICS:
       (A) LENGTH: 50 base pairs
       (B) TYPE: nucleic acid
       (C) STRANDEDNESS: both
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
       (B) CLONE: confirmed intron sequence downstream of hMSH2 exon 3

(xi) SEQUENCE DESCRIPTION: SEQ ID NO:87:

```
GTAAGCAAAT TGAGTCTAGT GATAGAGGAG ATTCCAGGCC TAGGAAAGGC                50
```

(2) INFORMATION FOR SEQ ID NO:88:

(i) SEQUENCE CHARACTERISTICS:
       (A) LENGTH: 61 base pairs
       (B) TYPE: nucleic acid
       (C) STRANDEDNESS: both
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:

(B) CLONE: confirmed intron sequence upstream of hMSH2
            exon 4

(xi) SEQUENCE DESCRIPTION: SEQ ID NO:88:

TTCATTTTTG CTTTTCTTAT TCCTTTTCTC ATAGTAGTTT AAACTATTTC TTTCAAAATA    60

G                                                                    61

(2) INFORMATION FOR SEQ ID NO:89:

(i) SEQUENCE CHARACTERISTICS:
        (A) LENGTH: 108 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 4

(xi) SEQUENCE DESCRIPTION: SEQ ID NO:89:

GTACATGGAT TATAAATGTG AATTACAATA TATATAATGT AAATATGTAA TATATAATAA    60

ATAATATGTA AACTATAGTG ACTTTTTAGA AGGATATTTC TGTCATAT               108

(2) INFORMATION FOR SEQ ID NO:90:

(i) SEQUENCE CHARACTERISTICS:
        (A) LENGTH: 43 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 5

(xi) SEQUENCE DESCRIPTION: SEQ ID NO:90:

CCAGTGGTAT AGAAATCTTC GATTTTTAAA TTCTTAATTT TAG                      43

(2) INFORMATION FOR SEQ ID NO:91:

(i) SEQUENCE CHARACTERISTICS:
        (A) LENGTH: 48 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 5

(ix) FEATURE:
        (A) NAME/KEY: misc_feature
        (B) LOCATION: 3..28

-continued (D) OTHER INFORMATION: /standard_name= "poly-A tract--
            exact number of As may need confirmation"

(xi) SEQUENCE DESCRIPTION: SEQ ID NO:91:

GTAAAAAAAA AAAAAAAAAA AAAAAAAAGG GTTAAAAATG TTGATTGG                48

(2) INFORMATION FOR SEQ ID NO:92:

(i) SEQUENCE CHARACTERISTICS:
        (A) LENGTH: 51 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 6

(xi) SEQUENCE DESCRIPTION: SEQ ID NO:92:

GTTTTCACTA ATGAGCTTGC CATTCTTTCT ATTTTATTTT TTGTTTACTA G             51

(2) INFORMATION FOR SEQ ID NO:93:

(i) SEQUENCE CHARACTERISTICS:
        (A) LENGTH: 66 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 6

(xi) SEQUENCE DESCRIPTION: SEQ ID NO:93:

GTATGTTATT AGTTTATACT TTCGTTAGTT TTATGTAACC TGCAGTTACC CACATGATTA    60

TACCAC                                                              66

(2) INFORMATION FOR SEQ ID NO:94:

(i) SEQUENCE CHARACTERISTICS:
        (A) LENGTH: 75 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 7

(xi) SEQUENCE DESCRIPTION: SEQ ID NO:94:

GACTTACGTG CTTAGTTGAT AAATTTTAAT TTTATACTAA AATATTTTAC ATTAATTCAA    60

GTTAATTTAT TTCAG                                                    75

(2) INFORMATION FOR SEQ ID NO:95:

(i) SEQUENCE CHARACTERISTICS:
       (A) LENGTH: 52 base pairs
       (B) TYPE: nucleic acid
       (C) STRANDEDNESS: both
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 7

(xi) SEQUENCE DESCRIPTION: SEQ ID NO:95:

GTAACAAGT GATTTTGTTT TTTTGTTTTC CTTCAACTCA TACAATATAT ACT        52

(2) INFORMATION FOR SEQ ID NO:96:

(i) SEQUENCE CHARACTERISTICS:
       (A) LENGTH: 58 base pairs
       (B) TYPE: nucleic acid
       (C) STRANDEDNESS: both
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 8

(xi) SEQUENCE DESCRIPTION: SEQ ID NO:96:

GATTTGTATT CTGTAAAATG AGATCTTTTT ATTTGTTTGT TTTACTACTT TCTTTTAG        58

(2) INFORMATION FOR SEQ ID NO:97:

(i) SEQUENCE CHARACTERISTICS:
       (A) LENGTH: 54 base pairs
       (B) TYPE: nucleic acid
       (C) STRANDEDNESS: both
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 8

(xi) SEQUENCE DESCRIPTION: SEQ ID NO:97:

GTATGCAATA TACTTTTTAA TTTAAGCAGT AGTTATTTTT AAAAAGCAAA GGCC        54

(2) INFORMATION FOR SEQ ID NO:98:

(i) SEQUENCE CHARACTERISTICS:
       (A) LENGTH: 48 base pairs
       (B) TYPE: nucleic acid
       (C) STRANDEDNESS: both
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 9

(xi) SEQUENCE DESCRIPTION: SEQ ID NO:98:

GTCTTTACCC ATTATTTATA GGATTTTGTC ACTTTGTTCT GTTTGCAG        48

(2) INFORMATION FOR SEQ ID NO:99:

(i) SEQUENCE CHARACTERISTICS:
        (A) LENGTH: 45 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 9

(xi) SEQUENCE DESCRIPTION: SEQ ID NO:99:

GTAAGAATGG GTCATTGGAG GTTGGAATAA TTCTTTTGTC TATAC        45

(2) INFORMATION FOR SEQ ID NO:100:

(i) SEQUENCE CHARACTERISTICS:
        (A) LENGTH: 49 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 10

(xi) SEQUENCE DESCRIPTION: SEQ ID NO:100:

GGTAGTAGGT ATTTATGGAA TACTTTTTCT TTTCTTCTTG TTTATCAAG        49

(2) INFORMATION FOR SEQ ID NO:101:

(i) SEQUENCE CHARACTERISTICS:
        (A) LENGTH: 59 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 10

(xi) SEQUENCE DESCRIPTION: SEQ ID NO:101:

GTTTGTAAGT CATTATTATA TTTTTAACCC TTTATTAATT CCCTAAATGC TCTAACATG      59

(2) INFORMATION FOR SEQ ID NO:102:

(i) SEQUENCE CHARACTERISTICS:
        (A) LENGTH: 59 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 11

(xi) SEQUENCE DESCRIPTION: SEQ ID NO:102:

CACATTGCTT CTAGTACACA TTTTAATATT TTTAATAAAA CTGTTATTTC GATTTGCAG      59

(2) INFORMATION FOR SEQ ID NO:103:

(i) SEQUENCE CHARACTERISTICS:
        (A) LENGTH: 41 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 11

(xi) SEQUENCE DESCRIPTION: SEQ ID NO:103:

GTAAACTTAA TAGAACTAAT AATGTTCTGA ATGTCACCTG G                        41

(2) INFORMATION FOR SEQ ID NO:104:

(i) SEQUENCE CHARACTERISTICS:
        (A) LENGTH: 44 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 12

(xi) SEQUENCE DESCRIPTION: SEQ ID NO:104:

ATTCAGTATT CCTGTGTACA TTTTCTGTTT TTATTTTTAT ACAG                     44

(2) INFORMATION FOR SEQ ID NO:105:

(i) SEQUENCE CHARACTERISTICS:
        (A) LENGTH: 37 base pairs
        (B) TYPE: nucleic acid

```
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 12

(xi) SEQUENCE DESCRIPTION: SEQ ID NO:105:

GTAAAAAACC TGGTTTTTGG GCTTTGTGGG GGTAACG                              37

(2) INFORMATION FOR SEQ ID NO:106:

(i) SEQUENCE CHARACTERISTICS:
        (A) LENGTH: 99 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 13

(xi) SEQUENCE DESCRIPTION: SEQ ID NO:106:

CGCGATTAAT CATCAGTGTA CAGTTTAGGA CTAACAATCC ATTTATTAGT AGCAGAAAGA     60

AGTTTAAAAT CTTGCTTTCT GATATAATTT GTTTTGTAG                            99

(2) INFORMATION FOR SEQ ID NO:107:

(i) SEQUENCE CHARACTERISTICS:
        (A) LENGTH: 49 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence downstream of hMSH2
            exon 13

(xi) SEQUENCE DESCRIPTION: SEQ ID NO:107:

GTAAGTGCAT CTCCTAGTCC CTTGAAGATA GAAATGTATG TCTCTGTCC                 49

(2) INFORMATION FOR SEQ ID NO:108:

(i) SEQUENCE CHARACTERISTICS:
        (A) LENGTH: 47 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO
```

(vii) IMMEDIATE SOURCE:
            (B) CLONE: confirmed intron sequence upstream of hMSH2
                exon 14

(xi) SEQUENCE DESCRIPTION: SEQ ID NO:108:

TACCACATTT TATGTGATGG GAAATTTCAT GTAATTATGT GCTTCAG                        47

(2) INFORMATION FOR SEQ ID NO:109:

(i) SEQUENCE CHARACTERISTICS:
            (A) LENGTH: 58 base pairs
            (B) TYPE: nucleic acid
            (C) STRANDEDNESS: both
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: confirmed exon sequence downstream of hMSH2
                exon 14

(xi) SEQUENCE DESCRIPTION: SEQ ID NO:109:

GTATGTACTA TTGGAGTACT CTAAATTCAG AACTTGGTAA TGGGAAACTT ACTACCCC           58

(2) INFORMATION FOR SEQ ID NO:110:

(i) SEQUENCE CHARACTERISTICS:
            (A) LENGTH: 44 base pairs
            (B) TYPE: nucleic acid
            (C) STRANDEDNESS: both
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: confirmed intron sequence upstream of hMSH2

(xi) SEQUENCE DESCRIPTION: SEQ ID NO:110:

CTCTTCTCAT GCTGTCCCCT CACGCTTCCC CAAATTTCTT ATAG                           44

(2) INFORMATION FOR SEQ ID NO:111:

(i) SEQUENCE CHARACTERISTICS:
            (A) LENGTH: 41 base pairs
            (B) TYPE: nucleic acid
            (C) STRANDEDNESS: both
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: confirmed intron sequence downstream of hMSH2
                exon 15

(xi) SEQUENCE DESCRIPTION: SEQ ID NO:111:

GTTTGTCAGT TTGTTTTCAT AGTTTAACTT AGCTTCTCTA T                             41

(2) INFORMATION FOR SEQ ID NO:112:

```
    (i) SEQUENCE CHARACTERISTICS:
        (A) LENGTH: 33 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed intron sequence upstream of hMSH2
            exon 16

(xi) SEQUENCE DESCRIPTION: SEQ ID NO:112:

TAATTACTCA TGGGACATTC ACATGTGTTT CAG                                 33

(2) INFORMATION FOR SEQ ID NO:113:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: confirmed sequence downstream of hMSH2 exon
            16

(xi) SEQUENCE DESCRIPTION: SEQ ID NO:113:

AAAATCCCAG TAATGGAATG AAGGTA                                         26

(2) INFORMATION FOR SEQ ID NO:114:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence downstream of hMSH2 exon 1

(xi) SEQUENCE DESCRIPTION: SEQ ID NO:114:

GTGAGGGCCG GGACGGCGCG TGCTGGGGAG GGACCCGGGG CCTTGTGGCG CGGCTCCTTT     60

CCCGCCTCAG AGAGTGGGCG GTGAGCAGCC TCTCCAGTGC GGAGGCACGG CGGGCGGAAC   120

GTTGGTGCTT GTGCGGATTC CGCCGTCCCC AGGTTC                             156

(2) INFORMATION FOR SEQ ID NO:115:

(i) SEQUENCE CHARACTERISTICS:
        (A) LENGTH: 126 base pairs
        (B) TYPE: nucleic acid
        (C) STRANDEDNESS: both
        (D) TOPOLOGY: linear
```

(ii) MOLECULE TYPE: DNA (genomic)

(iii) HYPOTHETICAL: NO (iv) ANTI-SENSE: NO (vii) IMMEDIATE SOURCE:
              (B) CLONE: intron sequence upstream of hMSH2 exon 2

(xi) SEQUENCE DESCRIPTION: SEQ ID NO:115:

```
AAGTCCAGTA AGCTCTTTTT TCTTCCCAGT CTCGGGTATG TCTTTATCAG CAGCATGAAG      60

TCCAGCTAAT ACAGTGCTTG AACATGTAAT ATCTCAAATC TGTAATGTAC TTTTTTTTTT     120

TTTAAG                                                                126
```

(2) INFORMATION FOR SEQ ID NO:116:

(i) SEQUENCE CHARACTERISTICS:
              (A) LENGTH: 81 base pairs
              (B) TYPE: nucleic acid
              (C) STRANDEDNESS: both
              (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: intron sequence downstream of hMSH2 exon 2

(xi) SEQUENCE DESCRIPTION: SEQ ID NO:116:

```
GTAATTATCT TCCTTTTTAA TTTACTTATT TTTTTAAGAG TAGAAAAATA AAAATGTGAA      60

GAATTTAATT GTGTTTTTAG T                                                81
```

(2) INFORMATION FOR SEQ ID NO:117:

(i) SEQUENCE CHARACTERISTICS:
              (A) LENGTH: 101 base pairs
              (B) TYPE: nucleic acid
              (C) STRANDEDNESS: both
              (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: intron sequence upstream of hMSH2 exon 3

(xi) SEQUENCE DESCRIPTION: SEQ ID NO:117:

```
ATTAATAAGG TTCATAGAGT TTGGATTTTT CCTTTTTGCT TATAAAATTT TAAAGTATGT      60

TCAAGAGTTT GTTAAATTTT TAAAATTTTA TTTTTACTTA G                        101
```

(2) INFORMATION FOR SEQ ID NO:118:

(i) SEQUENCE CHARACTERISTICS:
              (A) LENGTH: 71 base pairs
              (B) TYPE: nucleic acid
              (C) STRANDEDNESS: both
              (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: intron sequence downstream of hMSH2 exon 3

(xi) SEQUENCE DESCRIPTION: SEQ ID NO:118:

GTAAGCAAAT TGAGTCTAGT GATAGAGGAG ATTCCAGGCC TAGGAAAGGC TCTTTAATTG      60

ACATGATACT G                                                          71

(2) INFORMATION FOR SEQ ID NO:119:

(i) SEQUENCE CHARACTERISTICS:
            (A) LENGTH: 174 base pairs
            (B) TYPE: nucleic acid
            (C) STRANDEDNESS: both
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: intron sequence upstream of hMSH2 exon 4

(xi) SEQUENCE DESCRIPTION: SEQ ID NO:119:

TTTAGTTTAT TGATGTAAAA AGTGTATCAG TACATCATAT CAGTGTCTTG CACATTGTAT      60

AAACATTTAA TGTAGGTGAA TCTGTTATCA CTATAGTTAT CAATGTTATA ATTTTCATTT     120

TTGCTTTTCT TATTCCTTTT CTCATAGTAG TTTAAACTAT TTCTTTCAAA ATAG           174

(2) INFORMATION FOR SEQ ID NO:120:

(i) SEQUENCE CHARACTERISTICS:
            (A) LENGTH: 138 base pairs
            (B) TYPE: nucleic acid
            (C) STRANDEDNESS: both
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: intron sequence downstream of hMSH2 exon 4

(xi) SEQUENCE DESCRIPTION: SEQ ID NO:120:

GTACATGGAT TATAAATGTG AATTACAATA TATATAATGT AAATATGTAA TATATAATAA      60

ATAATATGTA AACTATAGTG ACTTTTTAGA AGGATATTTC TGTCATATTT ATCTCAAAAA     120

CCTGTGTATC AATGATAT                                                  138

(2) INFORMATION FOR SEQ ID NO:121:

(i) SEQUENCE CHARACTERISTICS:
            (A) LENGTH: 60 base pairs
            (B) TYPE: nucleic acid
            (C) STRANDEDNESS: both
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
            (B) CLONE: intron sequence upstream of hMSH2 exon 5

(xi) SEQUENCE DESCRIPTION: SEQ ID NO:121:

AAAACCTTTA GAATGGACCA GTGGTATAGA AATCTTCGAT TTTTAAATTC TTAATTTTAG    60

(2) INFORMATION FOR SEQ ID NO:122:

(i) SEQUENCE CHARACTERISTICS:
        (A) LENGTH: 113 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: intron sequence downstream of hMSH2 exon 5

(xi) SEQUENCE DESCRIPTION: SEQ ID NO:122:

GTAAAAAAAA AAAAAAAAAA AAAAAAAAGG GTTAAAAATG TTGATTGGTT AAGACAGATA    60

GTGAAGAAGG CTTAGAAAGG AGCTAAAAGA GTTCGACATC AATATTAGAC AAG          113

(2) INFORMATION FOR SEQ ID NO:123:

(i) SEQUENCE CHARACTERISTICS:
        (A) LENGTH: 76 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: intron sequence upstream of hMSH2 exon 6

(xi) SEQUENCE DESCRIPTION: SEQ ID NO:123:

ATTGTTCCTC TTCATGGCGT AGTAAGTTTT CACTAATGAG CTTGCCATTC TTTCTATTTT    60

ATTTTTTGTT TACTAG                                                    76

(2) INFORMATION FOR SEQ ID NO:124:

(i) SEQUENCE CHARACTERISTICS:
        (A) LENGTH: 152 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: intron sequence downstream of hMSH2 exon 6

(xi) SEQUENCE DESCRIPTION: SEQ ID NO:124:

GTATGTTATT AGTTTATACT TTCGTTAGTT TTATGTAACC TGCAGTTACC CACATGATTA    60

TACCACTTAT TGTAATATGC AGTTTTGGAA GTATATGTTA CCATTTAACT GTACAGAGTA   120

CATAGTAATA GAGTGGTAAT TATTTAGATT AA                                 152

(2) INFORMATION FOR SEQ ID NO:125:

(i) SEQUENCE CHARACTERISTICS:
        (A) LENGTH: 88 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 7

(xi) SEQUENCE DESCRIPTION: SEQ ID NO:125:

```
TCGACTTAGT TGAGACTTAC GTGCTTAGTT GATAAATTTT AATTTTATAC TAAAATATTT    60

TACATTAATT CAAGTTAATT TATTTCAG                                      88
```

(2) INFORMATION FOR SEQ ID NO:126:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence downstream of hMSH2 exon 7

(xi) SEQUENCE DESCRIPTION: SEQ ID NO:126:

```
GTAACAAGTG ATTTTGTTTT TTTGTTTTCC TTCAACTCAT ACAATATATA CTTGGCAATG    60

TGCTGTCCTC ATAAAGTTGG TGGTGGTTGA CTCA                                94
```

(2) INFORMATION FOR SEQ ID NO:127:

(i) SEQUENCE CHARACTERISTICS:
        (A) LENGTH: 68 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 8

(xi) SEQUENCE DESCRIPTION: SEQ ID NO:127:

```
AAAATTTTAT GATTTGTATT CTGTAAAATG AGATCTTTTT ATTTGTTTGT TTTACTACTT    60

TCTTTTAG                                                            68
```

(2) INFORMATION FOR SEQ ID NO:128:

(i) SEQUENCE CHARACTERISTICS:
        (A) LENGTH: 126 base pairs
        (B) TYPE: nucleic acid
        (C) STRANDEDNESS: both (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence downstream of hMSH2 intron 8

(xi) SEQUENCE DESCRIPTION: SEQ ID NO:128:

```
GTATGCAATA TACTTTTTAA TTTAAGCAGT AGTTATTTTT AAAAAGCAAA GGCCACTTTA      60

AGAAAGTTTG TAGATTTTTT TTTTTAGTAT CTAAATGTAG CACCTTTGTG GACAGTGGAT     120

GTAATA                                                                126
```

(2) INFORMATION FOR SEQ ID NO:129:

(i) SEQUENCE CHARACTERISTICS:
        (A) LENGTH: 271 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 9

(xi) SEQUENCE DESCRIPTION: SEQ ID NO:129:

```
AAATGTAGAA TACTATTGGG GGCATATACA TCATCAGCAC TGTAACTGTT TCATATGAAT      60

CATTTTTGTA CATATAGAAC TCTAAAGTCC TAATGAACAG AATTTTACAT TTCTATAAAT     120

AGAAAGTCCT AATAGTTGT GACTGAATAA CTTATGGATA GCAAATTATT TAACTGAAAA     180

CAGTAAAATT TAAGTGGGAG GAAATATTTG CTTTATAATT TCTGTCTTTA CCCATTATTT     240

ATAGGATTTT GTCACTTTGT TCTGTTTGCA G                                    271
```

(2) INFORMATION FOR SEQ ID NO:130:

(i) SEQUENCE CHARACTERISTICS:
        (A) LENGTH: 261 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence downstream of hMSH2 exon 9

(xi) SEQUENCE DESCRIPTION: SEQ ID NO:130:

```
GTAAGAATGG GTCATTGGAG GTTGGAATAA TTCTTTTGTC TATACACTGT ATAGACAAAA      60

TATTGATGCC AGAATTATTT TATAAGTTCC CTGTCCCCAA GATGATGACT CCACGTCCCT     120

GTCAAACAGA AATCGCCCAA CAGGCCCTTG TATGATGTCA TTTAAACAAG CCCTATTTTA     180

AATGTCACCT CCACTGGTAA CAGGATACTC CTAGGAGGAT CACCAAGCCC AATTCTTCTA     240

GGAGTAGTGC ATTGATTAGG C                                               261
```

(2) INFORMATION FOR SEQ ID NO:131:

(i) SEQUENCE CHARACTERISTICS:
        (A) LENGTH: 390 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 10

(xi) SEQUENCE DESCRIPTION: SEQ ID NO:131:

```
AAATACCTTT GGTTAAGAAA AGAATTCTCA TGCATAACTC CTCGAGGGTG GGGTTACACC      60
TTAATCCATC CTCAGGTGCT CATGGTAAGT GGGGCAAATA TGTTGCCCAG TGCTGGTGCT     120
CTGCAGCCTT GGATGGGTTT ACCCAGAAAG CAGCTTTCAA GTCAGAAACT AACATTCATA     180
AGGGAGTTAA GGATTTTATA AATAGATATC CATAATTCAT GTAGTTTTCA AGTAAGTAGT     240
ATTTGAATCT TTTCTGGTTA GATAATAATT GTGAGTATGT TGTCATATAA TAACAGTATT     300
TTTTTCACTA TTTAAATAAT TTTAGAATTA CATTGAAAAA TGGTAGTAGG TATTTATGGA     360
ATACTTTTTC TTTTCTTCTT GTTTATCAAG                                      390
```

(2) INFORMATION FOR SEQ ID NO:132:

(i) SEQUENCE CHARACTERISTICS:
        (A) LENGTH: 490 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence downstream of hMSH2 exon 10

(xi) SEQUENCE DESCRIPTION: SEQ ID NO:132:

```
GTTTGTAAGT CATTATTATA TTTTTAACCC TTTATTAATT CCCTAAATGC TCTAACATGA      60
TGTGAATGTT CTATGATAAG TTTTACTAAT GTAGTCATCA GGTAAGAGTC AAGCTTTCTT     120
CCATAGAGCA GTCAGCTGTC GCAACACCAT TTGTTAAATA GCCCGCCTGT TCTCCATTGA     180
CTGAAGTGGT ACTTTGGGTC TATTTTAAAG ACTCTACTTT TACCTCGCCT CACCATTCTT     240
TTGTCTACAC AAAATATATT TTATCGCTTA TTCTGTGTTA CCATATCTAT TAGAGCTAGT     300
TCCCGCTCAT ATCTCTGCTT TAGTTATTTT CACATGTTTC TTTTATCTTT TTTTTTTTGG     360
AGACGGAGTC TCGCTCTGTT GCCCAGGCTG GAGTGCAGCG GCATGATCTC GGCTCACTGC     420
AAGCTCCGCC TTCCGGGTTC ACGCCATTCT CCTGCCTCAG CTCCCGAGTA GCTGGGATTA     480
CAGAAGCCGC                                                           490
```

(2) INFORMATION FOR SEQ ID NO:133:

(i) SEQUENCE CHARACTERISTICS:
        (A) LENGTH: 302 base pairs
        (B) TYPE: nucleic acid
        (C) STRANDEDNESS: both (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 11

(xi) SEQUENCE DESCRIPTION: SEQ ID NO:133:

```
AAATAAGGAT TCCATTTAAA TATTTTGTAA AAGGACACAG ATCACAGTTT TACTCAGGGG    60
AATATAATTG TTATAGCAGG AATTGTGCCA TTGCGCTATT CCACACAGTG TAAAAGAACA   120
TTAATAAATT GAATTCTAAC TACATTTGTC CCTAAGGAGT TGTTCGTTTT CCACTTGTAT   180
TTCCATTTTA ATTATCATTA TTTGGATGTT TCATAGGATA CTTTGGATAT GTTTCACGTA   240
GTACACATTG CTTCTAGTAC ACATTTTAAT ATTTTTAATA AAACTGTTAT TTCGATTTGC   300
AG                                                                 302
```

(2) INFORMATION FOR SEQ ID NO:134:

(i) SEQUENCE CHARACTERISTICS:
        (A) LENGTH: 466 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence downstream of hMSH2 exon 11

(xi) SEQUENCE DESCRIPTION: SEQ ID NO:134:

```
GTAAACTTAA TAGAACTAAT AATGTTCTGA ATGTCACCTG GCTTTTGGTA ACAGAAGAAA    60
AATCATGATA TTTGAAGTGT GTTTTGTTAT TTTCGCAAGC CATTACGTTC TGACTATTTA   120
ATATGTTAGG TTTCCTATAT AAAATAAGGC ATGGTATGTT ACAGTAGGAC ACATAACTGG   180
AAATTACTCT TGCACATAGA AACAAAAAAT GGCAGAAAAG CACAAAACTT ACTATAGTTG   240
TAACAGGGAA AGGAAACACT AGGGCCTACA ACGTACTAAT GTCTTGGGTC ATCTATGGGC   300
TCATGAGGCT CTAGGTTATG GAAGTAATAC CACTGAAAAG CAATATTATT ACACATGAGG   360
CAGCCTTTTG AGTTCTGTAT GTCATTTGTA GATTTGAGTT CATCTAGTGG CACATTTGAG   420
ATCATTTCAT GTAATAAAGG ACACAGCAAC TGGCACTGTG TTATGG                 466
```

(2) INFORMATION FOR SEQ ID NO:135:

(i) SEQUENCE CHARACTERISTICS:
        (A) LENGTH: 308 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 12

(xi) SEQUENCE DESCRIPTION: SEQ ID NO:135:

```
GGCTCATGCG ACCTGCCGCT CAGCTCCTAG TGCTGGATAT AGCGTGAGCC CACACCAGCC      60

AGTACTCTGT TTTTGATAGC TATCACAATG GGAAAGGATG TAGCAACACA TTTTAACCCT     120

ATGTTGAGTT TTAGGTGGGT TCCTTTGAAA TTTTGTTAAG GCTAACTTTT GTTAATTTTT     180

TTAAAAAGT GTAAATTAGG AAATGGGTTT TGAATTCCCA AATGGGGGGA TTAAATGTAT      240

TTTTACGGCT TATATCTGTT TATTATTCAG TATTCCTGTG TACATTTTCT GTTTTTATTT     300

TTATACAG                                                             308
```

(2) INFORMATION FOR SEQ ID NO:136:

(i) SEQUENCE CHARACTERISTICS:
        (A) LENGTH: 151 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence downstream of hMSH2 exon 12

(xi) SEQUENCE DESCRIPTION: SEQ ID NO:136:

```
GTAAAAACC TGGTTTTTGG GCTTTGTGGG GGTAACGTTT TGTTTTTTTT TTTTTTTTT       60

AATCTTGGAG TAGAAATATA TTTAAAATTG ATGGAGAAAA TTCCCAGTTC TTAACATTAG    120

AAAGGGAATA TATTATTCTT ACCAGTTAGT A                                   151
```

(2) INFORMATION FOR SEQ ID NO:137:

(i) SEQUENCE CHARACTERISTICS:
        (A) LENGTH: 267 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 13

(xi) SEQUENCE DESCRIPTION: SEQ ID NO:137:

```
CAGATAACAG GTATATTTGT CATGGCTTCT CTTGATGAAA GGCCCAGAAT CGGTTTGTCT      60

GAAGATATAT AATAGCTTTG CTTTTGGGGG TAATATGGGC AGTAACTCTG TCCACATCTG    120

TGGGCAGGCT GTGGTTCTGC TGATATATGC TATGTCAGTG TAAACCTACG CGATTAATCA    180

TCAGTGTACA GTTTAGGACT AACAATCCAT TTATTAGTAG CAGAAAGAAG TTTAAAATCT    240

TGCTTTCTGA TATAATTTGT TTTGTAG                                       267
```

(2) INFORMATION FOR SEQ ID NO:138:

(i) SEQUENCE CHARACTERISTICS:
        (A) LENGTH: 251 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: intron sequence downstream of hMSH2 exon 13

(xi) SEQUENCE DESCRIPTION: SEQ ID NO:138:

```
GTAAGTGCAT CTCCTAGTCC CTTGAAGATA GAAATGTATG TCTCTGTCCT GTGAGAAGGA        60

AAAGTATATT TGCAGATTCT CATGTAAAAA CATCTGAGAA TGTTTGTCTT AGTTTAATAG       120

TTGTTTTCCT GTGGACTTTA TATACTTTGT ATTGTCTTAA AAGAGTGATT GATGATAGCT       180

ACGGAAAACT TTGATTTTTA AAATTGTCTC TTTAAGTAGA CAATTTATAA GCTACTGGTA       240

CGAGTTCACC T                                                            251
```

(2) INFORMATION FOR SEQ ID NO:139:

(i) SEQUENCE CHARACTERISTICS:
            (A) LENGTH: 298 base pairs
            (B) TYPE: nucleic acid
            (C) STRANDEDNESS: both
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: intron sequence upstream of hMSH2 exon 14

(xi) SEQUENCE DESCRIPTION: SEQ ID NO:139:

```
TTTTTTTTTT TTTTTTTTAG AGGCGAGGTC TCACTATGTG CTCAGGCTGG TCTGGGGCTC        60

AAGTGATCCT CCCACCCCGC CTCCAAATGC TGGGATTACA GACGTGAGCC ATCATGCCTG       120

GCCCTTGCCC ATTTTTCTAG TGAAGTTTTA GTGCTTTTTA TTGACTTTGT TTATATATTA       180

AGATGATCCA TTATGTTTGT GGCATATCCT TCCCAATGTA TTGTCATAAT TTTGTTTTTG       240

TATGTGTATG TTACCACATT TTATGTGATG GGAAATTTCA TGTAATTATG TGCTTCAG        298
```

(2) INFORMATION FOR SEQ ID NO:140:

(i) SEQUENCE CHARACTERISTICS:
            (A) LENGTH: 59 base pairs
            (B) TYPE: nucleic acid
            (C) STRANDEDNESS: both
            (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: intron sequence downstream of hMSH2 exon 14

(xi) SEQUENCE DESCRIPTION: SEQ ID NO:140:

```
GTATGTACTA TTGGAGTACT CTAAATTCAG AACTTGGTAA TGGGAAACTT ACTACCCCT         59
```

(2) INFORMATION FOR SEQ ID NO:141:

(i) SEQUENCE CHARACTERISTICS:
            (A) LENGTH: 81 base pairs
            (B) TYPE: nucleic acid

```
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 15

(xi) SEQUENCE DESCRIPTION: SEQ ID NO:141:

CGAGGTGAGA GGATAAATCC ATTACATAAA TTGCTGTCTC TTCTCATGCT GTCCCCTCAC    60

GCTTCCCCAA ATTTCTTATA G                                             81

(2) INFORMATION FOR SEQ ID NO:142:

(i) SEQUENCE CHARACTERISTICS:
        (A) LENGTH: 244 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence downstream of hMSH2 exon 15

(xi) SEQUENCE DESCRIPTION: SEQ ID NO:142:

GTTTGTCAGT TTGTTTTCAT AGTTTAACTT AGCTTCTCTA TTATTACATA AACAGGACAC    60

TAAGATGAAG GTTTTTTGTC GTCGTTTGTT TCCCTCTGTG TTTCTAGTGC TTATTTTCTA   120

ATCAGTTTTT TTGATGGCAA AGAATCTATC TCTGTGTTAT TTTGATTTCT GCAGCATATA   180

CATCTGCATG ATCAATATTC GATTTCAAGT ACCAAAGTAG GAGTAAAGGA ATATTAACCT   240

AGGT                                                                244

(2) INFORMATION FOR SEQ ID NO:143:

(i) SEQUENCE CHARACTERISTICS:
        (A) LENGTH: 183 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: intron sequence upstream of hMSH2 exon 16

(xi) SEQUENCE DESCRIPTION: SEQ ID NO:143:

TGTGGGAGGA GTTTGAGACC ACCCTGGGCC CATAGTGAGA CCCTCTTCTC TCAAAATATG    60

AAAAAAAAAA AAAATTTTT AAATGTGTGA TATGTTTAGA TGGAAATGAC AATTTGTCAC    120

TCTCTCACAT GACTTTTAGA AAAGATATTT TAATTACTCA TGGGACATTC ACATGTGTTT   180

CAG                                                                 183

(2) INFORMATION FOR SEQ ID NO:144:
```

```
    (i) SEQUENCE CHARACTERISTICS:
        (A) LENGTH: 272 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: sequence downstream of hMSH2 exon 16

(xi) SEQUENCE DESCRIPTION: SEQ ID NO:144:

AAAATCCCAG TAATGGAATG AAGGTAATAT TGATAAGCTA TTGTCTGTAA TAGTTTTATA       60

TTGTTTTATA TTAACCCTTT TTCCATAGTG TTAACTGTCA GTGCCCATGG GCTATCAACT      120

TAATAAGATA TTTAGTAATA TTTTACTTTG AGGACATTTT CAAAGATTTT TATTTTGAAA      180

AATGAGAGCT GTAACTGAGG ACTGTTTGCA ATTGACATAG GCAATAATAA GTGATGTGCT      240

GAATTTTATA AATAAAATCA TGTAGTTTGT GG                                    272

(2) INFORMATION FOR SEQ ID NO:145:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 16061

(xi) SEQUENCE DESCRIPTION: SEQ ID NO:145:

GAGGAGGAAT TCTGATCACA G                                                21

(2) INFORMATION FOR SEQ ID NO:146:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 16062

(xi) SEQUENCE DESCRIPTION: SEQ ID NO:146:

CTGCAACCTG ATTCTCCA                                                    18

(2) INFORMATION FOR SEQ ID NO:147:

(i) SEQUENCE CHARACTERISTICS:
        (A) LENGTH: 41 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (vii) IMMEDIATE SOURCE:
         (B) CLONE: primer 18415

(xi) SEQUENCE DESCRIPTION: SEQ ID NO:147:

TGTAAAACGA CGGCCAGTCT TTACCCATTA TTTATAGGAT T                41

(2) INFORMATION FOR SEQ ID NO:148:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: primer 18783

(xi) SEQUENCE DESCRIPTION: SEQ ID NO:148:

ATAGACAAAA GAATTATTCC AAC                                     23

(2) INFORMATION FOR SEQ ID NO:149:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: primer 18413

(xi) SEQUENCE DESCRIPTION: SEQ ID NO:149:

TGTAAAACGA CGGCCAGTTA GTAGGTATTT ATGGAATACT TTT              43

(2) INFORMATION FOR SEQ ID NO:150:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: primer 18849

(xi) SEQUENCE DESCRIPTION: SEQ ID NO:150:

TGTTAGAGCA TTTAGGGAAT T                                       21

(2) INFORMATION FOR SEQ ID NO:151:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18215

(xi) SEQUENCE DESCRIPTION: SEQ ID NO:151:

TGTAAAACGA CGGCCAGTCA TTGCTTCTAG TACACATTT        39

(2) INFORMATION FOR SEQ ID NO:152:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18228

(xi) SEQUENCE DESCRIPTION: SEQ ID NO:152:

CAGGTGACAT TCAGAACATT A        21

(2) INFORMATION FOR SEQ ID NO:153:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: primer 18216

(xi) SEQUENCE DESCRIPTION: SEQ ID NO:153:

TGTAAAACGA CGGCCAGTTC AGTATTCCTG TGTACATTT        39

(2) INFORMATION FOR SEQ ID NO:154:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
    (B) CLONE: primer 18227

(xi) SEQUENCE DESCRIPTION: SEQ ID NO:154:

TTACCCCCAC AAAGCCCAA                                            19

(2) INFORMATION FOR SEQ ID NO:155:

(i) SEQUENCE CHARACTERISTICS:
        (A) LENGTH: 2484 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: hMLH1 cDNA (xi) SEQUENCE DESCRIPTION: SEQ ID NO:155:

```
CTTGGCTCTT CTGGCGCCAA AATGTCGTTC GTGGCAGGGG TTATTCGGCG GCTGGACGAG    60

ACAGTGGTGA ACCGCATCGC GGCGGGGGAA GTTATCCAGC GGCCAGCTAA TGCTATCAAA   120

GAGATGATTG AGAACTGTTT AGATGCAAAA TCCACAAGTA TTCAAGTGAT TGTTAAAGAG   180

GGAGGCCTGA AGTTGATTCA GATCCAAGAC AATGGCACCG GGATCAGGAA AGAAGATCTG   240

GATATTGTAT GTGAAAGGTT CACTACTAGT AAACTGCAGT CCTTTGAGGA TTTAGCCAGT   300

ATTTCTACCT ATGGCTTTCG AGGTGAGGCT TTGGCCAGCA TAAGCCATGT GGCTCATGTT   360

ACTATTACAA CGAAAACAGC TGATGGAAAG TGTGCATACA GAGCAAGTTA CTCAGATGGA   420

AAACTGAAAG CCCCTCCTAA ACCATGTGCT GGCAATCAAG GGACCCAGAT CACGGTGGAG   480

GACCTTTTTT ACAACATAGC CACGAGGAGA AAAGCTTTAA AAAATCCAAG TGAAGAATAT   540

GGGAAAATTT TGGAAGTTGT TGGCAGGTAT TCAGTACACA ATGCAGGCAT TAGTTTCTCA   600

GTTAAAAAAC AAGGAGAGAC AGTAGCTGAT GTTAGGACAC TACCCAATGC CTCAACCGTG   660

GACAATATTC GCTCCATCTT TGGAAATGCT GTTAGTCGAG AACTGATAGA AATTGGATGT   720

GAGGATAAAA CCCTAGCCTT CAAAATGAAT GGTTACATAT CCAATGCAAA CTACTCAGTG   780

AAGAAGTGCA TCTTCTTACT CTTCATCAAC CATCGTCTGG TAGAATCAAC TTCCTTGAGA   840

AAAGCCATAG AAACAGTGTA TGCAGCCTAT TTGCCCAAAA ACACACACCC ATTCCTGTAC   900

CTCAGTTTAG AAATCAGTCC CCAGAATGTG GATGTTAATG TGCACCCCAC AAAGCATGAA   960

GTTCACTTCC TGCACGAGGA GAGCATCCTG GAGCGGGTGC AGCAGCACAT CGAGAGCAAG  1020

CTCCTGGGCT CCAATTCCTC CAGGATGTAC TTCACCCAGA CTTTGCTACC AGGACTTGCT  1080

GGCCCCTCTG GGGAGATGGT TAAATCCACA ACAAGTCTGA CCTCGTCTTC TACTTCTGGA  1140

AGTAGTGATA AGGTCTATGC CCACCAGATG GTTCGTACAG ATTCCCGGGA ACAGAAGCTT  1200

GATGCATTTC TGCAGCCTCT GAGCAAACCC CTGTCCAGTC AGCCCCAGGC CATTGTCACA  1260

GAGGATAAGA CAGATATTTC TAGTGGCAGG GCTAGGCAGC AAGATGAGGA GATGCTTGAA  1320

CTCCCAGCCC CTGCTGAAGT GGCTGCCAAA AATCAGAGCT TGGAGGGGGA TACAACAAAG  1380

GGGACTTCAG AAATGTCAGA GAAGAGAGGA CCTACTTCCA GCAACCCCAG AAAGAGACAT  1440

CGGGAAGATT CTGATGTGGA AATGGTGGAA GATGATTCCC GAAAGGAAAT GACTGCAGCT  1500
```

-continued

```
TGTACCCCCC GGAGAAGGAT CATTAACCTC ACTAGTGTTT TGAGTCTCCA GGAAGAAATT      1560

AATGAGCAGG GACATGAGGT TCTCCGGGAG ATGTTGCATA ACCACTCCTT CGTGGGCTGT      1620

GTGAATCCTC AGTGGGCCTT GGCACAGCAT CAAACCAAGT TATACCTTCT CAACACCACC      1680

AAGCTTAGTG AAGAACTGTT CTACCAGATA CTCATTTATG ATTTTGCCAA TTTTGGTGTT      1740

CTCAGGTTAT CGGAGCCAGC ACCGCTCTTT GACCTTGCCA TGCTTGCCTT AGATAGTCCA      1800

GAGAGTGGCT GGACAGAGGA AGATGGTCCC AAAGAAGGAC TTGCTGAATA CATTGTTGAG      1860

TTTCTGAAGA AGAAGGCTGA GATGCTTGCA GACTATTTCT CTTTGGAAAT TGATGAGGAA      1920

GGGAACCTGA TTGGATTACC CCTTCTGATT GACAACTATG TGCCCCCTTT GGAGGGACTG      1980

CCTATCTTCA TTCTTCGACT AGCCACTGAG GTGAATTGGG ACGAAGAAAA GGAATGTTTT      2040

GAAAGCCTCA GTAAAGAATG CGCTATGTTC TATTCCATCC GGAAGCAGTA CATATCTGAG      2100

GAGTCGACCC TCTCAGGCCA GCAGAGTGAA GTGCCTGGCT CCATTCCAAA CTCCTGGAAG      2160

TGGACTGTGG AACACATTGT CTATAAAGCC TTGCGCTCAC ACATTCTGCC TCCTAAACAT      2220

TTCACAGAAG ATGGAAATAT CCTGCAGCTT GCTAACCTGC CTGATCTATA CAAAGTCTTT      2280

GAGAGGTGTT AAATATGGTT ATTTATGCAC TGTGGGATGT GTTCTTCTTT CTCTGTATTC      2340

CGATACAAAG TGTTGTATCA AAGTGTGATA TACAAAGTGT ACCAACATAA GTGTTGGTAG      2400

CACTTAAGAC TTATACTTGC CTTCTGATAG TATTCCTTTA TACACAGTGG ATTGATTATA      2460

AATAAATAGA TGTGTCTTAA CATA                                             2484
```

(2) INFORMATION FOR SEQ ID NO:156:

(i) SEQUENCE CHARACTERISTICS:
        (A) LENGTH: 756 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vii) IMMEDIATE SOURCE:
        (B) CLONE: hMlh1 protein (xi) SEQUENCE DESCRIPTION: SEQ ID NO:156:

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125
```

-continued

```
Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
                180                 185                 190

Ser Val Lys Lys Gln Gly Glu Thr Val Ala Asp Val Arg Thr Leu Pro
            195                 200                 205

Asn Ala Ser Thr Val Asp Asn Ile Arg Ser Ile Phe Gly Asn Ala Val
        210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
                260                 265                 270

Arg Lys Ala Ile Glu Thr Val Tyr Ala Ala Tyr Leu Pro Lys Asn Thr
            275                 280                 285

His Pro Phe Leu Tyr Leu Ser Leu Glu Ile Ser Pro Gln Asn Val Asp
        290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
                340                 345                 350

Ala Gly Pro Ser Gly Glu Met Val Lys Ser Thr Thr Ser Leu Thr Ser
            355                 360                 365

Ser Ser Thr Ser Gly Ser Ser Asp Lys Val Tyr Ala His Gln Met Val
        370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
                420                 425                 430

Glu Leu Pro Ala Pro Ala Glu Val Ala Ala Lys Asn Gln Ser Leu Glu
            435                 440                 445

Gly Asp Thr Thr Lys Gly Thr Ser Glu Met Ser Glu Lys Arg Gly Pro
        450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
                500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
        530                 535                 540

Thr Lys Leu Tyr Leu Leu Asn Thr Thr Lys Leu Ser Glu Glu Leu Phe
```

```
             545                 550                 555                 560
        Tyr Gln Ile Leu Ile Tyr Asp Phe Ala Asn Phe Gly Val Leu Arg Leu
                    565                 570                 575

Ser Glu Pro Ala Pro Leu Phe Asp Leu Ala Met Leu Ala Leu Asp Ser
                    580                 585                 590

Pro Glu Ser Gly Trp Thr Glu Glu Asp Gly Pro Lys Glu Gly Leu Ala
                    595                 600                 605

Glu Tyr Ile Val Glu Phe Leu Lys Lys Lys Ala Glu Met Leu Ala Asp
                    610                 615                 620

Tyr Phe Ser Leu Glu Ile Asp Glu Glu Gly Asn Leu Ile Gly Leu Pro
        625                 630                 635                 640

Leu Leu Ile Asp Asn Tyr Val Pro Pro Leu Glu Gly Leu Pro Ile Phe
                    645                 650                 655

Ile Leu Arg Leu Ala Thr Glu Val Asn Trp Asp Glu Glu Lys Glu Cys
                    660                 665                 670

Phe Glu Ser Leu Ser Lys Glu Cys Ala Met Phe Tyr Ser Ile Arg Lys
                    675                 680                 685

Gln Tyr Ile Ser Glu Glu Ser Thr Leu Ser Gly Gln Gln Ser Glu Val
                    690                 695                 700

Pro Gly Ser Ile Pro Asn Ser Trp Lys Trp Thr Val Glu His Ile Val
        705                 710                 715                 720

Tyr Lys Ala Leu Arg Ser His Ile Leu Pro Pro Lys His Phe Thr Glu
                    725                 730                 735

Asp Gly Asn Ile Leu Gln Leu Ala Asn Leu Pro Asp Leu Tyr Lys Val
                    740                 745                 750

Phe Glu Arg Cys
                755

(2) INFORMATION FOR SEQ ID NO:157:

(i) SEQUENCE CHARACTERISTICS:
        (A) LENGTH: 237 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: non-confirmed sequence upstream of hMSH2
             exon 1

(xi) SEQUENCE DESCRIPTION: SEQ ID NO:157:

ACCTAGCAGC ATGCGCAGTA GCTAAAGTCA CCAGCGTGCG CGGGAAGCTG GGCCGCGTCT      60

GCTTATGATT GGTTGCCGCG GCAGACTCCC ACCCACCGAA ACGCAGCCCT GGAAGCTGAT     120

TGGGTGTGGT CGCCGTGGCC GGACGCCGCT CGGGGGACGT GGGAGGGGAG GCGGGAAACA     180

GCTTAGTGGG TGTGGGGTCG CGCATTTTCT TCAACCAGGA GGTGAGGAGG TTTCGAC        237
```